(12) United States Patent
Lilly et al.

(10) Patent No.: US 9,597,386 B2
(45) Date of Patent: Mar. 21, 2017

(54) **OUTER MEMBRANE PROTEINS OF *HISTOPHILUS SOMNI* AND METHODS THEREOF**

(71) Applicants: Brice Dean Lilly, St. Joseph, MO (US); Jeffrey P. Knittel, Parkville, MO (US)

(72) Inventors: Brice Dean Lilly, St. Joseph, MO (US); Jeffrey P. Knittel, Parkville, MO (US)

(73) Assignee: Boehringer Ingelheim Vetmedica, Inc., St. Joseph, MO (US)

( * ) Notice: Subject to any disclaimer, the term of this patent is extended or adjusted under 35 U.S.C. 154(b) by 56 days.

(21) Appl. No.: 13/796,653

(22) Filed: Mar. 12, 2013

(65) Prior Publication Data

US 2013/0266613 A1 Oct. 10, 2013

Related U.S. Application Data

(60) Provisional application No. 61/620,652, filed on Apr. 5, 2012.

(51) Int. Cl.
| | | |
|---|---|---|
| *A61K 39/02* | (2006.01) | |
| *A61K 39/102* | (2006.01) | |
| *A61K 39/00* | (2006.01) | |
| *G01N 33/68* | (2006.01) | |
| *G01N 33/569* | (2006.01) | |
| *C07K 14/285* | (2006.01) | |

(52) U.S. Cl.
CPC .......... *A61K 39/102* (2013.01); *C07K 14/285* (2013.01); *G01N 33/56911* (2013.01); *G01N 33/6854* (2013.01); *A61K 2039/552* (2013.01); *G01N 2333/285* (2013.01)

(58) Field of Classification Search
CPC ................................ A61K 39/00; A61K 39/02
USPC ............ 424/184.1, 234.1, 256.1, 278.1, 93.4
See application file for complete search history.

(56) References Cited

U.S. PATENT DOCUMENTS

| 5,534,256 A | 7/1996 | Potter et al. |
| 5,985,289 A * | 11/1999 | Potter et al. ............... 424/256.1 |
| 6,100,066 A | 8/2000 | Potter et al. |
| 2013/0266613 A1 | 10/2013 | Lilly et al. |

FOREIGN PATENT DOCUMENTS

| EP | 0635055 A1 | 1/1995 |
| WO | 0018429 A2 | 4/2000 |
| WO | 2013151979 A1 | 10/2013 |

OTHER PUBLICATIONS

Silva, S.V.P.S., et al. Can. J. Vet Res., vol. 54, pp. 326-330, 1990.*
Stephens, L.R., et al. Am. J. Vet. Res., vol. 45, No. 2, pp. 234-239, 1984.*
Tagawa et al. Infection and Immunity, 61(10):4153-4157, Oct. 1993.*
Cairns et al., "Efficacy of an outer Membrane Complex Haemophilus somnus Bacterin in Preventing Symptoms Following Haemophilus somnus Challenge". Agri-Practice, vol. 14, No. 8, 1993, pp. 35-37.
International Search Report and Written Opinion for PCT/US2013/034918 mailed Aug. 9, 2013.
Stephens et al., "Isolation of Haemophilus somnus antigens and their use as vaccines for prevention of bovine thromboembolic meningoencephalitis". American Journal of Veterinary Research, vol. 45, No. 2, Feb. 1984, pp. 234-239.
Asmussen et al., "Thiamine, Pyrophosphate (Cocarboxylase) as a Growth Factor for Haemophilus somnus". Journal of Clinical Microbiology, vol. 14, No. 2, Aug. 1981, pp. 178-183.
Babiuk et al., "Veterinary Vaccines". Biotechnology Advances, vol. 12, 1994, pp. 489-523.
Challacombe et al., "Complete Genome Sequence of Haemophilus somnus (Histophilus somni) Strain 128Pt and Comparison to Haemophilus ducreyi 35000HP and Haemophilus influenzae RdN". Journal of Bacteriology, vol. 189, No. 5, Mar. 2007, pp. 1890-1898.
Corbeil et al., "Bovine IgG2a Antibodies to Haemophilus somnus and Allotype Expression". Canadian Journal of Veterinarian Research, vol. 61, 1997, pp. 207-213.
Corbeil et al., "Characterization of Immunodominant Surface Antigens of Haemophilus somnus". Infection and Immunity, vol. 59, No. 12, Dec. 1991, pp. 4295-4301.
Corbeil et al., "Haemophilus somnus Immunoglobulin Binding Proteins and Surface Fibrils". Infection and Immunity, vol. 65, No. 10, Oct. 1997, pp. 4250-4257.
Corbeil et al., "Specificity of IgG and IgE antibody responses to Haemophilus somnus infection in calves". Veterinary Immunology and Immunopathology, vol. 113, 2006, pp. 191-199.
Corbeil, L.B., "Antibodies as effectors". Veterinary Immunology and Immunopathology, vol. 87, 2002, pp. 169-175.
Costerton, J.W., "Discussion: Introduction to biogilm". International Journal of Antimicrobial Agents, vol. 11, 1999, pp. 217-221.
Donkersgoed et al., "Effects of various vaccination protocols on passive and active immunity to Pasteurella haemolytica and Haemophilus somnus in beef calves". Canadian Veterinary Journal, vol. 36, Jul. 1995, pp. 424-429.
Geertsema et al., "Protection of mice against H. somni septicemia by vaccination with recombinant immunoglobulin binding protein subunits". Vaccine, vol. 26, 2008, pp. 4506-4512.
Gogolewski et al., "Protective Ability and Specificity of Convalescent Serum from Calves with Haemophilus somnus Pneumonia" Infection, and Immunity, vol. 55, No. 6, Jun. 1987, pp. 1403-1411.
Groβ et al., "Lipopolysaccharide-Trap-Fc, a Multifunctional Agent to Battle Gram-Negative BacteriaÑ". Infection and Immunity, vol. 77, No. 7, Jul. 2009, pp. 2925-2931.

(Continued)

*Primary Examiner* — Rodney P Swartz
(74) *Attorney, Agent, or Firm* — Michael P. Morris; Joyce L. Morrison

(57) ABSTRACT

The present invention relates to immunological compositions of outer membrane proteins (OMPs) of *H. somni*, as well as methods of extraction, a respiratory challenge model, methods of administration and diagnostic assays and kits.

**9 Claims, 11 Dr

(56) References Cited

OTHER PUBLICATIONS

Hobb et al., "Evaluation of procedures for outer membrane isolation from Campylobacter jejuni" Microbiology, Author Manuscript; available in PMC, Oct. 18, 2009, 18 pages.

Howard et al., "Antigenic Diversity of Haemophilus somnus Lipooligosaccharide: Phase-Variable Accessibility of the Phosphorylcholine Epitope". Journal of Clinical Microbiology, vol. 38, No. 12, Dec. 2000, pp. 4112-4419.

Howard, Michael D., "Antigenic Characterization of Haemophilus somnus Lipooligosaccharide". Thesis submitted to the Faculty of the Virginia Polytechnic Institute and State University in partial fulfillment of the requirements for the degree of Master of Science; Veterinary Medical Sciences, Oct. 23, 1998, Blacksburg, VA, 63 pages.

Jacques et al., "Virulence Factors of Pasteurellaceae, Formidable Animal Pathogens". ASM News, vol. 68, No. 4, Apr. 2002, 9 pages. [Accessed at newsarchive.asm.org/apr02/feature3.asp on Nov. 19, 2012].

Kania et al., "Characterization of a 78-Kilodalton Outer Membrane Protein of Haemophilus somnus" Infection and Immunity, vol. 58, No. 1, Jan. 1990, pp. 237-244.

Korczak et al., "Phylogeny of the family Pasteurellaceae based on rpoB sequences". International Journal of Systemic and Evolutionary Microbiology, vol. 54, 2004, pp. 1393-1399.

Nikaido et al., "The Outer Membrane of Gram-negative Bacteria". Advances in Microbial Physiology, vol. 20, 1979, pp. 163-250.

Ribble et al., "Efficacy of Immunization of Feedlot Calves with a Commercial Haemophilus somnus Bacterin". Canadian Journal of Veterinary Research, vol. 52, 1988, pp. 191-198.

Sandal et al., "A genomic window into the virulence of Histophilus somni". Trends in Microbiology, vol. 18, No. 2, 2010, pp. 90-99.

Sandal et al., "Characterization and Comparison of Biofilm Development by Pathogenic and Commensal Isolates of Histophilus somniÑ". Journal of Bacteriology, vol. 189, No. 22, Nov. 2007, pp. 8179-8185.

Sandal et al., "Histophilus somni biofilm formation in cardiopulmonary tissue of the bovine host following respiratory challenge". Microbes and Infection, vol. 11, 2009, pp. 254-263.

Silva et al., "The Protective Effect of Vaccination Against Experimental Pneumonia in Cattle with Haemophilus somnus Outer Membrane Antigens and Interference by Lipopolysaccharide". Canadian Journal of Veterinary Research, vol. 54, 1990, pp. 326-330.

Sylte et al. "Haemophilus somnus Induces Apoptosis in Bovine Endothelial Cells In Vitro". Infection and Immunity, vol. 69, No. 3, Mar. 2001, pp. 1650-1660.

Tagawa et al., "Antigenic Analysis of the Major Outer Membrane Protein of Haemophilus somnus with Monoclonal Antibodies". Infection and Immunity, vol. 61, No. 5, May 1993, pp. 2257-2259.

Tagawa et al., "Characterization of a Heat-Modifiable Outer Membrane Protein of Haemophilus somnus". Infection and Immunity, vol. 61, No. 5, May 1993, pp. 1750-1755.

Tagawa et al., "Immunological characterization of the major outer membrane protein of Haemophilus somnus" Veterinary Microbiology, vol. 71, 2000, pp. 245-254.

Tagawa et al., "Purification and Partial Characterization of the Major Outer Membrane Protein of Haemophilus somnus". Infection and Immunity. vol. 61, No. 1, Jan. 1993, pp. 91-96.

van der Woude et al., "Phase and Antigenic Variation in Bacteria". Clinical Microbiology Reviews, vol. 17, No. 3, Jul. 2004, pp. 581-611.

Ward et al., "A Comparative Study of Bovine and Ovine Haemophilus somnus Isolates". Canadian Journal of Veterinary Research, vol. 59, 1995, pp. 173-178.

Yarnall et al., "Isolation and Characterization of Fc Receptors from Haemophilus somnus". Scandanavian Journal of Immunology, vol. 28, 1988, pp. 129-137.

\* cited by examiner

OUTER MEMBRANE PROTEINS OF *HISTOPHILUS SOMNI* AND METHODS THEREOF

BACKGROUND OF THE INVENTION

Sequence Listing

The instant application contains a Sequence Listing which has been submitted in ASCII format via EFS-Web and is hereby incorporated by reference in its entirety. Said ASCII copy, created on May 10, 2013, is named 10-0151-SEQ-SUB.txt and is 1,835 bytes in size.

A. Field of the Invention

The present invention relates to immunological compositions of outer membrane proteins (OMPs) of *Histophilus somni* for use against respiratory infections associated with *Histophilus somni* in cattle.

B. Description of the Related Art

The Bovine Respiratory Disease Complex (BRDC) consists of multiple microbial pathogens and contributes to substantial economic loss to the cattle industry. Treatment costs including both preventative vaccination and medication following an outbreak are estimated to be near $4 billion per year (Griffin, D. 1997. Economic Impact Associated with Respiratory Disease in Beef Cattle. *Vet. Clin. North Am. Anim. Pract.* 13; p 367-377). Adding to the economic impact is the associated loss in performance observed in animals diagnosed with BRDC; with measurable losses to average daily gain, body weight at harvest, and beef quality grade (Babcock, A. H. 2010. Epidemiology of Bovine Respiratory Disease and Mortality in Commercial Feedlots. Kansas State University (doctoral dissertation). Reports on specific monetary loss associated with decreased performance vary; likely due to varying case definitions of BRDC, but are estimated between $40 (Fulton, R. W. et al. 2002. Evaluation of Health Status of Calves and the Impact on Feedlot Performances: Assessment of a Retained Ownership Program for Postweaning Calves. *Can. J. Vet. Res.* 66, 173-180) and almost $300 (Duff and Gaylean 2011. Recent Advances in Management of Highly Stressed, Newly Received Feedlot Cattle. *Journal of Animal Science.* 85; p 823-840)) per animal. The performance loss has also been shown to significantly increase with the number of times an animal requires treatment for BRDC (Fulton et al. 2002).

*Histophilus somni* (formerly *Haemophilus somnus*) has been identified as a key contributor to BRDC (Duff and Gaylean 2011). This gram-negative pleomorphic coccobacillus belonging to the family Pasteurellaceae (Korczak et al. 2004. Phylogeny of the Family Pasteurellaceae based on rpoB sequences. *International Journal of Systemic and Evolutionary Microbiology.* 54; p 1393-1399) makes up part of the normal microbiota of the upper respiratory and urogenital tracts in cattle, sheep, and other ruminants (Ward et al. 2006. *Haemophilus somnus* (*Histophilus somni*) in Bighorn Sheep. *Canadian Journal of Veterinary Research.* 70; p. 34-42). It is closely related to other bovine pathogens including *Pasteruella multocida* and *Mannheimia haemolytica* (both of which are also associated with BRDC) as well as the human pathogens *Haemophilus ducreyi* and *Haemophilus influenazae* (Challacombe et al. 2007. Complete Genome Sequence of *Haemophilus somnus* (*Histophilus somni*) strain 129Pt and Comparison to *Haemophilus ducreyi* 35000HP and *Haemophilus influenzae* Rd. *Journal of Bacteriology* 189(5); p 1890-1898).

Estimates place the isolation rate of *H. somni* from the upper respiratory tract of healthy calves as high as 50% with no clinical manifestations of disease; however animals diagnosed with BRDC have an even higher isolation rate for the bacteria (Griffin, D. 2010. Bovine Pasteurellosis and Other Bacterial Infections of the Respiratory Tract. *Veterinary Clinics of North American Food Animal Practice.* 26(1); p 57-71). Under stressful conditions or states of immunosuppression, *H. somni* may colonize the lower respiratory tract, endocardium, or central nervous system and has been identified as an etiological agent in diverse diseases such as pneumonia, endocarditis, arthritis, abortion, septicemia, and thromboembolic meningoencephalitis (TEME) (Ward et al. 2006).

At the time of slaughter, less than 15% of animals receiving proper treatment for BRDC (preventative vaccinations and appropriate antibiotics during an outbreak) show signs of lung lesions and these lesions involve less than 5% of the total lung (Griffin, D. 2010). Conversely, 50% of animals not receiving proper care display lung lesions at the time of slaughter, and these lesions may involve 15% or more of the total lung (Griffin, D. 2010). In one field study of over 10,000 animals, 459 calves (4.6%) died from disease of one form or another. Of the mortalities in the study, 279 (60.8%) were shown to be related to respiratory ailments, and of those with respiratory infections, 226 (81.0%) were associated with *H. somni* related pneumonia, pleurisy, or abscesses (Ribble et al. 1988. Efficacy of Immunization of Feedlot Cattle with a Commercial *Haemophilus somnus* bacterin. *Canadian Journal of Veterinary Research.* 52; p 191-198). While antibiotic treatment may be successful in response to an *H. somni* infection, an increasing prevalence of antibiotic resistant field isolates is of concern (Duff and Gaylean 2011). Preventative care by vaccination would be preferred as it is proactive rather than reactive and is much more cost effective.

Many *H. somni* vaccines are currently available from various animal health companies; however these vaccines are predominantly composed of killed bacterins and were licensed over thirty years ago with an aim in preventing TEME. The use of these bacterin vaccines has been effective against TEME, however has been shown to have neutral or even negative effects on respiratory disease in feedlot cattle. Negative side-effects include IgE induced anaphylactic shock and interactions when calves infected with Bovine Respiratory Syncytial Virus (BRSV) are vaccinated (Griffin, D. 2010). The decrease in prevalence of TEME and the emergence of *H. somni* related pneumonia in the US and myocarditis in Canada beginning in the late 1980's, have lead to a need for further investigation of efficacious antigens for vaccine production (O'Toole et al. 2009. Diagnostic Exercise: Myocarditis due to *Histophilus somni* in Feedlot and Backgrounded Cattle. *Veterinary Pathology.* 46; p 1015-1017).

*H. somni* related pneumonia is an economically significant condition for the beef and dairy industries. There is little evidence of field efficacy in currently available vaccines, so the need for research into next generation vaccine products is warranted.

SUMMARY OF THE INVENTION

The present invention provides immunogenic compositions, vaccines, and related methods that overcome deficiencies in the art. The compositions and methods provide outer membrane proteins (OMPs) of *Histophilus somni* for the treatment of respiratory conditions in ruminants, including but not limited to cattle, sheep and bison.

The present invention further includes immunogenic compositions and vaccines of the invention comprise OMPs of *Histophilus somni*. Immunogenic compositions of the invention which comprise at least one or more OMP *Histophilus somni* polypeptides as defined herein may further comprise a physiologically-acceptable vehicle such as a pharmaceutically or veterinary acceptable carrier, adjuvant, or combination thereof.

Any of the OMP *Histophilus somni* polypeptides provided herewith or any immunogenic compositions comprising one or more of these OMP *Histophilus somni* polypeptides provided herewith can be used as a medicament, preferably as a vaccine or immunogenic composition, most preferably for the prophylaxis or treatment of a subject against a *Histophilus somni* infection.

Two representative isolates of the OMP *Histophilus somni* polypeptides include Lg2-OK08 and LgD1-TN08, deposited with the American Type Culture Collection (ATCC), University Boulevard, Manassas, Va. 20110-2209 on Mar. 29, 2012, under the terms of the Budapest Treaty and designated as PTA-12755 and PTA-12756 respectively.

Those of skill in the art will understand that the compositions used herein may incorporate known injectable, physiologically acceptable sterile solutions. For preparing a ready-to-use solution for parenteral injection or infusion, aqueous isotonic solutions, e.g. saline or plasma protein solutions, are readily available. In addition, the immunogenic and vaccine compositions of the present invention can include veterinary-acceptable carriers, diluents, isotonic agents, stabilizers, or adjuvants.

Methods of the invention include, but are not limited to, a method of provoking an immune response against a *Histophilus somni* infection in a subject comprising the step of administering to the subject an immunogenic composition comprising one or more OMP *Histophilus somni* polypeptides as defined herein. Preferably, the immune response is provoked against more than one serotype or isolate of *Histophilus somni*. Compositions of the invention may be used to treat or alternatively to prevent a *Histophilus somni* infection. Preferably, such immune response reduces the incidence of or severity of one or more clinical signs associated with the infection with one or more *Histophilus somni* serotypes.

Herein, suitable subjects and subjects in need to which compositions of the invention may be administered include animals and humans in need of either prophylactic or treatment for a viral, microbial, parasitic, protozoan, bacterial, or fungal associated infection, disease, or condition. Preferred animals include bovine and ovine. Most preferably, an immune response is stimulated in bovine.

The invention also provides a method of reducing the incidence of or severity of one or more clinical signs associated with *Histophilus somni* infection, comprising the step of administering an immunogenic composition of the invention that comprises one or more OMP *Histophilus somni* peptides as provided herewith and preferably a carrier molecule, such that the incidence of or the severity of a clinical sign of the *Histophilus somni* infection is reduced by at least 10%, preferably at least 20%, even more preferred at least 30%, even more preferred at least 50%, even more preferred at least 70%, most preferred at least 100% relative to a subject that has not received the immunogenic composition as provided herewith. Such clinical signs include labored or rapid respiration, coughing, anorexia, depression or lethargy, nasal or ocular discharge, and mortality. According to a further aspect, the present invention also relates to a method for the prophylaxis of a *Histophilus somni* infection, comprising the step of administering an immunogenic composition of the invention that comprises one or more OMP *Histophilus somni* peptides as provided herewith.

The invention also provides a method of preparing any of the immunogenic compositions provided herewith that method comprises mixing one or more OMP *Histophilus somni* peptides as provided herewith with a carrier molecule, preferably such that the one or more OMP *Histophilus somni* peptides and carrier molecule are covalently coupled or conjugated to one another. Such conjugates may be multivalent or univalent. Multivalent compositions or vaccines include an immuno-conjugation of multiple OMP *Histophilus somni* peptides with a carrier molecule. In a further aspect, the invention provides a method of producing one or more OMP *Histophilus somni* peptides that method comprises transforming a host cell, preferably a prokaryotic cell such as *E. coli* with a nucleic acid molecule that codes for any of the *Histophilus somni* peptides as provided herewith. Alternatively, the host cell may be a eukaryotic cell such as an animal cell, protist cell, plant cell, or fungal cell. Preferably the eukaryotic cell is a mammalian cell such as CHO, BHK or COS, or a fungal cell such as *Saccharomyces cerevisiae*, or an insect cell such as Sf9.

Another aspect of the invention provides a method of producing one or more OMP *Histophilus somni* peptides that induce an immune response against *Histophilus somni*. This comprises culturing a transformed expression vector coding for and expressing one or more *Histophilus somni* peptides disclosed herein. The expressed proteins are either retained by the expression organism or secreted into the culture medium. Expression is conducted under conditions sufficient to produce an OMP *Histophilus somni* peptide a capable of inducing an immune response to *Histophilus somni*.

Methods of making compositions of the invention may further comprise admixing the conjugate of one or more OMP *Histophilus somni* peptides and a carrier molecule with a physiologically-acceptable vehicle such as a pharmaceutically- or veterinary-acceptable carrier, adjuvant, or combination thereof. Those of skill in the art will recognize that the choice of vehicle, adjuvant, or combination will be determined by the delivery route, personal preference, and animal species among others.

In another aspect, the invention provides a method of diagnosing a *Histophilus somni* infection in a subject. That method comprises providing one or more OMP *Histophilus somni* peptides; contacting the one or more OMP *Histophilus somni* peptides with a sample obtained from the subject; and identifying the subject as having a *Histophilus somni* infection if an antibody capable of binding the one or more *Histophilus somni* peptides is detected in the sample.

In another respect, the invention provides a method of ascertaining that a subject has been previously exposed to a *Histophilus somni* infection and is able to express an immune response to *Histophilus somni*. That method comprises providing one or more OMP *Histophilus somni* peptides; contacting the one or more OMP *Histophilus somni* peptides with a sample obtained from the subject; and identifying the subject as having a *Histophilus somni* infection if an antibody capable of binding the one or more OMP *Histophilus somni* peptides is detected in the sample.

The invention also provides kits that comprise an immunogenic composition that comprises one or more OMP *Histophilus somni* peptides, preferably together with a carrier molecule; a container for packaging the immunogenic composition; a set of printed instructions; and a dispenser capable of administering the immunogenic composition to an animal. Optionally, the one or more OMP *Histophilus somni* peptides and the carrier molecule may be packaged as a conjugate or as separate compounds. When supplied separately, a means of conjugating the one or more OMP *Histophilus somni* peptides and carrier molecule, as well as appropriate printed instructions, is also supplied.

The invention also provides kits for vaccinating an animal comprising a set of printed instructions; a dispenser capable of administering the immunogenic composition provided herewith comprising one or more OMP *Histophilus somni* peptides to an animal; and wherein at least one of OMP *Histophilus somni* peptides effectively immunizes the animal against at least one disease associated with *Histophilus somni* infection. Preferably, the one or more OMP *Histophilus somni* peptides are selected from those provided herewith. Kits of the invention may further comprise a veterinary acceptable carrier, adjuvant, or combination thereof.

The dispenser in a kit of the invention is capable of dispensing its contents as droplets; and the immunogenic composition comprises the OMP *Histophilus somni* peptides as provided herewith included in the kit is capable of reducing the severity of at least one clinical sign of a *Histophilus somni* infection when administered intranasally, orally, intradermally, or intramuscularly to an animal. Preferably, the severity of a clinical sign is reduced by at least 10% preferably by at least 20%, even more preferred by at least 30%, even more preferred by at least 50%, even more preferred by at least 70%, most preferred by at least 100% as compared to an untreated, infected animal.

Methods for the treatment or prophylaxis of infections related to *Histophilus somni* are also disclosed. The method comprises administering an effective amount of the immunogenic composition of the present invention to a subject, wherein said treatment or prophylaxis is selected from the group consisting of reducing signs of *Histophilus somni* infection, reducing the severity of or incidence of clinical signs of *Histophilus somni* infection, reducing the mortality of subjects from *Histophilus somni* infection, and combinations thereof.

Compositions of the invention further comprise a veterinary acceptable carrier, adjuvant, or combination thereof. Such compositions may be used as a vaccine and comprise an attenuated vaccine, an inactivated vaccine, or combinations thereof.

Those of skill in the art will understand that the compositions used herein may incorporate known injectable, physiologically acceptable sterile solutions. For preparing a ready-to-use solution for parenteral injection or infusion, aqueous isotonic solutions, e.g. saline or plasma protein solutions, are readily available. In addition, the immunogenic and vaccine compositions of the present invention can include pharmaceutical- or veterinary-acceptable carriers, diluents, isotonic agents, stabilizers, or adjuvants.

Methods of the invention may also comprise admixing a composition of the invention with a veterinary acceptable carrier, adjuvant, or combination thereof. Those of skill in the art will recognize that the choice of carrier, adjuvant, or combination will be determined by the delivery route, personal preference, and animal species among others.

The invention also provides a method of reducing the severity of a *Histophilus somni* infection in an animal comprising administrating to the animal a composition that comprises an OMP of *Histophilus somni*.

Methods for the treatment or prophylaxis of infections associated with *Histophilus somni* are also disclosed. The method comprises administering an effective amount of the immunogenic composition of the present invention to an animal, wherein said treatment or prophylaxis is selected from the group consisting of reducing signs of *Histophilus somni* infection, reducing the severity of or incidence of clinical signs of *Histophilus somni* infection, reducing the mortality of animals from *Histophilus somni* infection, and combinations thereof.

Preferred routes of administration include intranasal, oral, intradermal, and intramuscular. Administration in drinking water, most preferably in a single dose, is preferred. The skilled artisan will recognize that compositions of the invention may also be administered in two or more doses, as well as, by other routes of administration. For example, such other routes include subcutaneously, intracutaneously, intravenously, intravascularly, intraarterially, intraperitnoeally, intrathecally, intratracheally, intracutaneously, intracardially, intralobally, intramedullarly, intrapulmonarily, or intravaginally. Depending on the desired duration and effectiveness of the treatment, the compositions according to the invention may be administered once or several times, also intermittently, for instance on a daily basis for several days, weeks or months and in different dosages.

The invention also provides kits for vaccinating an animal comprising a set of printed instructions; a dispenser capable of administering a vaccine to an animal; and at least one isolate from an OMP of *Histophilus somni* that effectively immunizes the animal against at least one disease associated with *Histophilus somni*. Kits of the invention may further comprise a veterinary acceptable carrier, adjuvant, or combination thereof.

The dispenser in a kit of the invention is capable of dispensing its contents as droplets; and the isolate included in the kit is capable of reducing the severity of at least one clinical sign of a *Histophilus somni* infection when administered intranasally, orally, intradermally, or intramuscularly to an animal. In some kits, the isolate is also capable of reducing the severity of at least one clinical sign of a *Histophilus somni* infection. Preferably, the severity of a clinical sign is reduced by at least 10% as compared to an untreated, infected animal.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION

Figure 1:
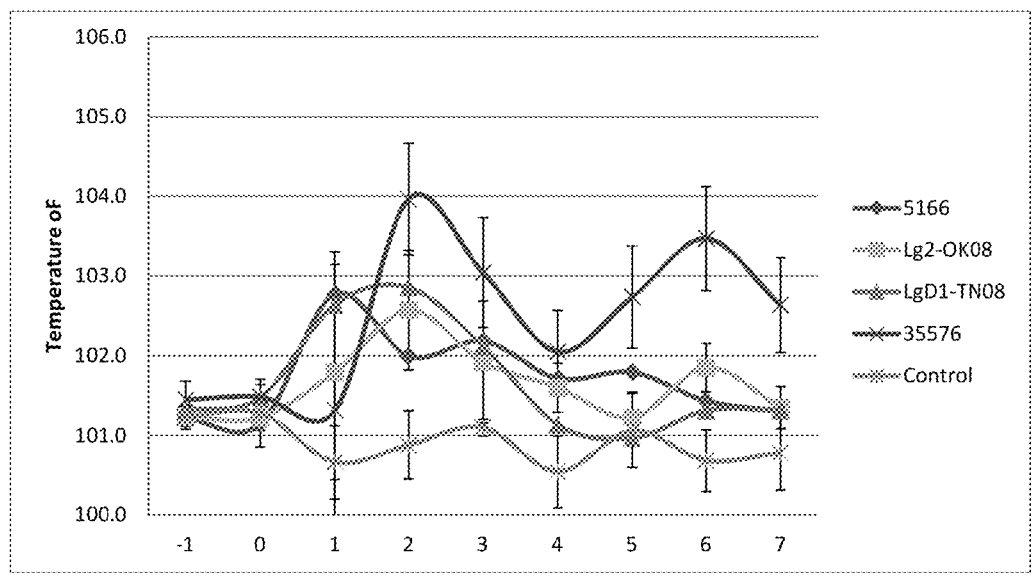
FIG. 1. is a graph illustrating mean rectal temperature by treatment group. Baseline rectal temperatures were obtained by observation both one day prior and then immediately preceding challenge on Days −1 and 0. Rectal temperatures were recorded daily following challenge and continued until final necropsy occurred on Day 7. Error bars represent confidence with $\alpha=0.1$.

The invention provides immunological compositions of OMPs of *H. somni* for use as a treatment for respiratory infections in cattle, including but not limited to two representative OMP preparations from *Histophilus somni* derived from isolates Lg2-OK08 and LgD1-TN08, deposited with the American Type Culture Collection (ATCC), 10801 University Boulevard, Manassas, Va. 20110-2209 on Mar. 29, 2012, under the terms of the Budapest Treaty and designated as PTA-12755 and PTA-12756 respectively As a gram negative bacterium, *H. somni* presents an outer membrane which is the first area of interaction between the bacteria and the host's immune system. The outer membrane of gram-negative bacteria consists of phospholipids, lipopolysaccharides (LPS), and proteins. Some estimates place the composition of the outer surface of the outer membrane at 41% LPS and 59% protein, while the inner surface is expected to contain 53% phospholipids and 47% protein (Nikaido and Nakae 1979. The Outer Membrane of Gram Negative Bacteria. *Advances in Microbial Physiology.* 20; p 163-250). The phospholipid component of the outer-membrane contains phosphatidylethanolamine, phosphatidygylcerol, and cardiolipin creating a bi-layer as is seen in other cell membranes (Nikaido and Nakae 1979).

The outer membrane of most gram negative bacteria contains endotoxic lipopolysaccharides (LPS). The external portion of the LPS plays an important role in pathogenicity and interaction with the host immune system while showing extreme variability even within a single species, and has previously been referred to as "O-antigen" (Nikaido and Nakae 1979). The O-antigens are linked to the membrane by a more conserved polysaccharide referred to as the "R-core" which consists of an 8-carbon sugar, 3-deoxyoctulosonic acid, L-glycero-D-mannoheptose, phosphate, ethanolamine phosphate, and ethanolamine pyrophosphate (Nikaido and Nakae 1979, supra). Along with the O-antigens and R-core, the LPS typically contains lipid-A. Lipid-A consists of a D-glucosaminyl-(1→6)-D-glucosamine backbone with saturated fatty acids bound by either amide or ester bonds.

The outer membrane of *H. somni* has been shown to lack certain high-molecular weight components that would constitute a true LPS, so its endotoxins are therefore referred to as lipooligosaccharides (LOS) (St. Michael et al. 2006.

Structural Analysis of the Lipooligosaccharide-derived Oligosaccharide of *Histophilus somni* (*Haemophilus somnus*) strain 8025. *Carbohydrate Research.* 341; p 281-284). The LOS of *H. somni*, like the LPS of other gram-negative bacteria, show high levels of variability in exposed structures, while membrane-associated anchor regions are more conserved (St. Michael et al. 2006).

Initial LOS purification and biochemical assays showed that the LOS of *H. somni* consists of dodecanoic, tetradecanoic, and 3-hydroxytetradecanoic fatty acids, a high proportion of hexose, 3-deoxy-D-manno-octuloonic acid (Kdo), phosphate, a small amount of heptose (L-glycero-D-mannoheptose), glucosamine, and lipid-A (Inzana et al. 1988. Purification and Characterization of Lipooligosaccharides from Four Strains of *Haemophilus somnus*. *Infection and Immunity.* 56(11); p 2830-2837). Further research has shown that *H. somni* is capable of phase-variation of its LOS resulting from differential presentation of phosphoethanolamine (PEtn), phosphocholine (ChoP), and heptose side chains (Inzana et al. 1992. Phenotypic Phase Variation in *Haemolphilus somnus* Lipoologosaccharide During Bovine Pneumonia and After in vitro Passage. *Infection and Immunity.* 60(7); p 2943-2951; Cox et al. 1998. Structural Analysis of the Phase-Variable Lipooligosacchride from *Haemolophilus somnus* strain 738. *Eur. J. Biochem.* 253; p 507-516; Elswaifi 2006. The Molecular Characterization of Phosphorylcholine (ChoP) on *Histophilus somni* Lipooligosaccharide: Contribution of ChoP to Bacterial Virulence and Pathogenesis. Virginia Polytechnic Institute and State University (doctoral dissertation); Howard et al. 2000. Antigenic Diversity of *Haemophilus somnus* Lipooligosaccharide: Phase-Variable Accessibility of the Phosphorylcholine Epitope. *Journal of Clinical Microbiology.* 28(12); p 4412-4419). This along with the incorporation of N-acetylneuraminic acid (commonly found on mammalian cell surfaces) into the outer membrane, give *H. somni* a variety of modes of host immune system evasion (Inzana et al. 2002. Incorporation of N-Acetyleneuraminic Acid into *Haemophilus somnus* Lipooligosaccharide (LOS): Enhancement of Resistance to Serum and Reduction of LOS Antibody Binding. *Infection and Immunity.* 70(9); p 4870-4879).

As a gram-negative bacterium, the components of the outer-membrane make for attractive immunologic targets. By using OMP's as the basis of vaccine candidates it may be possible to induce immune responses which selectively target surface antigens associated with virulence. Targeted immune responses generated from an OMP vaccine may interfere with *H. somni*'s ability to colonize the lower respiratory tract, inhibit the uptake of iron required for continued colonization, or limit the impact of various modes of immune evasion and interference.

While much work has been done to expand the knowledge base on the virulence mechanisms of *H. somni*, it remains unclear which OMP, or combination of OMP's, may ultimately be shown to be immunologically important. Mouse model work has shown some promise, however host animal vaccine efficacy studies are lacking in the current literature. The goals of this thesis are to establish proof-of-concept for the efficacy of OMP vaccine candidates against a respiratory challenge and compare any observed level of efficacy to currently available products.

In order to achieve this goal a challenge model capable of producing consistent lung lesion scores in control animals was established. An appropriate challenge model should produce lung lesions consistent with wild-type *H. somni* infection by producing lung lesions in ≥50% of untreated control animals with ≥15% of the total lung displaying lesions. OMP vaccine candidates, containing multiple surface exposed antigens were tested in vivo and efficacy was compared to other vaccine alternatives. These alternatives included a current killed bacterin product and modified live mutants lacking in certain biofilm formation characteristics. To monitor antibody (IgG) responses due to the vaccine candidates, an Enzyme Linked Immunosorbant Assay (ELISA) was developed for serological testing, and Sodium Dodecyl Sulfate—Polyacrylamide Gel Electrophoresis (SDS-PAGE) followed by western blot analysis was conducted to determine if specific immunoreactive proteins can be identified for further study.

These outer membrane variation mechanisms are facilitated by the complex genome of *H. somni*. Several isolates have been fully sequenced and have been found to possess genomes ranging from 2.0 Mb to 2.3 Mb in size (Challacombe et al. 2007.). By comparing known genomes of avirulent isolates to those which are virulent, a better understanding of pathogenicity can be achieved. *H. somni* isolate 129Pt was isolated from the urinary tract of a healthy animal, and is considered to be non-pathogenic. Analysis of this genome provides a good starting point for comparison to pathogenic isolates. The 129Pt genome was found to be 2.0 Mb in length with a total GC content of 37%. The isolate also contains the 5.2 kb pHS 129 plasmid. Within the circular, single chromosome genome 1,844 gene coding sequences were identified with an average open reading frame of 980 bp. The origin of replication is located at base 1926721 (Challacombe et al. 2007). In comparison with *H. ducreyi* and *H. influenzae* many of these genes were conserved, however 319 were observed to be unique to *H. somni*. These unique genes were found to be involved in LOS synthesis, carbohydrate uptake and metabolism, cation transport, amino acid metabolism, ubiquinone and menaquinone biosynthesis, cell surface adhesion, cofactor synthesis, and electron transport (Challacombe et al. 2007). These unique genes, and their subsequently expressed proteins, especially those which can be linked to the outer membrane region would be of interest to those involved in vaccine development.

Pathogenic *H. somni* isolate 2336 has been found to have a slightly larger genome (2.3 Mb) and code for several additional genes in comparison to the non-pathogenic 129Pt isolate. The additional genes have been found to code for virulence factors such as autotransporter adhesins, filamentous hemagglutinin homologs, restriction-modification (RM) systems, prophage-like sequences, and LOS synthesis proteins (Sandal and Inzana 2010. A Genomic Window into the Virulence of *Histophilus. Trends in Microbiology.* 18(2); p 90-99). Further analysis of the pathogenically important differences between the two isolates would result in a more directed approach to vaccine development.

Successful infection of the lower-respiratory tract by *Haemophilus* spp. and subsequent development of disease is facilitated by the presence of pili and adhesions (Jacques and Paradis 1998. Adhesin-Receptor Interactions in Pasteruellaceae. *FEMS Microbiol. Rev.* 22; p 45-59) and LOS (Johnson and Inzana 1986. Loss of Ciliary Activity in Organ Cultures of Rat Trachea Treated with Lipo-oligosaccharide from *Haemophilus influenzae. J. Med. Microbiol.* 22; p 265-268.). As a non-pathogenic isolate, 129Pt was found to code for 12 large adhesin molecules, but is lacking in many genes for pili and adhesins associated with colonization of mucosal surfaces by pathogenic isolates such as 2336 (Challacombe et al. 2007). Pili genes, which can also account for secretion mechanisms, are found in pathogenic isolates. These genes include pilA, B, C, and D (Sandal and Inzana 2010).

The genome of virulent *H. somni* isolates, such as 2336, also allow for antigenic phase variation of the LOS by slipped-strand mispairing of a 5'-CAAT-3' variable number tandem repeat (VNTR). This phase variation is not observed in isolate 129Pt. These VNTR's are located downstream from start codons or within open reading frames (ORF's) for glycosyltransferases. This translational modification is observed in the lob2ABCD genes and allows the bacteria to change its LOS presentation to evade host immune responses. The presence of N-acetyl-5-neuraminic acid (Neu5Ac) in the LOS also allows the bacteria to disguise itself from the immune response as Neu5Ac is common on the surfaces of the host's own cells (Sandal and Inzana 2010).

The lic1ABCD operon has been studied further and has been shown along with the glpQ gene to control phase variation of phosphorylcholine (ChoP) which is expressed on the LOS of *H. somni*. A similar slipped-strand mispairing occurs along a tandem repeat 5'-AACC-3' in the lic1A gene and results in various elongations and truncations and shifts the ORF out of alignment with the start codon. The variation of this kinase does not appear to affect the operation of the lic1BCD genes downstream, but does offer another variation in surface presentation to evade host defenses. ChoP was also shown to be a contributing factor to respiratory colonization by *H. somni*, however appeared to interfere with colonization during a systemic infection (Elswaifi 2006). Finally ChoP has been shown to aggregate bovine platelets through interaction with platelet activating factor receptors (PAF-R) (Elswaifi 2006).

Work concerning the ability of pathogenic isolates of *H. somni* to incorporate Neu5Ac into the LOS also sheds light on another mechanism of virulence (Inzana et al. 2002). By doing so the bacteria mimics the lacto-N-neotetraose that coats bovine endothelial cells and allows another method of immune system evasion (Sandal and Inzana 2010). The variation of ChoP and incorporation of Neu5Ac have been shown to interfere with antibody binding, even with monoclonal antibodies specific for purified *H. somni* LOS and also inhibits killing by convalescent phase serum (Sandal and Inzana 2010).

Furthermore, *H. somni* has been shown to produce biofilms in vitro and is suspected to do so in vivo although this is difficult to examine due to a rapid artificial selection against the biofilm phenotype by typical laboratory growth methods and inaccuracies in using non-host models (Sandal and others 2009). Many bacteria form biofilms through a combination of exopolysaccharides (EPS) and fimbriae to adhere to cell surfaces and each other (Costerton 1999). The bacterium uses the biofilm formation to maintain cell adhesion and to protect itself against harsh environmental conditions. The film itself may consist of up to 90% EPS, thus shielding the bacteria from immune detection and response (Costerton 1999). The biofilm formed by *H. somni* has been shown by scanning electron microscopy (SEM) and fluorescent in situ hybridization (FISH) to be more organized and extensive in vivo than other members of the Pasteurllaceae family (Sandal and others 2009). Modifying this characteristic may be an attractive approach to a modified live vaccine.

Strategies for new vaccines may also target proteins present in the outer membrane. Several of these OMPs have been characterized and some have been found to be immunoreactive with host serum (Sandal and Inzana 2010). OMPs allow the bacteria to interact with its external environment, and while some are highly conserved across several species, many are species specific. OMPs may confer motility in the form of flagellar or cilliary structures, can allow for metabolite or waste transfer across the membrane, may facilitate host cell adhesion, or may allow other binding characteristics important in immune evasion (Challacombe and others 2007).

Isolation of OMPs has been achieved by disruption of the bacterial cells from a pure culture by lysis with detergent, organic solvents, osmotic shock, or repeated freeze thaws followed by a low speed centrifugation to remove cell debris (Bollag and others 1996). The supernatant containing the OMPs is then subjected to ultracentrifugation removing all insoluble components. The resultant pellet is then suspended and incubated in a 10 mM HEPES buffer with 2% (wt/vol) N-lauroyl sarcosine (sarcosyl) and subjected to another round of ultracentrifugation (Hobb and others 2009). The resultant pellet may otherwise be solubilized with sodium dodecyl sulfate (SDS), 3-(N-morpholino) propanesulfonic acid (MOPS), Tris, or Phosphate buffers, chaotropic rhodanide salts, or urea and subsequently purified by a method appropriate for the proteins of interest (Rehm 2006). Immunoreactivity is then examined through use of convalescent phase serum in a Western Blot (Kania and others 1990).

One of the first potential immunologically important proteins to be described this way is a 78-kDa protein that was shown to be conserved in a majority of isolates tested, including isolates obtained from various disease states, as well as non-pathogenic isolates (Kania and others 1990). Another OMP of 40-kDa size was subsequently isolated from TEME associated *H. somni* isolate 8025 and subjected to N-terminal sequencing. This protein was found to have high homology to porin proteins found in both *H. influenzae* and *E. coli* (Tagawa and others 1993a). Porin proteins have been shown to facilitate low-molecular-mass diffusion of solutes across the membrane. An OMP with a heat modifiable molecular weight was also identified with a molecular weight of 28-37 kDa dependent upon whether the protein was solubilized at 60° C. or 100° C. This protein was shown by N-terminal sequencing to be homologous to the OmpA proteins of other gram-negative bacteria, including *E. coli* and *Actinobacillus actinomycetemcomitans* (Tagawa and others 1993b).

Further research looked to compare the predominant OMPs of 53 isolates of *H. somni* to determine if classification of pathogenicity could be accomplished by protein profile. This study showed a large variation in OMP molecular weights and was able to classify the isolates tested into 4 distinct groups and 3 subgroups. These classifications however did not correspond to disease states associated with the different isolates. The molecular mass variation of the OMPs is of interest as the predominant OMP identified in this study shows N-terminal homology to the P2 protein associated with pathogenicity in *H. influenzae* (Tagawa and others 2000).

The ability of *H. somni* to acquire iron from its host is also an important process for successful infection and differences in transferrin binding OMPs may account for host specificity and virulence. Many members of the family Pasteurellaceae utilize a receptor complex composed of two OMP's, transferrin binding proteins A and B, to acquire transferrin bound iron from the host (Ekins and others 2004). The operon responsible for Tbp is arranged such that TbpB precedes TbpA and is typically controlled by a repression mechanism involving ferric uptake regulator (Fur) proteins in the presence of available iron. Allelic differences in the tbpA gene result in different transferrin binding mechanisms that have been linked to virulent and non-virulent isolates (Ekins and others 2004). The presence of the tbpA2 allele results in a single-component TbpA receptor as was noted for isolate 129Pt while a combination of tbpA and tbpB genes encodes for a bipartite receptor complex identified in pathogenic *H. somni* isolates 2336 and 649 (Tremblay and others 2006).

The fhaB gene, present in only pathogenic isolates of *H. somni*, encodes for an immunoglobulin binding protein (IbpA). Isolate 2336 encodes for four separate fhaB homologs at four different loci. The IbpA protein is a large exoprotein associated in the inhibition of phagocytosis by the host immune system (Sandal and Inzana 2010). IbpA interacts with the Fc portion of IgG1, IgG2, and IgM and has been described as a 350 kDa protein with subunits of 270, 120, and 41 kDa sizes. The 41 kDa subunit is the only portion shown to react with bovine IgG1 (Yarnall and others 1988).

Recent research has elucidated the importance of post-translational modification of host cell proteins by bacterial secretions as a mechanism of virulence and host immune response evasion. AMPylation is a reversible process of covalently adding adenosine monophosphate (AMP) to a hydroxyl protein side-chain from threonine and tyrosine residues (Woolery and others 2010). The adenylyltransferase enzymes that facilitate this process contain a filamentation induced by cAMP (Fic) domain (HPFx (D/E) GN (G/K) R) that is widely conserved across all species (Xiao and others 2010). Fic domains are seen naturally in eukaryotic cells and often play a role in cell signaling (Roy and Mukherjee 2009). Fic domain containing proteins from prokaryotes however, appear to inhibit the function of Rho dependent GTPases in the host cells (Worby and others 2009).

The IbpA of virulent *H. somni* isolates contains two consecutive Fic domains near the C-terminus (Roy and Mukherje 2009) and an adhesin domain at the N-terminus (Woolery and others 2010). It appears that this protein is secreted by the bacteria into host cells resulting in the AMPylation of host cell GTPases and modification of the actin cytoskeleton (Woolery and others 2010). Adenylation occurs at the switch1 tyrosine residue in association with RhoA, Rac1, or Cdc42 as a substrate (Xiao and others 2010). This mechanism is also seen with the VopS protein from *Vibrio parahaemolyticus* which AMPylates a threonine residue instead. These modifications lead to an interference with the macrophage's ability to conduct phagocytosis, phagosome trafficking, transcriptional activation of immune effectors, stimulation of adaptive responses, and apoptosis (Chimini and Chavrier 2000). IbpA Fic domain induced cytotoxicity was observed only in pathogenic isolates such as 2336 and was not seen in non-pathogenic isolates such as 129Pt (Zeckarias and others 2011).

Work has been done to test IbpA subunit vaccine prototypes with mixed results. The use of pET41a and pET-GSTx to produce recombinant IbpA subunits A3, A5, and DR2 ($2^{nd}$ Fic domain) in *E. coli* was successful in preventing *H. somni* induced septicemia following vaccination of 5-6 week old NIH Swiss Webster mice with the recombinant subunits (Geertsema and others 2008). The IbpA DR2 subunit was also reported to show protection against a respiratory challenge with *H. somni* in 5-week-old Holstein calves when administered in two doses spread three weeks apart (Geertsema and others 2011). The ability to extrapolate data from this study to a large population is weak due to small treatment groups (5-6 animals each). While the DR2 vaccinated group did display a statistically significant decrease in total lung pathology when compared to the control group (p=0.04), this decrease may not be biologically significant as the control animals displayed only 11% lung pathology. Unpublished data from a larger Boehringer Ingelheim Vetmedica, Inc. study testing the DR2 subunit could not confirm these results.

Vaccination Strategies

Successful vaccination induces immunologic memory within the host allowing for expedited, targeted response to subsequent infections. There are several strategies to accomplish this, and each has its unique advantages and disadvantages. Current technologies for vaccination against bacterial infections include the use of killed bacterins, modified live mutants, and protein based vaccines.

Proliferation of memory cells with antigenic specificity to neutralizing epitopes of bacterial toxins and cell surface proteins embedded in the gram negative cell wall are the main goal of vaccination. When subsequent infections are more easily tolerated and successfully cleared by individual hosts, herd immunity is improved. While the pathogenic organism may still cause minor issues within individual animals, it is far less likely that widespread economic loss will be observed when appropriate vaccines are administered.

The quickest way to ensure a vaccine includes all possible virulence-related antigens present on a cell surface is to use a killed bacterin. These products, however, can induce anaphylactic reactions depending on production methods and the sensitivity of the individual animal, and in combination products containing multiple organisms, these events are more likely (Roth, 2007). The benefit of these products typically outweighs this risk as these vaccines have proven useful in the prevention of disease for cattle operations and are typically the most cost-effective means of controlling disease outbreaks (Babiuk, 1994).

Facilitated attenuation of virulent isolates, or isolation of naturally avirulent isolates, lead to lower development costs, while simplicity of production process decreases overhead allowing manufacturers to provide products at lower prices to consumers. It is difficult however for companies to ensure the longevity of their products as wild-type mutations or other conditions in the field may decrease the effectiveness of these products over time.

Efficacy issues arise when the antigens present in the vaccine do not confer immunity to wild-type live isolates. In the case of *H. somni* vaccines, it has been shown that certain surface and culture supernatant proteins that are produced in vivo are not adequately represented in vitro during vaccine production (Griffin 2010). Some of these proteins are suspected to be immunologically significant, and work is ongoing to determine if various growth methods, protein purification strategies, or gene knockout mutant isolates may improve vaccine efficacy (Tagawa, 1993; Sandal, 2009; Zekarias, 2010). Without new vaccine isolates, improvement could be made through the use of various adjuvant platforms.

In a killed bacterin vaccine, since no living pathogen is introduced, adjuvants are incorporated to increase the immune response to important antigens. Adjuvants currently used in veterinary vaccines include aluminum salts (alum), oil emulsion, saponin, immune-stimulating complexes (ISCOMs), liposomes, microparticles, nonionic block copolymers, derivatized polysaccharides, cytokines, and bacterial derivatives (Spickler, 2003). Each adjuvant has its own set of properties that determine its mode of action, which in turn can influence the type of immune response elicited.

Particulate adjuvants (i.e., alum) serve to improve the action of antigen presenting cells by forming aggregates that are more easily phagocytosed (Spickler, 2003). Aluminum hydroxide is used as the adjuvant system for several commercially available *H. somni* vaccines including Pfizer's Sommubac and BIVI's Elite-9 HS. While adjuvant formulations are proprietary and many actual mechanisms of action are unknown, the general theory for this type of adjuvant would be induction of a Major Histocompatibility Complex, Type II (MHC II) antibody mediated response (Murphy, 2008).

Oil emulsion adjuvants would aid in the induction of MHC II response, reportedly due to a "depot effect" by holding the antigens in place at the injection site, allowing more antigen presenting cells to encounter the important antigens over an extended period of time (Spickler, 2003). While there are no products that currently use this type of adjuvant commercially for vaccination against *H. somni*, oil based Rehydragel® aluminum hydroxide gel (commercially available from Reheis Inc.) is used in Clostridial vaccines which can be combined with *H. somni* in a combination product, and Freund's adjuvant is regularly used in research studies as an initial adjuvant with which to test proof-of-concept for new vaccine candidates (Babiuk, 1994).

As *H. somni* is an extracellular bacterial pathogen, adjuvants capable of enhancement of the induction of IgG production by plasma cells, activation of the complement system, and endotoxin neutralization would be beneficial. For this reason aluminum salts and oil-in-water emulsions are typically used. However these adjuvants tend to be weak in comparison to newer technologies, but are still widely used as they have been approved by the regulatory agencies for use in veterinary vaccines and pose no threat of systemic toxicity (Aguilar and Rodriguez 2007).

Vaccination using avirulent modified live organisms does not require the use of adjuvants, and has been shown more capable of producing cell-mediated as well as antibody driven immune responses (Detmer and Glenting 2006). These products tend to reduce the prevalence of anaphylactic reactions as well. However, development of attenuated isolates or targeted deletion mutants can be very expensive and another major risk is associated. These live organisms behave just like their wild-type counterparts and maintain their ability to exchange genetic information with other isolates within the animal. Due to this genetic recombination, avirulent vaccine isolates can incorporate virulence factors and revert to a virulent form. These organisms can be shed and spread just like any other isolate, which is beneficial to herd immunity if they remain avirulent, but can cause serious outbreak issues if a reversion occurs (Detmer and Glenting 2006). Vaccines of this type must undergo extensive safety studies to decrease these concerns prior to regulatory approval, however the possibility remains.

Acellular, protein based vaccines remove the concerns of virulent reversions seen in modified live vaccines while continuing to decrease the incidence of anaphylaxis seen in bacterin products. Vaccines of this type would be expected to work in much the same way as a killed bacterin, and could be combined with similar adjuvants to induce MHCII and antibody mediated immunity. These preparations result in a higher concentration of immunologically important proteins delivered via vaccination and may therefore produce a more directed immune response. Development costs can be high, however with the appropriate recombinant expression system production costs can remain low. The key to this type of vaccine is to introduce important epitopes of virulence related proteins which induce immune responses directed at decreasing the ability of a wild-type infection to take hold (Babiuk 1994).

The practice of the present invention will employ, unless otherwise indicated, conventional techniques of molecular biology, microbiology, recombinant DNA technology, protein chemistry and immunology, which are within the skill of the art. Such techniques are explained fully in the literature. See, e.g., Sambrook, Fritsch & Maniatis, Molecular Cloning: A Laboratory Manual, Vols. I, II and III, Second Edition (1989); DNA Cloning, Vols. I and II (D. N. Glover ed. 1985); Oligonucleotide Synthesis (M. J. Gait ed. 1984); Nucleic Acid Hybridization (B. D. Hames & S. J. Higgins eds. 1984); Animal Cell Culture (R. K. Freshney ed. 1986); Immobilized Cells and Enzymes (IRL press, 1986); Perbal, B., A Practical Guide to Molecular Cloning (1984); the series, Methods In Enzymology (S. Colowick and N. Kaplan eds., Academic Press, Inc.); Protein purification methods—a practical approach (E. L. V. Harris and S. Angal, eds., IRL Press at Oxford University Press); and Handbook of Experimental Immunology, Vols. I-IV (D. M. Weir and C. C. Blackwell eds., 1986, Blackwell Scientific Publications).

Before describing the present invention in detail, it is to be understood that this invention is not limited to particular DNA, polypeptide sequences or process parameters as such may, of course, vary. It is also to be understood that the terminology used herein is for the purpose of describing particular embodiments of the invention only, and is not intended to be limiting. It must be noted that, as used in this specification and the appended claims, the singular forms "a", "an" and "the" include plural referents unless the content clearly dictates otherwise. Thus, for example, reference to "an antigen" includes a mixture of two or more antigens, reference to "an excipient" includes mixtures of two or more excipients, and the like.

A. DEFINITIONS

Unless defined otherwise, all technical and scientific terms used herein have the same meaning as is commonly understood by one of skill in the art to which this invention belongs at the time of filing. The meaning and scope of terms should be clear; however, in the event of any latent ambiguity, definitions provided herein take precedent over any dictionary or extrinsic definition. Further, unless otherwise required by context, singular terms shall include pluralities and plural terms shall include the singular. Herein, the use of "or" means "and/or" unless stated otherwise. Furthermore, the use of the term "including", as well as other forms such as "includes" and "included" is not limiting. All patents and publications referred to herein are incorporated by reference herein.

"Protection against disease", "protective immunity", "functional immunity" and similar phrases, means a response against a disease or condition generated by administration of one or more therapeutic compositions of the invention, or a combination thereof, that results in fewer deleterious effects than would be expected in a non-immunized subject that has been exposed to disease or infection. That is, the severity of the deleterious effects of the infection are lessened in a vaccinated subject. Infection may be reduced, slowed, or possibly fully prevented, in a vaccinated subject. Herein, where complete prevention of infection is meant, it is specifically stated. If complete prevention is not stated then the term includes partial prevention.

Herein, "reduction of the incidence and/or severity of clinical signs" or "reduction of clinical symptoms" means, but is not limited to, reducing the number of infected subjects in a group, reducing or eliminating the number of subjects exhibiting clinical signs of infection, or reducing the severity of any clinical signs that are present in one or more subjects, in comparison to wild-type infection. For example, it should refer to any reduction of pathogen load, pathogen shedding, reduction in pathogen transmission, or reduction of any clinical sign Preferably these clinical signs are reduced in one or more subjects receiving the therapeutic composition of the present invention by at least 10% in comparison to subjects not receiving the composition and that become infected. More preferably clinical signs are reduced in subjects receiving a composition of the present invention by at least 20%, preferably by at least 30%, more preferably by at least 40%, and even more preferably by at least 50%.

The term "increased protection" herein means, but is not limited to, a statistically significant reduction of one or more clinical symptoms which are associated with infection by an infectious agent, preferably an *H. somnus* respectively, in a vaccinated group of subjects vs. a non-vaccinated control group of subjects. The term "statistically significant reduction of clinical symptoms" means, but is not limited to, the frequency in the incidence of at least one clinical symptom in the vaccinated group of subjects is at least 10%, preferably 20%, more preferably 30%, even more preferably 50%, and even more preferably 70% lower than in the non-vaccinated control group after the challenge the infectious agent.

"Long-lasting protection" shall refer to "improved efficacy" that persists for at least 3 weeks, but more preferably at least 3 months, still more preferably at least 6 months. In the case of livestock, it is most preferred that the long lasting protection shall persist until the average age at which animals are marketed for meat.

An "immunogenic or immunological composition" refers to a composition of matter that comprises at least one OMP of *H. somni*, or immunogenic portion thereof, that elicits an immunological response in the host of a cellular or antibody-mediated immune response to the composition. In a preferred embodiment of the present invention, an immunogenic composition induces an immune response and, more preferably, confers protective immunity against one or more of the clinical signs of a *Histophilus somni* infection.

An "immunogenic" or "antigen" as used herein refer to a polypeptide or protein that elicits an immunological response as described herein. An "immunogenic" *Histophilus somni* protein or polypeptide includes the full-length sequence of any of the OMP *Histophilus somni* identified herein or analogs or immunogenic fragments thereof. The term "immunogenic fragment" or "immunogenic portion" refers to a fragment or truncated and/or substituted form of an OMP *Histophilus somni* that includes one or more epitopes and thus elicits the immunological response described herein. In general, such truncated and/or substituted forms, or fragments will comprise at least six contiguous amino acids from the full-length OMP *Histophilus somni* protein. More preferably, the truncated or substituted forms, or fragments will have at least 10, more preferably at least 15, and still more preferably at least 19 contiguous amino acids from the full-length OMP *Histophilus somni* protein. Such fragments can be identified using any number of epitope mapping techniques, well known in the art. See, e.g., Epitope Mapping Protocols in Methods in Molecular Biology, Vol. 66 (Glenn E. Morris, Ed., 1996) Humana Press, Totowa, N.J. For example, linear epitopes may be determined by concurrently synthesizing large numbers of peptides on solid supports, the peptides corresponding to portions of the protein molecule, and reacting the peptides with antibodies while the peptides are still attached to the supports. Such techniques are known and described in the art, see e.g., U.S. Pat. No. 4,708,871; Geysen et al. (1984) Proc. Natl. Acad. Sci. USA 81:3998-4002; and Geysen et al. (1986) Molec. Immunol. 23:709-715. Similarly, conformational epitopes are readily identified by determining spatial conformation of amino acids such as by, e.g., x-ray crystallography and two-dimensional nuclear magnetic resonance. See Epitope Mapping Protocols, supra. Synthetic antigens are also included within the definition, for example, polyepitopes, flanking epitopes, and other recombinant or synthetically derived antigens. See, e.g., Bergmann et al. (1993) Eur. J. Immunol. 23:2777-2781; Bergmann et al. (1996), J. Immunol. 157:3242-3249; Suhrbier, A. (1997), Immunol. and Cell Biol. 75:402-408; and Gardner et al., (1998) 12th World AIDS Conference, Geneva, Switzerland, Jun. 28-Jul. 3, 1998. (The teachings and content of which are all incorporated by reference herein.)

An "immune response" or "immunological response" means, but is not limited to, the development of a cellular and/or antibody-mediated immune response to the composition or vaccine of interest. Usually, an immune or immunological response includes, but is not limited to, one or more of the following effects: the production or activation of antibodies, B cells, helper T cells, suppressor T cells, and/or cytotoxic T cells, directed specifically to an antigen or antigens included in the composition or vaccine of interest. Preferably, the host will display either a therapeutic or a protective immunological (memory) response such that resistance to new infection will be enhanced and/or the clinical severity of the disease reduced. Such protection will be demonstrated by either a reduction in number of symptoms, severity of symptoms, or the lack of one or more of the symptoms associated with the infection of the pathogen, a delay in the of onset of viremia, reduced viral persistence, a reduction in the overall viral load and/or a reduction of viral excretion.

Herein, "specifically immunoreactive" refers to an immunoreactive protein or polypeptide that recognizes an antigen characteristic of *Histophilus somni* infection but does not react with an antigen characteristic of a strict challenge control.

As used herein, "a pharmaceutical- or veterinary-acceptable carrier" includes any and all solvents, dispersion media, coatings, adjuvants, stabilizing agents, diluents, preservatives, antibacterial and antifungal agents, isotonic agents, adsorption delaying agents, and the like. In some preferred embodiments, and especially those that include lyophilized immunogenic compositions, stabilizing agents for use in the present invention include stabilizers for lyophilization or freeze-drying.

In some embodiments, the immunogenic composition of the present invention contains an adjuvant. "Adjuvants" as used herein, can include aluminum hydroxide and aluminum phosphate, saponins e.g., Quil A, QS-21 (Cambridge Biotech Inc., Cambridge Mass.), GPI-0100 (Galenica Pharmaceuticals, Inc., Birmingham, Ala.), water-in-oil emulsion, oil-in-water emulsion, water-in-oil-in-water emulsion. The emulsion can be based in particular on light liquid paraffin oil (European Pharmacopea type); isoprenoid oil such as squalane or squalene; oil resulting from the oligomerization of alkenes, in particular of isobutene or decene; esters of acids or of alcohols containing a linear alkyl group, more particularly plant oils, ethyl oleate, propylene glycol di-(caprylate/caprate), glyceryl tri-(caprylate/caprate) or propylene glycol dioleate; esters of branched fatty acids or alcohols, in particular isostearic acid esters. The oil is used in combination with emulsifiers to form the emulsion. The emulsifiers are preferably nonionic surfactants, in particular esters of sorbitan, of mannide (e.g. anhydromannitol oleate), of glycol, of polyglycerol, of propylene glycol and of oleic, isostearic, ricinoleic or hydroxystearic acid, which are optionally ethoxylated, and polyoxypropylene-polyoxyethylene copolymer blocks, in particular the Pluronic products, especially L121. See Hunter et al., The Theory and Practical Application of Adjuvants (Ed. Stewart-Tull, D. E. S.), John-Wiley and Sons, NY, pp 51-94 (1995) and Todd et al., Vaccine 15:564-570 (1997). Exemplary adjuvants are the SPT emulsion described on page 147 of "Vaccine Design, The Subunit and Adjuvant Approach" edited by M. Powell and M. Newman, Plenum Press, 1995, and the emulsion MF59 described on page 183 of this same book.

A further instance of an adjuvant is a compound chosen from the polymers of acrylic or methacrylic acid and the copolymers of maleic anhydride and alkenyl derivative. Advantageous adjuvant compounds are the polymers of acrylic or methacrylic acid which are cross-linked, especially with polyalkenyl ethers of sugars or polyalcohols. These compounds are known by the term carbomer (Phameuropa Vol. 8, No. 2, June 1996). Persons skilled in the art can also refer to U.S. Pat. No. 2,909,462 which describes such acrylic polymers cross-linked with a polyhydroxylated compound having at least 3 hydroxyl groups, preferably not more than 8, the hydrogen atoms of at least three hydroxyls being replaced by unsaturated aliphatic radicals having at least 2 carbon atoms. The preferred radicals are those containing from 2 to 4 carbon atoms, e.g. vinyls, allyls and other ethylenically unsaturated groups. The unsaturated radicals may themselves contain other substituents, such as methyl. The products sold under the name Carbopol; (BF Goodrich, Ohio, USA) are particularly appropriate. They are cross-linked with an allyl sucrose or with allyl pentaerythritol. Among then, there may be mentioned Carbopol 974P, 934P and 971P. Most preferred is the use of Cabopol 971P. Among the copolymers of maleic anhydride and alkenyl derivative, are the copolymers EMA (Monsanto), which are copolymers of maleic anhydride and ethylene. The dissolution of these polymers in water leads to an acid solution that will be neutralized, preferably to physiological pH, in order to give the adjuvant solution into which the immunogenic, immunological or vaccine composition itself will be incorporated.

Further suitable adjuvants include, but are not limited to, the RIBI adjuvant system (Ribi Inc.), Block co-polymer (CytRx, Atlanta Ga.), SAF-M (Chiron, Emeryville Calif.), monophosphoryl lipid A, Avridine lipid-amine adjuvant, heat-labile enterotoxin from *E. coli* (recombinant or otherwise), cholera toxin, IMS 1314 or muramyl dipeptide, or naturally occurring or recombinant cytokines or analogs thereof or stimulants of endogenous cytokine release, among many others.

It is expected that an adjuvant can be added in an amount of about 100 μg to about 10 mg per dose, preferably in an amount of about 100 μg to about 10 mg per dose, more preferably in an amount of about 500 μg to about 5 mg per dose, even more preferably in an amount of about 750 μg to about 2.5 mg per dose, and most preferably in an amount of about 1 mg per dose. Alternatively, the adjuvant may be at a concentration of about 0.01 to 50%, preferably at a concentration of about 2% to 30%, more preferably at a concentration of about 5% to 25%, still more preferably at a concentration of about 7% to 22%, and most preferably at a concentration of 10% to 20% by volume of the final product.

"Diluents" can include water, saline, dextrose, ethanol, glycerol, and the like. Isotonic agents can include sodium chloride, dextrose, mannitol, sorbitol, and lactose, among others. Stabilizers include albumin and alkali salts of ethylendiamintetracetic acid, among others.

"Isolated" means altered "by the hand of man" from its natural state, i.e., if it occurs in nature, it has been changed or removed from its original environment, or both. For example, a polynucleotide or polypeptide naturally present in a living organism is not "isolated," but the same polynucleotide or polypeptide separated from the coexisting materials of its natural state is "isolated", as the term is employed herein.

"Safety" refers to the absence of adverse consequences in a vaccinated animal following vaccination, including but not limited to: potential reversion of a bacterium-based vaccine to virulence, clinically significant side effects such as persistent, systemic illness or unacceptable inflammation at the site of vaccine administration.

The terms "vaccination" or "*Histophilus somni*" or variants thereof, as used herein means, but is not limited to, a process which includes the administration of an immunogenic composition of the invention that, when administered to an animal, elicits, or is able to elicit—directly or indirectly—, an immune response in the animal against *Histophilus somni.*

"Mortality", in the context of the present invention, refers to death associated with by *Histophilus somni* infection, and includes the situation where the infection is so severe that an animal is euthanized to prevent suffering and provide a humane ending to its life.

"Attenuation" means reducing the virulence of a pathogen. In the present invention "attenuation" is synonymous with "avirulent". In the present invention, an attenuated bacterium is one in which the virulence has been reduced so that it does not cause clinical signs of a *Histophilus somni* infection but is capable of inducing an immune response in the target mammal, but may also mean that the clinical signs are reduced in incidence or severity in animals infected with the attenuated *Histophilus somni* in comparison with a "control group" of animals infected with non-attenuated *Histophilus somni* and not receiving the attenuated bacterium. In this context, the term "reduce/reduced" means a reduction of at least 10%, preferably 25%, even more preferably 50%, still more preferably 60%, even more preferably 70%, still more preferably 80%, even more preferably 90% and most preferably of 100% as compared to the control group as defined above. Thus, an attenuated, avirulent *Histophilus somni* isolate is one that suitable for incorporation into an immunogenic composition comprising a modified live *Histophilus somni* bacterium.

Herein, "effective dose" means, but is not limited to, an amount of antigen that elicits, or is able to elicit, an immune response that yields a reduction of clinical symptoms in an animal to which the antigen is administered.

As used herein, the term "effective amount" means, in the context of a composition, an amount of an immunogenic composition capable of inducing an immune response that reduces the incidence of or lessens the severity of infection or incident of disease in an animal. Particularly, an effective amount refers to colony forming units (CFU) per dose. Alternatively, in the context of a therapy, the term "effective amount" refers to the amount of a therapy which is sufficient to reduce or ameliorate the severity or duration of a disease or disorder, or one or more symptoms thereof, prevent the advancement of a disease or disorder, cause the regression of a disease or disorder, prevent the recurrence, development, onset, or progression of one or more symptoms associated with a disease or disorder, or enhance or improve the prophylaxis or treatment of another therapy or therapeutic agent.

The term "fragment" refers to a fragment or truncated and/or substituted form of an OMP of *Histophilus somni* or a gene coding for such OMP peptide that includes one or more epitopes and thus elicits the immunological response against *Histophilus somni*. Preferably, such fragment is a fragment or truncated and/or substituted form of any of the *Histophilus somni* peptides or any of the *Histophilus somni* genes provided herewith. In general, such truncated and/or substituted forms, or fragments will comprise at least six contiguous amino acids from the full-length sequence. More preferably, the truncated or substituted forms, or fragments will have at least 10, more preferably at least 15, and still more preferably at least 19 contiguous amino acids from the full-length sequence. Such fragments can be identified using any number of epitope mapping techniques, well known in the art. See, e.g., Epitope Mapping Protocols in Methods in Molecular Biology, Vol. 66 (Glenn E. Morris, Ed., 1996) Humana Press, Totowa, N.J. For example, linear epitopes may be determined by concurrently synthesizing large numbers of peptides on solid supports, the peptides corresponding to portions of the protein molecule, and reacting the peptides with antibodies while the peptides are still attached to the supports. Such techniques are known and described in the art, see e.g., U.S. Pat. No. 4,708,871; Geysen et al. (1984) Proc. Natl. Acad. Sci. USA 81:3998-4002; and Geysen et al. (1986) Molec. Immunol. 23:709-715. Similarly, conformational epitopes are readily identified by determining spatial conformation of amino acids such as by, e.g., x-ray crystallography and two-dimensional nuclear magnetic resonance. See Epitope Mapping Protocols, supra. Synthetic antigens are also included within the definition, for example, polyepitopes, flanking epitopes, and other recombinant or synthetically derived antigens. See, e.g., Bergmann et al. (1993) Eur. J. Immunol. 23:2777-2781; Bergmann et al. (1996), J. Immunol. 157:3242-3249; Suhrbier, A. (1997), Immunol. and Cell Biol. 75:402-408; and Gardner et al., (1998) 12th World AIDS Conference, Geneva, Switzerland, Jun. 28-Jul. 3, 1998. (The teachings and content of which are all incorporated by reference herein.)

The term "immunoreactive to *Histophilus somni*" as used herein means that the peptide or fragment elicits the immunological response against *Histophilus somni*.

"Sequence homology", as used herein, refers to a method of determining the relatedness of two sequences. To determine sequence homology, two or more sequences are optimally aligned, and gaps are introduced if necessary. However, in contrast to "sequence identity", conservative amino acid substitutions are counted as a match when determining sequence homology. In other words, to obtain a polypeptide or polynucleotide having 95% sequence homology with a reference sequence, 85%, preferably 90%, even more preferably 95% of the amino acid residues or nucleotides in the reference sequence must match or comprise a conservative substitution with another amino acid or nucleotide, or a number of amino acids or nucleotides up to 15%, preferably up to 10%, even more preferably up to 5% of the total amino acid residues or nucleotides, not including conservative substitutions, in the reference sequence may be inserted into the reference sequence. Preferably the homolog sequence comprises at least a stretch of 50, even more preferred of 100, even more preferred of 250, even more preferred of 500 nucleotides.

A "conservative substitution" refers to the substitution of an amino acid residue or nucleotide with another amino acid residue or nucleotide having similar characteristics or properties including size, hydrophobicity, etc., such that the overall functionality does not change significantly.

"Sequence Identity" as it is known in the art refers to a relationship between two or more polypeptide sequences or two or more polynucleotide sequences, namely a reference sequence and a given sequence to be compared with the reference sequence. Sequence identity is determined by comparing the given sequence to the reference sequence after the sequences have been optimally aligned to produce the highest degree of sequence similarity, as determined by the match between strings of such sequences. Upon such alignment, sequence identity is ascertained on a position-by-position basis, e.g., the sequences are "identical" at a particular position if at that position, the nucleotides or amino acid residues are identical. The total number of such position identities is then divided by the total number of nucleotides or residues in the reference sequence to give % sequence identity. Sequence identity can be readily calculated by known methods, including but not limited to, those described in Computational Molecular Biology, Lesk, A. N., ed., Oxford University Press, New York (1988), Biocomputing: Informatics and Genome Projects, Smith, D. W., ed., Academic Press, New York (1993); Computer Analysis of Sequence Data, Part I, Griffin, A. M., and Griffin, H. G., eds., Humana Press, New Jersey (1994); Sequence Analysis in Molecular Biology, von Heinge, G., Academic Press (1987); Sequence Analysis Primer, Gribskov, M. and Devereux, J., eds., M. Stockton Press, New York (1991); and Carillo, H., and Lipman, D., SIAM J. Applied Math., 48: 1073 (1988), the teachings of which are incorporated herein by reference. Preferred methods to determine the sequence identity are designed to give the largest match between the sequences tested. Methods to determine sequence identity are codified in publicly available computer programs which determine sequence identity between given sequences. Examples of such programs include, but are not limited to, the GCG program package (Devereux, J., et al., Nucleic Acids Research, 12(1):387 (1984)), BLASTP, BLASTN and FASTA (Altschul, S. F. et al., J. Molec. Biol., 215:403-410 (1990). The BLASTX program is publicly available from NCBI and other sources (BLAST Manual, Altschul, S. et al., NCVI NLM NIH Bethesda, Md. 20894, Altschul, S. F. et al., J. Molec. Biol., 215:403-410 (1990), the teachings of which are incorporated herein by reference). These programs optimally align sequences using default gap weights in order to produce the highest level of sequence identity between the given and reference sequences. As an illustration, by a polynucleotide having a nucleotide sequence having at least, for example, 85%, preferably 90%, even more preferably 95% "sequence identity" to a reference nucleotide sequence, it is intended that the nucleotide sequence of the given polynucleotide is identical to the reference sequence except that the given polynucleotide sequence may include up to 15, preferably up to 10, even more preferably up to 5 point mutations per each 100 nucleotides of the reference nucleotide sequence. In other words, in a polynucleotide having a nucleotide sequence having at least 85%, preferably 90%, even more preferably 95% identity relative to the reference nucleotide sequence, up to 15%, preferably 10%, even more preferably 5% of the nucleotides in the reference sequence may be deleted or substituted with another nucleotide, or a number of nucleotides up to 15%, preferably 10%, even more preferably 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having a given amino acid sequence having at least, for example, 85%, preferably 90%, even more preferably 95% sequence identity to a reference amino acid sequence, it is intended that the given amino acid sequence of the polypeptide is identical to the reference sequence except that the given polypeptide sequence may include up to 15, preferably up to 10, even more preferably up to 5 amino acid alterations per each 100 amino acids of the reference amino acid sequence. In other words, to obtain a given polypeptide sequence having at least 85%, preferably 90%, even more preferably 95% sequence identity with a reference amino acid sequence, up to 15%, preferably up to 10%, even more preferably up to 5% of the amino acid residues in the reference sequence may be deleted or substituted with another amino acid, or a number of amino acids up to 15%, preferably up to 10%, even more preferably up to 5% of the total number of amino acid residues in the reference sequence may be inserted into the reference sequence. These alterations of the reference sequence may occur at the amino or the carboxyl terminal positions of the reference amino acid sequence or anywhere between those terminal positions, interspersed either individually among residues in the reference sequence or in the one or more contiguous groups within the reference sequence. Preferably, residue positions which are not identical differ by conservative amino acid substitutions. However, conservative substitutions are not included as a match when determining sequence identity.

Carriers Molecules

The carrier molecules to which the OMP *Histophilus somni* peptides of the invention can be conjugated or covalently linked are preferably those described above. Preferred carriers for animal use are bovine serum albumin and Keyhole Limpet Hemocyanin. Protein carriers suitable for human use include tetanus toxoid, diphtheria toxoid, acellular pertussis vaccine (LPF toxoid), cross-reacting materials (CRM's) which are antigenically similar to bacterial toxins but are non-toxic by means of mutation. For example, CRM 197 obtained according to Pappenheimer, et al, Immunochemistry, 9, 891-906 (1972), and other bacterial protein carriers, for example meningococcal outer membrane protein may be used. Preferably, the carrier protein itself is an immunogen.

The OMP *Histophilus somni* peptides of the invention may be covalently coupled to the carrier by any convenient method known to the art. While use of a symmetric linker such as adipic acid dihydrazide, as described by Schneerson et al, J. Experimental Medicine, 152, 361-376 (1980), or a heterobifunctional linker such as N-succinimidyl 3-(2-pyridyldithio) propionate as described by Fattom et al, Infection and Immunity, 56, 2292-2298 (1988) are within the scope of the invention, it is preferred to avoid the use of any linker but instead couple a *Histophilus somni* peptide of the invention directly to the carrier molecule. Such coupling may be achieved by means of reductive amination as described by Landi et al J. Immunology, 127, 1011-1019 (1981).

The size of the immunogenic composition, as defined by average molecular weight, is variable and dependent upon the chosen OMP *Histophilus somni* peptide(s) and the method of coupling of the OMP *Histophilus somni* peptide(s) to the carrier. Therefore, it can be as small as 1,000 daltons ($10^3$) or greater than $10^6$ daltons. With the reductive amination coupling method, the molecular weight of the *Histophilus somni* peptide(s) is usually within the range of 5,000 to 500,000, for example 300,000 to 500,000, or for example 5,000 to 50,000 daltons.

Carrier molecules, i.e. peptides, derivatives and analogs thereof, and peptide mimetics that specifically bind an OMP *Histophilus somni* peptide of the invention can be produced by various methods known in the art, including, but not limited to solid-phase synthesis or by solution (Nakanishi et al., 1993, Gene 137:51-56; Merrifield, 1963, J. Am. Chem. Soc. 15:2149-2154; Neurath, H. et al., Eds., The Proteins, Vol II, 3d Ed., p. 105-237, Academic Press, New York, N.Y. (1976), incorporated herein in their entirety by reference).

The OMP *Histophilus somni* peptides of the invention or the antibodies or binding portions thereof of the present invention may be administered in injectable dosages by solution or suspension of in a diluent with a pharmaceutical or veterinary carrier.

Toxicity and therapeutic efficacy of such molecules can be determined by standard pharmaceutical procedures in cell cultures or experimental animals, e.g., for determining the $LD_{50}$ (the dose lethal to 50% of the population).

The vaccines of the invention may be multivalent or univalent. Multivalent vaccines are made from immuno-conjugation of multiple OMP *Histophilus somni* peptides with a carrier molecule.

In one aspect, the OMP *Histophilus somni* peptide compositions comprise an effective immunizing amount of the immunogenic conjugate, preferably in combination with an immunostimulant; and a physiologically acceptable vehicle. As used in the present context, "immunostimulant" is intended to encompass any compound or composition which has the ability to enhance the activity of the immune system, whether it be a specific potentiating effect in combination with a specific antigen, or simply an independent effect upon the activity of one or more elements of the immune response. Immunostimulant compounds include but are not limited to mineral gels, e.g., aluminum hydroxide; surface active substances such as lysolecithin, pluronic polyols; polyanions; peptides; oil emulsions; alum, and MDP. Methods of utilizing these materials are known in the art, and it is well within the ability of the skilled artisan to determine an optimum amount of stimulant for a given vaccine. More than one immunostimulant may be used in a given formulation. The immunogen may also be incorporated into liposomes, or conjugated to polysaccharides and/or other polymers for use in a vaccine formulation.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration preferably for administration to a mammal, especially a pig. Associated with such container(s) can be a notice in the form prescribed by a governmental agency regulating the manufacture, use or sale of pharmaceuticals or biological products, which notice reflects approval by the agency of manufacture, use or sale for human administration.

Adjuvants

In order to further increase the immunogenicity of the immunogenic compositions provided herewith, and which contain one or more OMP *Histophilus somni* peptides may also comprise one or more adjuvants.

The adjuvant may be purified by any of the techniques described previously or known in the art. The preferred purification technique is silica gel chromatography, in particular the "flash" (rapid) chromatographic technique, as described by W. Clark Still et al, J. Organic Chemistry, 43, 2923-2925 (1978). However, other chromatographic methods, including HPLC, may be used for purification of the adjuvant. Crystallization may also be used to purify the adjuvant. In some cases, no purification is required as a product of analytical purity is obtained directly from the synthesis.

The vaccine compositions of the invention are prepared by physically mixing the adjuvant with the OMP *Histophilus somni* peptide(s) under appropriate sterile conditions in accordance with known techniques to produce the adjuvanted composition. Complexation of the OMP *Histophilus somni* peptide(s) and the adjuvant is facilitated by the existence of a net negative charge on the conjugate which is electrostatically attracted to the positive charge present on the long chain alkyl compound adjuvant.

It is expected that an adjuvant can be added in an amount of about 100 μg to about 10 mg per dose, preferably in an amount of about 100 μg to about 10 mg per dose, more preferably in an amount of about 500 μg to about 5 mg per dose, even more preferably in an amount of about 750 μg to about 2.5 mg per dose, and most preferably in an amount of about 1 mg per dose. Alternatively, the adjuvant may be at a concentration of about 0.01% to 75%, preferably at a concentration of about 2% to 60%, more preferably at a concentration of about 5% to 25%, still more preferably at a concentration of about 7% to 22%, and most preferably at a concentration of 10% to 20% by volume of the final product.

Physiologically-Acceptable Vehicles

The vaccine compositions of this invention may be formulated using techniques similar to those used for other pharmaceutical polypeptide compositions. Thus, the adjuvant and OMP *Histophilus somni* peptide(s), preferably conjugated to carrier molecule and/or admixed with an adjuvant may be stored in lyophilized form and reconstituted in a physiologically acceptable vehicle to form a suspension prior to administration. Alternatively, the adjuvant and conjugate may be stored in the vehicle. Preferred vehicles are sterile solutions, in particular, sterile buffer solutions, such as phosphate buffered saline. Any method of combining the adjuvant and the conjugate in the vehicle such that improved immunological effectiveness of the immunogenic composition is appropriate.

The volume of a single dose of the vaccine of this invention may vary but will be generally within the ranges commonly employed in conventional vaccines. The volume of a single dose is preferably between about 0.1 ml and about 3 ml, preferably between about 0.2 ml and about 1.5 ml, more preferably between about 0.2 ml and about 0.5 ml at the concentrations of conjugate and adjuvant noted above.

The vaccine compositions of the invention may be administered by any convenient means.

Formulation

Immunogenic conjugates comprising an OMP *Histophilus somni* peptide(s) coupled to a carrier molecule can be used as vaccines for immunization against one or more serotypes of *Histophilus somni*. The vaccines, comprising the immunogenic conjugate in a physiologically acceptable vehicle, are useful in a method of immunizing animals, preferably ruminants, including bovine or ovine for treatment or prevention of infections by *Histophilus somni*.

Antibodies generated against immunogenic conjugates of the present invention by immunization with an immunogenic conjugate can be used in passive immunotherapy and generation of antiidiotypic antibodies for treating or preventing infections of *Histophilus somni*.

The subject to which the composition is administered is preferably an animal, including but not limited to cows, horses, sheep, pigs, poultry (e.g. chickens), goats, cats, dogs, hamsters, mice and rats, most preferably the mammal is a cow In another embodiment the subject is a human.

The formulations of the invention comprise an effective immunizing amount of one or more immunogenic compositions or antibodies thereto and a physiologically acceptable vehicle. Vaccines comprise an effective immunizing amount of one or more immunogenic compositions and a physiologically acceptable vehicle. The formulation should suit the mode of administration.

The immunogenic composition, if desired, can also contain minor amounts of wetting or emulsifying agents, or pH buffering agents. The immunogenic composition can be a liquid solution, suspension, emulsion, tablet, pill, capsule, sustained release formulation, or powder. Oral formulation can include standard carriers such as pharmaceutical grades of mannitol, lactose, starch, magnesium stearate, sodium saccharine, cellulose, magnesium carbonate, etc.

Effective Dose

The compounds described herein can be administered to a subject at therapeutically effective doses to treat *Histophilus somni*-associated diseases. The dosage will depend upon the host receiving the vaccine as well as factors such as the size, weight, and age of the host.

The precise amount of immunogenic conjugate or antibody of the invention to be employed in a formulation will depend on the route of administration and the nature of the subject (e.g., species, age, size, stage/level of disease), and should be decided according to the judgment of the practitioner and each subject's circumstances according to standard clinical techniques. An effective immunizing amount is that amount sufficient to treat or prevent a *Histophilus somni* infectious disease in a subject. Effective doses may also be extrapolated from dose-response curves derived from animal model test systems and can vary from 0.001 mg/kg to 100 mg/kg, and more preferably a dose of about 400 μg/dose.

Toxicity and therapeutic efficacy of compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in animals, especially cattle, or humans. The dosage of such compounds lies preferably within a range of circulating concentrations that include the $ED_{50}$ with little or no toxicity. The dosage can vary within this range depending upon the dosage form employed and the route of administration utilized. For any compound used in the methods of the invention, the therapeutically effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in subjects. Levels in plasma can be measured, for example, by high performance liquid chromatography.

Immunogenicity of a composition can be determined by monitoring the immune response of test subjects following immunization with the composition by use of any immunoassay known in the art. Generation of a humoral (antibody) response and/or cell-mediated immunity, may be taken as an indication of an immune response. Test subjects may include animals such as pigs, mice, hamsters, dogs, cats, rabbits, cows, horses, sheep, poultry (e.g. chickens, ducks, geese, and turkeys), and humans.

The immune response of the test subjects can be analyzed by various approaches such as: the reactivity of the resultant immune serum to the immunogenic conjugate, as assayed by known techniques, e.g., enzyme linked immunosorbent assay (ELISA), immunoblots, immunoprecipitations, etc.; or, by protection of immunized hosts from infection by the pathogen and/or attenuation of symptoms due to infection by the pathogen in immunized hosts as determined by any method known in the art, for assaying the levels of an infectious disease agent, e.g., the bacterial levels (for example, by culturing of a sample from the subject), or other technique known in the art. The levels of the infectious disease agent may also be determined by measuring the levels of the antigen against which the immunoglobulin was directed. A decrease in the levels of the infectious disease agent or an amelioration of the symptoms of the infectious disease indicates that the composition is effective.

The therapeutics of the invention can be tested in vitro for the desired therapeutic or prophylactic activity, prior to in vivo use in animals or humans. For example, in vitro assays that can be used to determine whether administration of a specific therapeutic is indicated include in vitro cell culture assays in which appropriate cells from a cell line or cells cultured from a subject having a particular disease or disorder are exposed to or otherwise administered a therapeutic, and the effect of the therapeutic on the cells is observed.

Alternatively, the therapeutic may be assayed by contacting the therapeutic to cells (either cultured from a subject or from a cultured cell line) that are susceptible to infection by the infectious disease agent but that are not infected with the infectious disease agent, exposing the cells to the infectious disease agent, and then determining whether the infection rate of cells contacted with the therapeutic was lower than the infection rate of cells not contacted with the therapeutic. Infection of cells with an infectious disease agent may be assayed by any method known in the art.

In addition, the therapeutic can be assessed by measuring the level of the molecule against which the antibody is directed in the animal model or human subject at suitable time intervals before, during, or after therapy. Any change or absence of change in the amount of the molecule can be identified and correlated with the effect of the treatment on the subject. The level of the molecule can be determined by any method known in the art.

After vaccination of an animal to an OMP *Histophilus somni* using the methods and compositions of the present invention, any binding assay known in the art can be used to assess the binding between the resulting antibody and the particular molecule. These assays may also be performed to select antibodies that exhibit a higher affinity or specificity for the particular antigen.

Detection and Diagnostic Methods

Antibodies, or binding portions thereof, resulting from the use of OMP *Histophilus somni* peptides of the present invention are useful for detecting in a sample the presence of *Histophilus somni* bacteria. This detection method comprises the steps of providing an isolated antibody or binding portion thereof raised against an OMP *Histophilus somni* peptide of the invention, adding to the isolated antibody or binding portion thereof a sample suspected of containing a quantity of *Histophilus somni*, and detecting the presence of a complex comprising the isolated antibody or binding portion thereof bound to *Histophilus somni*.

The antibodies or binding portions thereof of the present invention are also useful for detecting in a sample the presence of a *Histophilus somni* peptide. This detection method comprises the steps of providing an isolated antibody or binding portion thereof raised against a *Histophilus somni* peptide, adding to the isolated antibody or binding portion thereof a sample suspected of containing a quantity of the *Histophilus somni* peptide, and detecting the presence of a complex comprising the isolated antibody or binding portion thereof bound to the *Histophilus somni* peptide.

Immunoglobulins, particularly antibodies, (and functionally active fragments thereof) that bind a specific molecule that is a member of a binding pair may be used as diagnostics and prognostics, as described herein. In various embodiments, the present invention provides the measurement of a member of the binding pair, and the uses of such measurements in clinical applications. The immunoglobulins in the present invention may be used, for example, in the detection of an antigen in a biological sample whereby subjects may be tested for aberrant levels of the molecule to which the immunoglobulin binds, and/or for the presence of abnormal forms of such molecules. By "aberrant levels" is meant increased or decreased relative to that present, or a standard level representing that present, in an analogous sample from a portion of the body or from a subject not having the disease. The antibodies of this invention may also be included as a reagent in a kit for use in a diagnostic or prognostic technique.

In one aspect, an antibody of the invention that immunospecifically binds to a *Histophilus somni* peptide may be used to diagnose, prognose or screen for a *Histophilus somni* infection.

In another aspect, the invention provides a method of diagnosing or screening for the presence of a *Histophilus somni* infection or immunity thereto, comprising measuring in a subject the level of immunospecific binding of an antibody to a sample derived from the subject, in which the antibody immunospecifically binds a *Histophilus somni* peptide in which an increase in the level of said immunospecific binding, relative to the level of said immunospecific binding in an analogous sample from a subject not having the infectious disease agent, indicates the presence of *Histophilus somni*.

Examples of suitable assays to detect the presence of *Histophilus somni* peptides or antagonists thereof include but are not limited to ELISA, radioimmunoassay, gel-diffusion precipitation reaction assay, immunodiffusion assay, agglutination assay, fluorescent immunoassay, protein A immunoassay, or immunoelectrophoresis assay.

Immunoassays for the particular molecule will typically comprise incubating a sample, such as a biological fluid, a tissue extract, freshly harvested cells, or lysates of cultured cells, in the presence of a detectably labeled antibody and detecting the bound antibody by any of a number of techniques well-known in the art.

The binding activity of a given antibody may be determined according to well known methods. Those skilled in the art will be able to determine operative and optimal assay conditions for each determination by employing routine experimentation.

An additional aspect of the present invention relates to diagnostic kits for the detection or measurement of *Histophilus somni*. Kits for diagnostic use are provided, that comprise in one or more containers an anti *Histophilus somni* peptide antibody, and, optionally, a labeled binding partner to the antibody. Alternatively, the anti OMP *Histophilus somni* peptide antibody can be labeled (with a detectable marker, e.g., a chemiluminescent, enzymatic, fluorescent, or radioactive moiety). Accordingly, the present invention provides a diagnostic kit comprising, an anti OMP *Histophilus somni* peptide antibody and a control immunoglobulin. In a specific embodiment, one of the foregoing compounds of the container can be detectably labeled. A kit can optionally further comprise in a container a predetermined amount of an OMP *Histophilus somni* peptide recognized by the antibody of the kit, for use as a standard or control.

Administration to a Subject

Preferred routes of administration include but are not limited to intranasal, oral, intradermal, and intramuscular. Administration in drinking water, most preferably in a single dose, is desirable. The skilled artisan will recognize that compositions of the invention may also be administered in one, two or more doses, as well as, by other routes of administration. For example, such other routes include subcutaneously, intracutaneously, intravenously, intravascularly, intraarterially, intraperitnoeally, intrathecally, intratracheally, intracutaneously, intracardially, intralobally, intramedullarly, intrapulmonarily, and intravaginally. Depending on the desired duration and effectiveness of the treatment, the compositions according to the invention may be administered once or several times, also intermittently, for instance on a daily basis for several days, weeks or months and in different dosages.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Example 1

Development of a Respiratory Challenge Model in CD Calves

A. Objective

In order to evaluate any prototype vaccine, a satisfactory and consistent challenge model was needed to show that appropriate disease manifests in non-treated animals. Most published literature and previous work by the BIVI Research and Development Lab has used Isolate 5166, obtained from the University of California—San Diego (UCSD) for challenge purposes, but this has produced inconsistent results. In an effort to develop a more consistent model, more recently acquired field isolates were used in comparison with the 5166 Isolate to establish which would provide sufficient clinical signs, lung pathology, and mortality to serve in further work to evaluate vaccine prototypes. According to previous literature, wild-type infections which remain untreated in the field result in an average of 15% lung involvement (Griffin 2009). This measure was utilized to determine the success of the challenge model.

B. Materials and Methods

Bacterial Isolates

Isolate 5166 was obtained from UCSD for use as a control. Isolates 35576 (obtained from the Iowa State University Veterinary Diagnostics Lab—ISUVDL), LgD1-TN08 (PTA-12756), and Lg2-OK08 (PTA-12755) were recovered from field cases with a diagnosis of bacterial pneumonia. All isolate stocks were prepared and stored on Cryobeads (Copan Diagnostics). Growth was completed by utilization of a sterile 10 uL loop to streak the beads to Columbia Blood Agar (CBA) plates which contained 5% sheep blood (Remel) and incubated for 24 hours at 37° C. with 10% $CO_2$. Individual colonies were selected from these plates and streaked to new CBA plates for lawn growth and incubated again for 24 hours. Bacterial lawns were harvested into 1.0 mL Sterile Phosphate Buffered Saline (PBS—Gibco) and 300 uL was used to inoculate CBA in T-150 flasks (Corning) and spread by the use of sterile glass beads. The larger vessels were again incubated at 37° C. with 10% $CO_2$ and then harvested on the day of challenge at eighteen hours of growth by utilization of the glass beads to dislodge the culture into 6.0 mL RPMI-1640 media (Hyclone) containing 5% Fetal Bovine Serum (FBS—SAFC) per flask. Previous work has shown that a transmittance of 75% at 610 nm correlates to approximately $3.0 \times 10^8$ CFU/mL. Using this approximation cultures were diluted in RPMI-1640 to a final concentration of $1.0 \times 10^9$ CFU/mL.

Calves

Sixty-seven colostrum deprived, Holstein calves which tested as negative for persistent infection by Bovine Viral Diarrhea Virus (BVDV) by ear notch, *Mycoplasma bovis* by q-PCR of nasal swabs, and which had not received any *H. somni* vaccination, were obtained from Dykstra Dairy (Strubble, Iowa). All calves were determined by the attending veterinarian on site at the BIVI research farm in Sioux Center, Iowa to be in good health prior to the start of the study. At the time of challenge, calf ages ranged from 55 to 71 days with a mean of 59 days. Animals were fed a daily ration appropriate for their age and weight according to facility procedures. Water was available ad libitum by means of rubber containers available to each pen. The calves were randomly assigned to each of five groups and randomly assigned to an individual pen, arranged in blocks of ten.

Challenge

Strict Control animals were euthanized and necropsied prior to challenge to ensure a lack of respiratory pathology from the source. Other control animals were administered 2×20.0 mL doses of RPMI 1640 Media containing 5% FBS intratracheally via endoscope with no *H. somni*. For all experimental animals, 20.0 mL of harvested *H. somni* from the assigned isolate was diluted to $1.0 \times 10^9$ CFU/mL and administered to each calf intratracheally at the level of the first bifurcation via endoscope for a total estimated challenge dose of $2.0 \times 10^{10}$ CFU. This was followed by a 20.0 mL wash with RPMI-1640 Media containing 5% FBS.

Clinical Observations

Clinical signs and rectal temperatures were observed daily for seven days following challenge. Although all body systems were observed, special attention was paid to signs of respiratory stress. Animals which showed signs of severe respiratory distress, became unable to stand, or could not reach food and/or water without assistance were euthanized for humane reasons and necropsied. All remaining animals were euthanized and necropsied at seven days post challenge. At the time of necropsy, gross pathology and the percentage of lung pathology present in each lung lobe was recorded by the attending veterinarian. Samples of lung consisting of tissue from the margin of the lesion and good tissue were collected. Two samples were collected per calf and stored on ice until the time of delivery to the lab for testing. An additional sample from each calf was fixed in 10% formalin for histopathological examination.

Bacterial Recovery

Tissue was seared using a propane torch and then aseptically cut to expose an interior surface. A dry swab was inserted into the tissue and rotated to sample. The swab was dipped in to 5 ml of BHI broth supplemented with tris-buffer and thiamine monophosphate as suggested by Asmussen and Baugh (1981). Broth tubes were incubated for 24-72 hours at 37° C. w/130 rpm shaking. The second set of tissue was stored at −70° C. Following incubation, broth cultures were scored as positive or negative for growth based on turbidity in comparison to positive and negative control tubes.

PCR

To verify the presence of *H. somni* within the cultures from infected lungs, a 50 uL sample was taken from each broth culture and subjected to DNA extraction (Qiagen DNA kit) and tested for presence of *H. somni* DNA by q-PCR. The primers utilized were *H. somni* species specific for sequences within the 16S rDNA—Forward Primer (5'-GAAGGCGATTAGTTTAAGAG-3') (SEQ ID NO: 1) and Reverse Primer (5'-TTCGGGCACC AAGTRTTCA-3') (SEQ ID NO: 2) (Angen and others 1998). PCR was carried out in a 96-well format in 25 uL volumes using a CFX-96 Thermocycler (Bio-Rad) with Bio-Rad Master Mix, 0.4 ug/uL Bovine Serum Albumin (BSA), and a set of in-process control primers to verify the validity of the reaction in each well. A standard curve of *H. somni* DNA was run on each plate. An initial activation step at 95.0° C. for five minutes was performed, followed by forty-five cycles of denaturing at 95.0° C. for fifteen seconds and annealing/elongation step at 60.0° C. for thirty seconds with a real-time capture of probe fluorescence at the end of each cycle. Data was captured and analyzed using the Bio-Rad CFX software. Samples were run in duplicate and mean threshold cycle ($C_t$) was compared to the standard to determine whether each sample was positive or negative. In the event that a sample had one positive and one negative well, the sample was re-run in triplicate with final determination of positivity determined by which result was represented in >50% of the tested wells.

Histopathology

Lung samples fixed in 10% formalin were transported to the ISU-VDL in Ames, Iowa for histopathological examination. A scoring system of 0-4 was used. A score of 0 indicated no microscopic lesions, 1 indicated mild or focal lesions, 2 designated moderate or multi-focal lesions, 3 designated severe or diffuse microscopic lesions, and 4 designated severe, diffuse microscopic lesions.

Results

All challenged groups showed a detectable increase in mean rectal temperatures when compared to the control group over the course of the study. Isolate 5166 was the quickest to reach a peak temperature on Day 1 however isolate 35576 achieved the highest rectal temperature observed on Day 2. Rectal Temperatures of groups challenged with each isolate showed a decrease in average from a peak temperature on Day 1 or 2. When comparing the observed rectal temperatures between groups, only isolate 35576 showed a significant increase in temperature above those of the other isolates (p=0.004). Mean rectal temperatures over the course of the challenge period are summarized in FIG. 1.

Clinical signs such as depression, decreased appetite, rapid breathing, labored breathing, lowered head, reluctance to move, ocular and nasal discharge were all observed in challenged animals. Signs were most severe and most prevalent on Day 1 through Day 3 following challenge. The most severe and highest number of symptoms was observed in Group 2 (Isolate Lg2-OK08) where eleven out of fifteen animals were either found dead or euthanized for humane reasons by Day 3. Mortality is summarized in Table 1.

Bacterial culture and subsequent q-PCR analysis showed a high rate of recovery from the lungs of all challenged groups. Group 2 (Lg2-OK08) yielded only one animal from which positive PCR of lung tissue culture was not observed.

Figure 2:
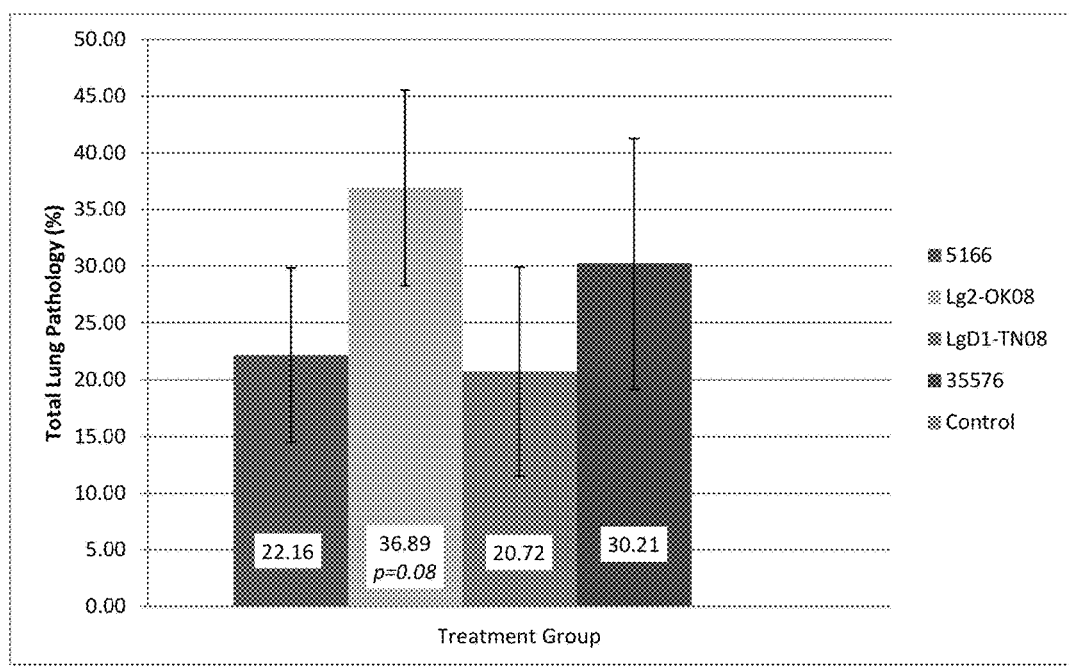
FIG. 2. is a graph illustrating total percent lung pathology. Percentage of lung involvement was determined by the attending site veterinarian's observation and palpation of each lobe. Total percentage was calculated using the method described by Jericho and Langford (1982). Error bars represent confidence with $\alpha=0.1$. Non-challenged control animals displayed no pathology. All challenged groups produced sufficient pathology to consider the challenge a success, however Isolate Lg2-OK08 showed the highest, and most consistent virulence, and significantly more pathology than isolate 5166 (p=0.08).

Total lung pathology was measured upon necropsy of each animal. Lung consolidation with hepatization ranging from red to gray to yellow was observed. The lesions followed the bronchial tree. Fibrin tags with adhesions to the rib cage were also seen with excess fluid in the thoracic cavity and on the pericardial sac of some animals. Some of the animals had pleurisy as well. Group 2 (Lg2-OK08) produced 36.89%±8.64% (α=0.1) total lung involvement. Group 1 (5166) produced 22.16%±7.66% (α=0.1) total lung involvement. This difference is statistically significant (p=0.08). Lung pathology is summarized in FIG. 2.

Lung tissues were scored on the severity of lesions (0-4 scale) and whether the observations were compatible with bacterial pneumonia. No significant differences were found between groups, but successful causation of pneumonia by challenge with each isolate is supported. Severity scores for the histopathological examination are summarized in Table 2.

TABLE 1

Mortality by Treatment Group

| Treatment | Day 1 | Day 2 | Day 3 | Total |
|---|---|---|---|---|
| 5166 | 1/15 | 1/15 | 1/15 | 3/15 |
| | (6.7%) | (6.7%) | (6.7%) | (20.0%) |
| Lg2-OK08 | 5/15 | 1/15 | 4/15 | 10/15* |
| | (33.3%) | (6.7%) | (26.7%) | (66.7%) |
| LgD1-TN08 | 2/15 | 2/15 | 2/15 | 6/15 |
| | 13.3% | (13.3%) | (13.3%) | (40.0%) |
| 35576 | 3/14 | 0/14 | 6/14 | 9/14** |
| | (21.4%) | (0.0%) | (42.9%) | (64.3%) |
| Control | 0/5 | 0/5 | 0/5 | 0/5 |
| | (0.0%) | (0.0%) | (0.0%) | (0.0%) |

*Isolate Lg2-OK08 produced significantly higher mortality (p = 0.01) than 5166
**Isolate 35576 produced significantly higher mortality (p = 0.02) than 5166
Mortality is reported as the number of deaths in each group on each day that such events were observed. Percentages represent the proportion of the treatment group affected. No animals died between the morning of Day 3 and the Final Necropsy on Day 7.

C. Conclusion

The purpose of this study was to determine if Isolates Lg2-OK08, LgD1-TN08, and 35576 could be used in a successful challenge model in comparison with the previously used Isolate 5166. Isolate Lg2-OK08 outperformed the original isolate 5166 in producing clinical manifestations of disease including an equivalent mean rectal temperature over the course of the study, with a higher peak temperature on Day 2, more visible clinical signs, significantly higher mortality, and significantly increased lung lesion percentage in this experiment. Isolate Lg2-OK08 also produced more consistent results than either of the other tested isolates (LgD1-TN08 or 35576). While all isolates tested produced bacterial pneumonia and displayed the desired lung pathology (≥15%) as intended by the model, Isolate Lg2-OK08 appears to show the strongest virulence in comparison to the other isolates. As this isolate produced adequate pathogenesis consistently within the treatment group and may more accurately reflect current wild-type respiratory infections due to its more recent isolation; Lg2-OK08 was utilized for further work as a challenge organism.

TABLE 2

Severity Scores from Histopathological Examination

| Treatment | Overall Histological Severity | | | | |
|---|---|---|---|---|---|
| | 0 | 1 | 2 | 3 | 4 |
| 5166 | 2 (13.3%) | 1 (6.7%) | 5 (33.3%) | 5 (33.3%) | 2 (13.3%) |
| Lg2-OK08 | 1 (6.7%) | 2 (13.3%) | 5 (33.3%) | 5 (33.3%) | 2 (13.3%) |
| LgD1-TN08 | 3 (20.0%) | 1 (6.7%) | 7 (46.7%) | 4 (26.7%) | 0 |
| 35576 | 1 (7.1%) | 1 (7.1%) | 4 (28.6%) | 3 (21.4%) | 5 (35.7%) |
| Control | 4 (80.0%) | 1 (20.0%) | 0 | 0 | 0 |

Severity scores were assigned based on assessment by technicians of the ISU-VDL. Percentages indicate the proportion of the treatment group displaying a given severity of microscopic lesions.
Scoring:
0 = No Microscopic Lesions
1 = Mild or Focal Lesions
2 = Moderate or Multi-focal Lesions
3 = Severe or Diffuse Lesions
4 = Severe, Diffuse Lesions Example 2

Vaccine Strategy Evaluation in a CD Calf Model

A. Objective

The goal of this study was to evaluate the efficacy of various vaccine prototypes representing currently available vaccine technologies against the respiratory challenge model described in Example 1. Vaccines investigated in this study included a killed bacterin, two modified-live mutants with deletions in biofilm formation genes, and a crude OMP extract obtained by sarcosyl extraction. The success of the respiratory challenge was again measured against lung pathology observed in field studies with confirmation by bacterial recovery, *H. somni* specific PCR, and histopathological examination of microscopic lesions. The efficacy of the vaccines was evaluated based on the reduction of lung pathology in comparison to non-vaccinated controls.

B. Materials and Methods

Bacterial Isolates

*H. somni* isolate Lg2-OK08 (PTA-12755) was utilized for OMP extraction as well as for challenge. Two modified-live deletion mutants lacking certain biofilm formation characteristics were obtained from Virginia Polytechnic Institute and State University (VATech). A commercially available killed bacterin product was obtained to serve as a comparison between the efficacy of currently available methods and the prototypes. Growth of Isolate Lg2-OK08 for OMP extraction is described in the following section. Growth of this isolate for challenge, as well as the growth of the modified-live vaccine isolates was conducted identically to the method reported for Example 1.

OMP Extraction

Methods for OMP extraction were modified from methods described by Bollag and others (1996) and Rehm (2006). Isolate Lg2-OK08 (PTA-12755) stored on Cryobeads (Copan Diagnostics) was struck to CBA plates containing 5% calf blood (Remel) and incubated at 37° C. with 10% $CO_2$ for twenty-four hours. Colonies were then transferred to 10 mL of a proprietary broth media (BIVI) supplemented with FBS (SAFC), yeast extract (BIVI), and dextrose (BIVI) in a 50 mL conical tube (Corning). The broth was incubated at 37° C. with 130 rpm shaking for twenty-four hours. Turbidity consistent with typical *H. somni* growth was verified by measuring optical density (OD) at 610 nm using a spectrophotometer and 1.5 mL of this initial culture was inoculated into 1.5 L of fresh media in a 2.8 L shake flask. The larger cultures were incubated at 37° C. with 130 rpm shaking for eighteen hours. Bacteria was harvested by centrifugation of the culture at 10,000×G for ten minutes. Harvested cells were then resuspended at a 10× concentration in 10 mM 4-(2-hyrdoxyethyl)-1-piperazineehtanesulfonic acid (HEPES) buffer (Sigma) containing protease inhibitors (Sigma). The resuspended pellets were then subjected to three cycles of freezing and thawing to begin cell lysis. Following the third thaw, cultures were subjected to further cell lysis by three rounds of sonication using a cup horn with 0.5 second bursts at full amplitude for one minute. Cell lysates were then centrifuged at 17,000×G for twenty minutes to remove cell debris. The resultant supernatant was then centrifuged at 100,000×G at 4° C. for one hour to pellet membrane bound proteins. The pellet from this centrifugation was resuspended at 10× concentration in 10 mM HEPES with protease inhibitor (Sigma) and then treated with 2.0% sarcosyl (Sigma) for thirty minutes at room temperature to solubilize non-protein components. The treated suspension was again centrifuged at 100,000×G at 4° C. for one hour to pellet the proteins. The resultant pellet was then resuspended in 10 mM HEPES and diluted to a final concentration of 1.0 mg/mL as shown by BCA Total Protein Assay Kit (Thermo).

The extraction process was shown to be less efficient than expected in the total amount of protein produced, it was also observed that much of the protein from the final treatment remained in the soluble fraction. Western blotting of these preps using serum from calves who had received a killed bacterin vaccine, indicated that the protein profiles of these two fractions was nearly identical. In order to provide enough material for vaccination, both the insoluble and soluble fractions from the sarcosyl treatment were used in this vaccination.

Calves

Seventy colostrum deprived, Holstein calves which tested as negative for persistent infection by BVDV by ear notch, *M. bovis* by q-PCR of nasal swabs, and which had not received any previous *H. somni* vaccination, were obtained from J&R Livestock (Iowa). Calf age ranged from 41 to 51 days at the time of first vaccination with a median age of 90 days at the time of challenge. All calves were determined, by the attending veterinarian on site at the BIVI research farm in Cosby, Mo., to be in good health prior to the start of the study. Animals were fed a daily ration appropriate for their age and weight according to facility procedures. Water was available ad libitum by means of rubber containers available to each pen. The calves were randomly assigned to each of five groups and assigned individual crates in blocks according to treatment. Control animals were assigned crates as far from the modified-live vaccinates as possible for the vaccination phase of this study. Furthermore for the duration of vaccination, animals were always attended in the same order: controls, bacterin vaccinates, OMP vaccinates, and then modified live vaccinates.

Vaccination and Challenge

Vaccines were administered on Day 0 of the study and then boosters given three weeks later on Day 21. Challenge control animals were administered PBS only. Bacterin vaccinates were given 2.0 mL doses subcutaneously (SQ) as suggested on the manufacturer's label. OMP vaccinates were given 400 ug of OMP material per dose SQ in Freund's Incomplete Adjuvant (Sigma). Modified live vaccinates received 2.0 mL doses through two different routes (SQ and internasally—IN) with an estimated $1.0 \times 10^9$ CFU/dose.

On Day 41 (one day prior to challenge), animals were randomly reassigned to new pens to act as a stressor. On Day 42 animals were challenged with $1.0 \times 10^{10}$ CFU of Isolate Lg2-OK08 diluted in RPMI-1640 containing 5% FBS in a method identical to the previous study. All post-challenge observations, samples collected, testing methods and humane endpoints were identical to those described in Example 1. The vaccination and challenge schedule are summarized in Table 3.

Bacterial Recovery

Swabs of lung tissue were used for bacterial detection. In a method identical to Study 1, lung tissue was seared over an open flame, moved to a sterile hood, and an incision was made so the interior surface of the tissue could be swabbed aseptically. These swabs were then transferred to growth media. Due to a lack of turbidity observed following incubation, a second lung tissue sample, which had been stored at −70° C. was subsequently thawed. The above procedure from Study 1 was repeated, and a second swab was used to streak Columbia Blood Agar (CBA) plates with 5% sheep's blood (Remel). The second swab was retained for direct PCR as well. Samples from each broth culture, agar plate, and the swabs from the second set of testing were each subjected to DNA extraction and PCR analysis.

PCR

To verify the presence of *H. somni* within the cultures from infected lungs, a 50 uL sample was taken from each broth culture and subjected to DNA extraction (Qiagen DNA kit) and tested for presence of *H. somni* DNA by q-PCR using primers specific for the *H. somni* 16S gene as described for Study 1. PCR was carried out in a 96-well format in 25 uL volumes using a CFX-96 Thermocycler (Bio-Rad) with Bio-Rad Master Mix, 0.4 ug/uL Bovine

TABLE 3

Experimental Design Group Treatments

| Groups | Animals/group | Vaccine | | | Challenge | | |
|---|---|---|---|---|---|---|---|
| | | Article | Dose/Route | Admin Schedule | Article | Dose/Route | Admin Schedule |
| Challenge Control | 11 | Sterile PBS | 2.0 mL SQ & 2.0 mL IN | Day 0 & Day 21 | Live *H. somni* Isolate Lg2-OK08 Lg2-OK08 | 20.0 mL in RPMI 1640 @ $1.00 \times 10^{10}$ CFU/dose Followed by 20.0 mL RPMI 1640 Wash | Day 42 |
| Bacterin | 14 | Commercial Vaccine | 2.0 mL SQ | | | | |
| OMP | 14 | OMP Prep | 2.0 mL SQ | | | | |
| Modified Live Mutant 1 | 14 | Live Culture | 2.0 mL SQ & 2.0 mL IN | | | | |
| Modified Live Mutant 2 | 14 | Live Culture | 2.0 mL SQ & 2.0 mL IN | | | | |

Vaccination occurred on Day 0 and Day 21 of the study. Challenge occurred on Day 42

Clinical Observations

Clinical signs and rectal temperatures were observed daily for seven days following challenge. Although all body systems were observed, special attention was paid to signs of respiratory stress. Animals which showed signs of severe respiratory distress, became unable to stand, or could not reach food and/or water without assistance were euthanized for humane reasons and necropsied. All remaining animals were euthanized and necropsied at seven days post challenge. At the time of necropsy, gross pathology and the percentage of lessioning present in each lung lobe was recorded by the attending veterinarian. Samples of lung consisting of tissue from the margin of the lesion and good tissue were collected. Two samples were collected per calf and stored on ice until the time of delivery to the lab for testing. An additional sample from each calf was fixed in 10% formalin for histopathological examination.

Serum Albumin (BSA), and a set of In-Process Control Primers to verify the validity of the reaction in each well. A standard curve of *H. somni* DNA was run on each plate. An initial activation step at 95.0° C. for five minutes was performed, followed by forty-five cycles of denaturing at 95.0° C. for fifteen seconds and annealing/elongation step at 60.0° C. for thirty seconds with a real-time capture of probe fluorescence at the end of each cycle. Data was captured and analyzed using the Bio-Rad CFX software. Samples were run in duplicate and mean threshold cycle ($C_t$) was compared to the standard to determine whether each sample was positive or negative. In the event that a sample had one positive and one negative well, the sample was re-run in triplicate with final determination of positivity determined by which result was represented in >50% of the tested wells.

Histopathology

Lung samples fixed in 10% formalin were transported to the ISU-VDL in Ames, Iowa for histopathological examination. A scoring system of 0-4 was used. A score of 0 indicated no microscopic lesions, 1 indicated mild or focal lesions, 2 designated moderate or multi-focal lesions, 3 designated severe or diffuse microscopic lesions, and 4 designated severe, diffuse microscopic lesions.

Results

Figure 3:
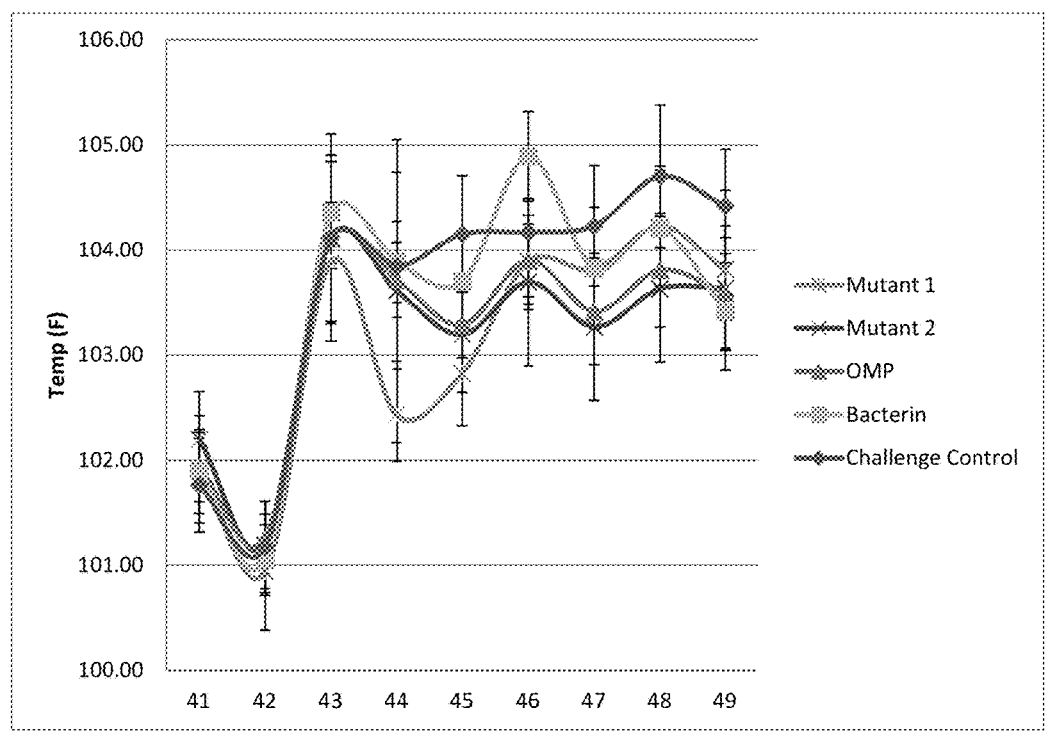
FIG. 3. is a graph illustrating mean rectal temperature by treatment group. Baseline rectal temperatures were obtained by observation both one day prior, and then immediately preceding challenge on Days −41 and 42. Rectal temperatures were recorded daily following challenge and continued until final necropsy occurred on Day 49. Error bars represent confidence with $\alpha=0.1$ FIG. 4. is a graph illustrating total percent lung pathology. Percentage of lung involvement was determined by the attending site veterinarian's observation and palpation of each lobe. Total percentage was calculated using the method described by Jericho and Langford (1982). Error bars represent confidence with $\alpha=0.1$. The OMP vaccine significantly reduced lung pathology (p=0.001) when compared to the non-vaccinated controls.

Rectal temperatures for all groups increased by approximately three degrees on the day following challenge. The bacterin vaccinated group showed the highest average temperature, while the Mutant 1 vaccinated animals had the lowest average temperature. There was no significant reduction in rectal temperature with any of the vaccines. Rectal temperatures are summarized in FIG. 3.

In previous work broth cultures from lung swabs became turbid following 24-72 hours of incubation. In the current study, this turbidity was not observed indicating a lack of recovery of viable bacteria from the lung tissues. The second set of broth cultures again showed no turbidity following 72 hours incubation at 37° C. w/130 rpm shaking. The CBA plates, however, displayed colonies typical of H. somni following 24 hours incubation at 37° C. w/10% $CO_2$ with no apparent growth of any non-H. somni organisms. As described in Table 4, PCR analysis for each of the broth cultures, the plated colonies, and the direct swab all indicated the presence of H. somni.

TABLE 4

H. somni Detection from Challenged Animals

| Bacterial Detection Technique | Treatment Group | | | | | Lung Sample Total by Detection Technique |
|---|---|---|---|---|---|---|
| | Control | Bacterin | OMP | Mutant 1 | Mutant 2 | |
| Fresh Lung Culture | 11/11 (100%) | 14/14 (100%) | 13/14 (92.9%) | 13/14 (92.9%) | 13/14 (92.9%) | 64/67 (95.5%) |
| Frozen Lung Culture | 10/11 (91.0%) | 10/14 (71.4%) | 10/14 (71.4%) | 14/14 (100%) | 12/14 (85.7%) | 56/67 (83.6%) |
| Frozen Lung Plate | 11/11 (100%) | 11/14 (78.6%) | 12/14 (85.7%) | 14/14 (100%) | 12/14 (85.7%) | 60/67 (88.6%) |
| Frozen Lung Swab | 11/11 (100%) | 13/14 (92.9%) | 13/14 (92.9%) | 14/14 (100%) | 13/14 (92.9%) | 64/67 (95.5%) |
| Lung Sample Total By Treatment Group | 43/44 (97.8%) | 48/56 (85.7%) | 48/56 (85.7%) | 55/56 (98.2%) | 50/56 (89.3%) | |

Percentages indicate the proportion of each group which provided successful detection of H. somni by q-PCR specific for the 16s rRNA gene. Neither the fresh, nor the frozen broth cultures produced turbidity that would indicate successful growth of H. somni as has regularly been seen previously, however PCR confirms detectable, if not viable, organisms and the plated cultures indicate that no other contaminating bacteria were present.

Observed clinical signs included depression, decreased appetite, rapid and/or labored respiration, coughing, nasal discharge, shivering, and swelling of the vaccine injection site. Clinical signs for all groups lasted throughout the challenge period; however the OMP vaccinates were left with only a cough at 5 days post-challenge. Treatment with the OMP vaccines resulted in a significant decrease in observed incidence of depression (p=0.06), reduction in the number of days with a decreased appetite (p=0.02), reduction of nasal discharge (p=0.03), and a reduction in the total number of observed clinical signs (p=0.05) when compared to the control group. The Mutant 1 vaccine was the only treatment tested that did not lower the incidence of labored respiration or decrease nasal discharge.

Five animals in the control group died prior to the end of the challenge period. Two animals in the commercial bacterin group, three animals in the Mutant 1 group, and three animals in the Mutant 2 group also died during the course of the challenge period. No animals receiving the OMP vaccine died prior to necropsy, which is significant when compared to the controls (p=0.02). Mortality is summarized in Table 5.

TABLE 5

Mortality by Treatment Group

| Treatment | Day 45 | Day 46 | Day 47 | Day 48 | Total Mortality |
|---|---|---|---|---|---|
| Control | 2/11 (18.2%) | 1/11 (9.1%) | 1/11 (9.1%) | 1/11 (9.1%) | 5/11 (45.5%) |
| Bacterin | 1/14 (7.1%) | 0/14 (0.0%) | 1/14 (7.1%) | 0/14 (0.0%) | 2/14 (14.3%) |
| OMP | 0/14 (0.00%) | 0/14 (0.00%) | 0/14 (0.00%) | 0/14 (0.00%) | 0/14* (0.00%) |
| Mutant 1 | 2/14 (14.3%) | 0/14 (0.0%) | 0/14 (0.0%) | 1/14 (7.1%) | 3/14 (21.4%) |
| Mutant 2 | 2/14 (14.3%) | 1/14 (7.1%) | 0/14 (0.0%) | 0/14 (0.0%) | 3/14 (21.4%) |

*OMP Vaccine produced significantly lower mortality than the controls group (p = 0.02)
Mortality is reported as the number of deaths in each group on each day that such events were observed.
Percentages represent the proportion of the treatment group affected.

Figure 4:
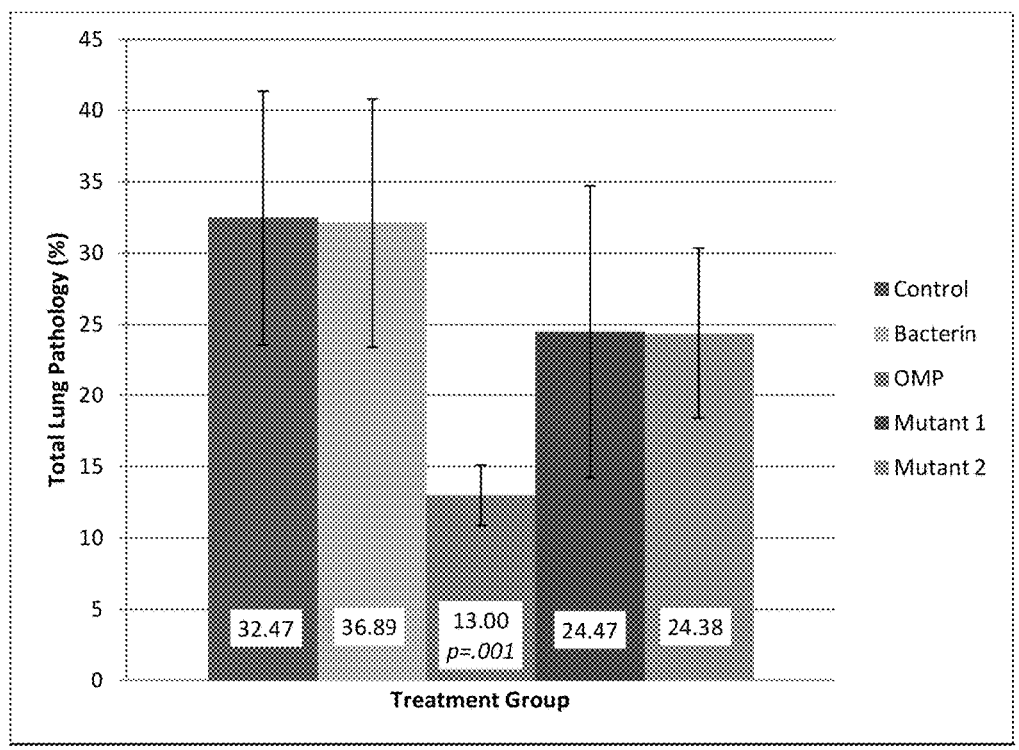

While both modified live mutant isolates showed a decrease in mean percentage of lung lesions when compared to the challenge control group (24.38% for Mutant 1 and 24.47% for Mutant 2), this difference was not found to be statistically significant. The OMP vaccine candidate however produced an average of 13% lung lesions which is significant (p=0.001) when compared to the 32.47% observed in the control group. The commercially available killed bacterin vaccine showed no difference in lesion scores (32.10%) when compared to the control group. Lung pathology is summarized in FIG. 4.

Histological examination was consistent with bacterial pneumonia. The investigator reported that interlobular septa were often widened/dilated with edema, inflammatory cells, and thrombosis of lymphatics. No differences were noted between groups and this data was utilized for conformational purposes only.

C. Conclusion

The evaluation of efficacy for the vaccines in question returned promising results for OMP prep material as a vaccine candidate, showing significant decreases in overall clinical signs, percent lung pathology, and mortality when compared to the control group. The modified live candidates showed a trend in reduction for these variables, however were not observed to be statistically significant in this study. The commercially available bacterin product showed no efficacy against respiratory challenge.

The lack of turbidity for the broth cultures during bacterial recovery may have been an artifact of the particular lot of media, or one of its components. The lack of turbidity did not correlate with an absence of H. somni detectable by PCR. The broth culture method may be abandoned for further work as the direct swab method showed the same level of H. somni recovery while reducing processing time by up to 72 hours.

While the OMP candidate looks promising, it should be noted that the OMP vaccine was generated from the Challenge Isolate (BIVI—Lg2-OK08), and the sarcosyl method of OMP preparation is not currently transferrable to mass production levels due to the high volume of culture needed to obtain the requisite amount of protein for vaccination and the use of ultracentrifugation in protein extraction. Alternative methods of extraction that are efficient for production (i.e.—higher protein yield with filter concentration or lower speed centrifugation) will need to be evaluated and efficacy of a heterologous OMP preparation should be examined.

Example 3

Efficacy of OMP Vaccine Prototypes Based on Protein Extraction Method

A. Objective

With the efficacy of a sarcosyl extracted OMP preparation from the challenge isolate (Lg2-OK08) observed in Study 2, it became important to evaluate a heterologous vaccine preparation. Isolates LgD1-TN08 and 156A2 were selected for this purpose. The sarcosyl method of OMP extraction utilized in Study 2 resulted in similar protein profiles for both soluble and insoluble fractions, indicating inefficiency in the process, and provided a lower than expected total protein yield. The efficacy of OMPs extracted using SDS and Triton-X, which unlike the sarcosyl method are scalable to mass production levels, were also examined.

B. Materials and Methods

Bacterial Isolates

H. somni isolates Lg2-OK08 (PTA-12755), LgD1-TN08 (PTA-127561), and 156A2 (BIVI) were utilized for this study. Culture growth and sarcosyl extraction of isolates Lg2-OK08 and LgD1-TN08 were identical to the method used in Study 2. For both isolates it was again noted that the sarcosyl method produced a relatively small amount of total protein, and that the majority of the final protein remained in the sarcosyl soluble fraction. Both the soluble and insoluble fractions were used for vaccine formulation. SDS extraction, as described in the next section was used for isolates LgD1-TN08 and Triton X was used for 156A2. The SDS method was carried out at a laboratory scale for isolate LgD1-TN08 and production scale Triton-X methods were used for isolate 156A2, which is used in a current vaccine product.

SDS Extraction

A method for Triton-X to extract outer-membrane proteins utilizing hollow fiber filtration was outlined by the BIVI production facility in Fort Dodge, Iowa. Briefly, live cultures are subjected to concentration by hollow fiber filtration (HFF) with a 0.2 um cutoff filter, resuspended, treated with Triton-X, and then returned to its original volume. The treated antigen is then subjected to a second round of HFF with a 5 kDa cutoff filter and concentrated to the desired protein load. Antigen from Isolate 156A2 generated at production scale by this facility was used to vaccinate one group.

A second group was vaccinated using SDS extracted material from research isolate LgD1-TN08. For this lab scale procedure, broth cultures of this isolate were prepared as described for the sarcosyl extraction method in Study 2, and harvested by centrifugation at 10,000×G for ten minutes rather than the 0.2 um HFF. Pellets were then resuspended at 10× concentration in 10 mM HEPES with protease inhibitor (Sigma). This suspension was then incubated at 60° C. for one hour. SDS was added at 0.04% total concentration and incubated at 41° C. for thirty minutes. The treated extract was then centrifuged at 9,500×G for twenty-four minutes to remove cell debris. The supernatant was then returned to 1× concentration using 10 mM HEPES with protease inhibitor and concentrated to 20× using hollow fiber filtration through a 5 kDa filter.

Calves

Seventy colostrum deprived, Holstein calves which tested as negative for persistent infection by BVDV by ear notch, M. bovis by q-PCR of nasal swabs, and which had not received any H. somni vaccination, were obtained from J&R Livestock (Iowa). Calf age ranged from 44 to 54 days at the time of first vaccination with a median age of 92 days at the time of challenge. All calves were determined to be in good health prior to the start of the study by the attending veterinarian on site at the BIVI research farm in Sioux Center, Iowa. Animals were fed a daily ration appropriate for their age and weight according to facility procedures. Water was available ad libitum by means of rubber containers available to each pen. The calves were randomly assigned to each of five groups and randomly assigned to a pen, arranged in groups of ten. One day prior to challenge all calves were randomly reassigned to a new pen to act as a stressor.

Vaccination and Challenge

All vaccine prototypes were formulated in Freund's Incomplete Adjuvant (Sigma) at a concentration of 400 ug protein per dose. Vaccines were administered in 2.0 mL SQ injections on Day 0 and Day 21 as was done for the OMP vaccine in the Study 2. Re-randomization of pen assignment occurred on Day 41, and challenge, identical to that in Study 2 was conducted on Day 42. The vaccination and challenge schedule are summarized in Table 6.

Clinical Observations

Clinical signs and rectal temperatures were observed daily for seven days following challenge. Although all body systems were observed, special attention was paid to signs of respiratory stress. Animals which showed signs of severe respiratory distress, became unable to stand, or could not reach food and/or water without assistance were euthanized for humane reasons and necropsied. All remaining animals were euthanized and necropsied at seven days post challenge. At the time of necropsy, gross pathology and the percentage of lessioning present in each lung lobe was recorded by the attending veterinarian. Samples of lung consisting of tissue from the margin of the lesion and good tissue were collected. Two samples were collected per calf and stored on ice until the time of delivery to the lab for testing. An additional sample from each calf was fixed in 10% formalin for histopathological examination.

TABLE 6

Experimental Design Group Treatments

| Groups | Animals/group | Vaccine | | | Challenge | | |
|---|---|---|---|---|---|---|---|
| | | Article | Dose/Route | Admin Schedule | Article | Dose/Route | Admin Schedule |
| Lg2-OK08 by Sarcosyl | 14 | OMP Prep | 2.0 mL SQ | Day 0 & Day 21 | Live H. somni Isolate Lg2-OK08 | 20.0 mL in RPMI 1640 @ 1.00 × 1010 CFU/dose Followed by 20.0 mL RPMI 1640 Wash | Day 42 |
| 156A2156A2 by Triton-X | 15 | OMP Prep | 2.0 mL SQ | | | | |
| LgD1-TN08 by Sarcosyl | 14 | OMP Prep | 2.0 mL SQ | | | | |
| LgD1-TN08 by SDS | 14 | OMP Prep | 2.0 mL SQ | | | | |
| Control | 14 | Sterile PBS | 2.0 mL SQ | | | | |

Bacterial Recovery

As was done in Example 2, post-necropsy lung samples were frozen at −70° C. and thawed prior to processing. Thawed samples were seared over an open flame, moved to a sterile environment, incised, and the internal surface was swabbed. The swab was used to streak CBA plates (Remel) which were incubated overnight at 37° C. with 10% $CO_2$ to verify the absence of extraneous agents. The swabs were then subjected to DNA extraction and PCR to verify the presence of H. somni.

PCR

To verify the presence of H. somni from swabs of infected lungs, the swabs were subjected to DNA extraction (Qiagen DNA kit) and tested for presence of H. somni DNA by q-PCR using primers specific for the H. somni 16S gene as described for Study 1. PCR was carried out in a 96-well format in 25 uL volumes using a CFX-96 Thermocycler (Bio-Rad) with Bio-Rad Master Mix, 0.4 ug/uL Bovine Serum Albumin (BSA), and a set of In-Process Control Primers to verify the validity of the reaction in each well. A standard curve of H. somni DNA was run on each plate. An initial activation step at 95.0° C. for five minutes was performed, followed by forty-five cycles of denaturing at 95.0° C. for fifteen seconds and annealing/elongation step at 60.0° C. for thirty seconds with a real-time capture of probe fluorescence at the end of each cycle. Data was captured and analyzed using the Bio-Rad CFX software. Samples were run in duplicate and mean threshold cycle ($C_t$) was compared to the standard to determine whether each sample was positive or negative. In the event that a sample had one positive and one negative well, the sample was re-run in triplicate with final determination of positivity determined by which result was represented in >50% of the tested wells.

Histopathology

Lung samples fixed in 10% formalin were transported to the ISU-VDL in Ames, Iowa for histopathological examination. A scoring system of 0-4 was used. A score of 0 indicated no microscopic lesions, 1 indicated mild or focal lesions, 2 designated moderate or multi-focal lesions, 3 designated severe or diffuse microscopic lesions, and 4 designated severe, diffuse microscopic lesions.

Results

Figure 5:
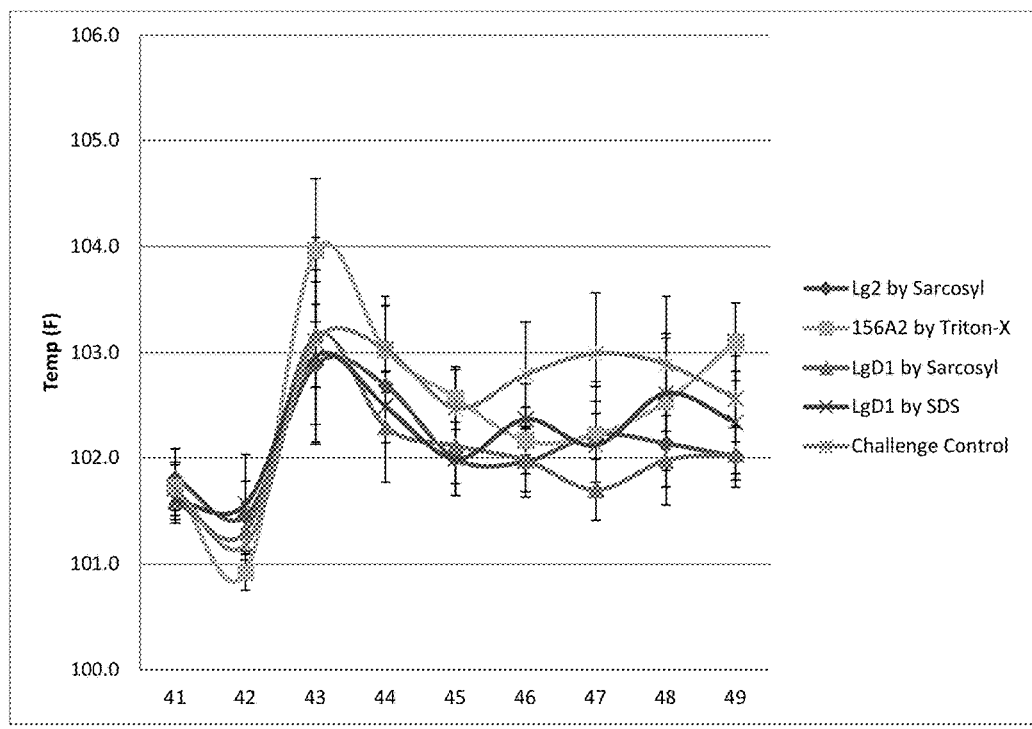
FIG. 5. is a graph illustrating mean rectal temperature by treatment group. Baseline rectal temperatures were obtained by observation both one day prior, and then immediately preceding challenge on Days −41 and 42. Rectal temperatures were recorded daily following challenge and continued until final necropsy occurred on Day 49. Error bars represent confidence with $\alpha=0.1$.

Rectal temperatures for all groups increased by approximately three degrees on the day following challenge (Day 43). The highest peak temperature was observed in the group vaccinated with Triton-X extracted Isolate 156A2, reaching ~104.0° F. one day following challenge. While significant differences in temperature were observed on individual days for some vaccine groups when compared to the challenge controls, these observations do not appear to be biologically significant as an indicator of protection as these differences were observed from groups regardless of their observed reduction in percentage of lung pathology. Rectal temperatures are summarized in FIG. 5.

The previous study indicated direct q-PCR of swabs from frozen and thawed lung tissue would allow for successful detection of H. somni from these samples. The number of samples allowing for successful detection was lower in the current study, as was the number of samples providing viable H. somni for culture growth. While it is beyond the scope of this study to determine the cause of this observation, it may indicate an increase in clearing of infection due to vaccine administration. Significant differences were not noted among groups, but a higher level of detection and recovery was observed in groups that lacked any observed vaccine efficacy. This parameter will continue to be examined in further studies. H. somni recovery is described in Table 7.

TABLE 7

*H. somni* Detection from Challenged Animals

| Bacterial Detection Technique | Treatment Group | | | | | Lung Sample Total by Detection Technique |
|---|---|---|---|---|---|---|
| | Lg2-OK08 by Sarcosyl | 156A2 by Triton-X | LgD1-TN08 by Sarcosyl | LgD1-TN08 by SDS | Challenge Control | |
| Frozen Lung Plate | 9/14 (64.3%) | 8/15 (53.3%) | 5/14 (35.7%) | 8/14 (57.1%) | 8/13 (61.5%) | 38/70 (54.3%) |
| Frozen Lung Swab | 8/11 (72.7%) | 13/15 (86.7%) | 9/14 (64.3%) | 11/14 (78.6%) | 11/13 (84.6%) | 52/70 (74.3%) |
| Lung Sample Total By Treatment Group | 17/25 (68.0%) | 21/30 (70.0%) | 14/28 (50.0%) | 19/28 (67.9%) | 19/26 (73.1%) | |

Observed clinical signs were noted beginning one day post challenge and included depression, decreased appetite, rapid and/or labored respiration, and coughing. A serous nasal discharge was noted for a few animals beginning three days post challenge. Clinical signs for all groups lasted throughout the challenge period. No significant differences were noted among groups in regards to any individual sign, or total number of signs displayed.

Three animals in the control group died prior to the end of the challenge period. Four animals in the 156A2 group, two animals in the LgD1-TN08 OMP by sarcosyl group, and three animals in the LgD1-TN08 OMP by SDS group also died during the course of the challenge period. No animals receiving the Lg2-OK08 OMP by sarcosyl vaccine died prior to necropsy. Any difference in comparison to the challenge control group was not statistically significant. Mortality is summarized in Table 8.

TABLE 8

Mortality by Treatment Group

| Tx | Day 42 | Day 43 | Day 44 | Day 45 | Day 46 | Day 47 | Total Mortality |
|---|---|---|---|---|---|---|---|
| Lg2-OK08 by Sarcosyl | 0/14 (0.00%) | 0/14 (0.00%) | 0/14 (0.00%) | 0/14 (0.00%) | 0/14 (0.00%) | 0/14 (0.00%) | 0/14 (0.00%) |
| 156A2 by Triton-X 100 | 0/15 (0.00%) | 1/15 (6.7%) | 1/15 (6.7%) | 0/15 (0.0%) | 1/15 (6.7%) | 1/14 (6.7%) | 4/14 (26.7%) |
| LgD1-TN08 by Sarcosyl | 0/14 (0.00%) | 0/14 (0.00%) | 1/14 (7.1%) | 1/14 (7.1%) | 0/14 (0.0%) | 0/14 (0.0%) | 2/14 (14.3%) |
| LgD1-TN08 by SDS | 0/14 (0.00%) | 1/14 (7.1%) | 1/14 (7.1%) | 1/14 (7.1%) | 0/14 (0.0%) | 0/14 (0.0%) | 3/14 (21.4%) |
| Challenge Control | 0/14 (0.00%) | 2/13 (15.4%) | 0/13 (0.0%) | 1/13 (7.7%) | 0/13 (0.0%) | 0/13 (0.0%) | 3/13 (23.1%) |

Mortality is reported as the number of deaths in each group on each day that such events were observed. Percentages represent the proportion of the treatment group affected.

Figure 6:
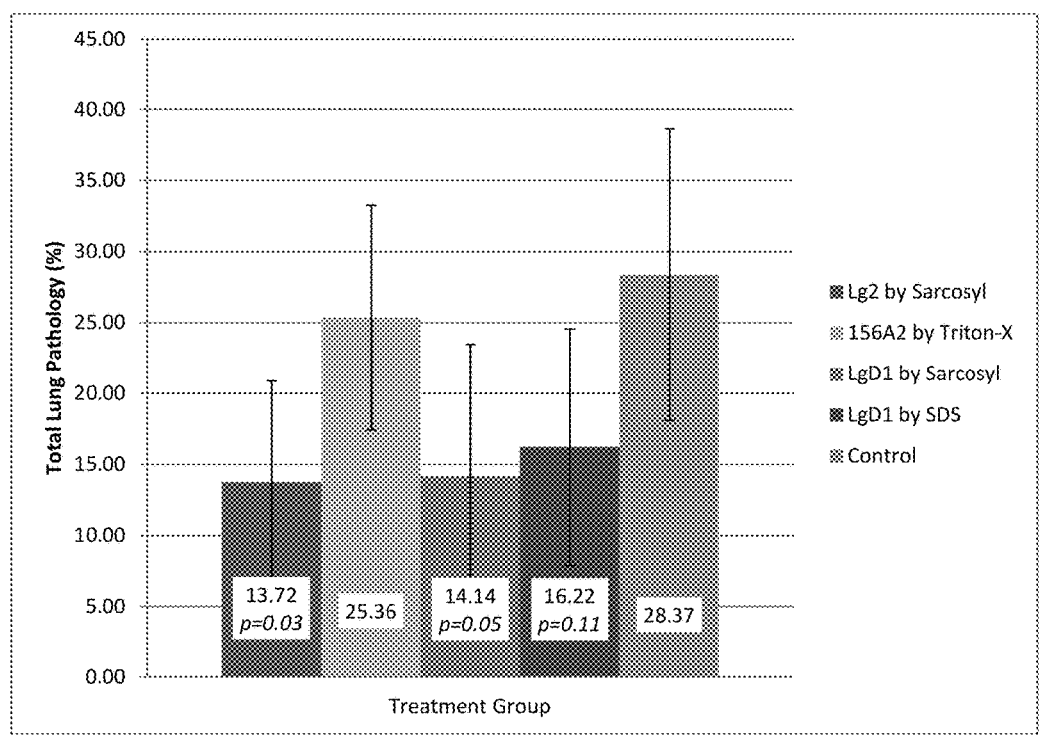
FIG. 6. is a graph illustrating total lung pathology. Percentage of lung involvement was determined by the attending site veterinarian's observation and palpation of each lobe. Total percentage was calculated using the method described by Jericho and Langford (1982). Error bars represent confidence with $\alpha=0.1$. Sarcosyl extracted vaccines produced significant reductions in pathology when compared to the non-vaccinated controls when prepared from isolate Lg2-OK08 (p=0.03) and LgD1-TN08 (p=0.05). SDS extraction of isolate LgD1-TN08 produced a reduction of lung pathology, but this was not statistically significant (p=0.11). Triton X extraction of 156A2 showed no difference in pathology when compared to the control group.

Vaccines consisting of OMPs generated by sarcosyl extraction of both Isolate Lg2-OK08 (13.72%, p=0.045) and Isolate LgD1-TN08 (14.14%, p=0.037) showed significant reduction in total lung pathology when compared to the challenge control group (28.37%). The OMP vaccine generated using SDS extraction of Isolate LgD1-TN08 (16.22%, p=0.114) showed a similar trend in reduction of the average lung pathology observed for the group. However due to variation within the group lesion scores were not observed to be significantly different from the challenge control group. The 156A2 antigen extracted by Triton X 100 (25.36%, p=0.814) showed no difference in lung pathology when compared to the challenge control group. Percentage of lung pathology is summarized in FIG. 6.

Histological examination of lung tissues was consistent with bacterial pneumonia. Presence of airway plugs, edema, pleuritis, necorsis, and atelectasis was also reported in animals in all groups, but were most severe in the challenge control group. The presence of these findings in vaccinate groups is expected as samples for this examination were taken from lesion margins. This gives no indication of overall pathology observed in individual animals and should only be taken to indicate that the challenge was again successful.

C. Conclusion

A two dose vaccination with material prepared by sarcosyl extraction from *H. somni* isolates either homologous (Lg2-OK08, p=0.045) or heterologous (LgD1-TN08, p=0.037) to the challenge isolate showed a significant decrease in total lung pathology when compared to challenge control animals. The same vaccination schedule using an SDS extraction of heterologous isolate LgD1-TN08 showed a similar decrease in total lung pathology, but due to variability within the group was not observed to be significant (p=0.114) in this study. The 156A2 antigen, prepared by Triton-X extraction, showed no difference in total lung pathology when compared to the control group (p=0.814). Total lung pathology continues to be the most relevant parameter for comparison of efficacy. It should also be noted that the 400 ug of protein per dose used in this study is below the potency criteria for the actual commercial vaccine in with the 156A2 antigen is used. Increasing the protein concentration or using conventional, more immuno-competent calves could alter the results observed in this study.

The vaccines derived from sarcosyl extracted material have been formulated using a combination of sarcosyl insoluble pellets as well as sarcosyl soluble supernatants as protein yields within the pellet themselves have been insufficient for vaccination. Western blot analysis showed that immunoreactive proteins of similar molecular weight exist in both fractions. Further work should be completed to improve the efficiency of this process in an attempt to increase total protein yield and to increase the amount of protein deposited in the insoluble pellet. The methods of sonication and centrifugation for this extraction method may be possible points for improvement.

The SDS extraction method is more efficient, but produces a different protein profile when separated by SDS-PAGE and subjected to western blot analysis. While similar bands to the sarcosyl preparation can be observed, they are much more dilute in the total preparation and several other proteins of unknown importance are also observed. This may account for the observed decrease in lung pathology in animals receiving an SDS extract vaccination, but also the variability of success within the group.

While Study 2 also showed a significant decrease in observed depression, labored respiration, total clinical signs, and mortality when using the homologous sarcosyl extraction vaccine (Lg2-OK08), this was not seen in the current study. The group receiving the sarcosyl extraction of Lg2-OK08 did not display any mortality in the current study, which is consistent with previous observations. All other study groups showed a mortality rate between 14.3% (sarcosyl extraction of LgD1-TN08) and 26.7% (Triton-X extraction of 156A2) following challenge. While clinical signs are not currently a primary parameter for vaccine comparison in these studies, production of consistent clinical signs and mortality would be beneficial for any future work involving vaccine comparisons.

Other parameters examined included rectal temperatures, *H. somni* recovery by culture and q-PCR, and a comparison of injection site reactions. None of these showed any significant differences among groups. It is not unexpected to have similar recoveries and PCR detection as the purpose of those tests is for confirmation of the presence of *H. somni* in the lesions regardless of their percentage lesion involvement. While *H. somni* recovery was lower than observed in previous studies, it was lower for all groups suggesting that the challenge was consistent across groups. While Study 2 indicated that freezing of the fresh lung samples did not affect *H. somni* recovery, it is possible that the freeze/thaw had a negative impact on recovery. Therefore it is recommended that future studies use swabs of fresh (not frozen) lungs when possible for successful recovery of bacteria from lung tissue. It is important to note that while q-PCR is utilized for detection, the results are to be interpreted qualitatively for presence or absence, and the $C_t$ values are not an accurate quantitative measure for the amount of bacteria detected as the assay has not been validated.

Example 4

Efficacy for Extracted OMP Fractions by Sarcosyl and SDS Methods

D. Objective

Sarcosyl extracted OMP vaccines continued to show significant reductions in lung lobe pathology caused by respiratory challenge in Study 3, however the extraction process itself continued to be inefficient. By modifying the sonication step to improve cell lysis and the centrifugation steps to improve the separation of soluble and insoluble fractions, both a higher total yield and a higher concentration of protein in the final insoluble fraction were achieved. As the previous efficacy had been based on vaccination predominantly consisting of the insoluble fraction, it was important to examine the efficacy of these fractions separately. Also the SDS extraction method produced an obvious reduction in total lung scores in Study 3, however this was not found to be statistically significant. It was deemed important to retest this vaccine candidate.

E. Materials and Methods

Bacterial Isolates

Isolate LgD1-TN08 was utilized to prepare all vaccine prototypes for this study. Culture growth and SDS extraction method for this isolate were identical to procedures used in Study 3. Changes to the sacrosyl extraction method for this isolate are described below. Isolate Lg2-OK08 was utilized to prepare challenge material for this study. Growth, harvest, and preparation for of challenge material were identical to the procedure used in all previous studies.

Sarcosyl Extraction

The sarcosyl extraction method for this study was modified in an attempt to increase total protein yield, and to increase the efficiency of separating insoluble proteins in the final preparation. To increase total protein yield, sonication was completed using a probe inserted directly into the culture rather than using the cup-horn as was done previously. This resulted in improved cell lysis, releasing more membrane bound proteins into the supernatant following the 17k×G centrifugation step as confirmed by BSA Total Protein Assay (Thermo) comparing protein concentrations in the supernatants of both preparation methods (data not shown). To improve the efficiency of insoluble protein separation, all steps requiring ultracentrifugation were conducted using a 70Ti fixed angle rotor rather than the SW28 swinging bucket rotor that had been used previously. The fixed angle rotor allowed for more efficient sedimentation. These two modifications resulted in the desired effects. Sufficient protein yield was obtained for formulations of separate vaccines using only the sarcosyl insoluble fraction or only sarcosyl soluble fraction. A combination of the two fractions was also prepared to allow for comparison to the vaccine preparation that was used in the previous studies.

Calves

Sixty-eight colostrum deprived calves which tested as negative for persistent infection by BVDV by ear notch, *M. bovis* by q-PCR of nasal swabs, and which had not received any *H. somni* vaccination, were obtained from J&R Livestock (Iowa). Calf age ranged from 36 to 50 days at the time of first vaccination with a median age of 90 days at the time of challenge. All calves were determined to be in good health prior to the start of the study by the attending veterinarian on site at the BIVI research farm in Sioux Center, Iowa. Animals were fed a daily ration appropriate for their age and weight according to facility procedures. Water was available ad libitum by means of rubber containers available to each pen. The calves were randomly assigned to each of five groups and randomly assigned to a pen, arranged in groups of ten. One day prior to challenge all calves were randomly reassigned to a new pen to act as a stressor.

Vaccination and Challenge

Vaccinations were administered SQ in 2.0 mL doses containing 400 ug of total protein on Days 0 and 21. The Challenge Control Group received similar injections containing Sterile PBS (Gibco) and Freund's Incomplete Adjuvant (Sigma) only. Challenge occurred on Day 42 and consisted of a fresh culture of *H. somni* isolate Lg2-OK08 diluted in RPMI-1640 Media with 5% FBS to contain $1.0 \times 10^9$ CFU/mL administered intratracheally via endoscope in a 20.0 mL volume, followed by a 20.0 mL wash with RPMI-1640 Media with 5% FBS. The vaccination and challenge schedule along with group size and dosing are described in Table 9.

Clinical Observations

Clinical signs and rectal temperatures were observed daily for seven days following challenge. Although all body systems were observed, special attention was paid to signs of respiratory stress. Animals which showed signs of severe respiratory distress, became unable to stand, or could not reach food and/or water without assistance were euthanized for humane reasons and necropsied. All remaining animals were euthanized and necropsied at seven days post challenge. At the time of necropsy, gross pathology and the percentage of lessioning present in each lung lobe was recorded by the attending veterinarian. Samples of lung consisting of tissue from the margin of the lesion and good tissue were collected. Two samples were collected per calf and stored on ice until the time of delivery to the lab for testing. An additional sample from each calf was fixed in 10% formalin for histopathological examination.

(Bio-Rad) with Bio-Rad Master Mix, 0.4 ug/uL Bovine Serum Albumin (BSA), and a set of In-Process Control Primers to verify the validity of the reaction in each well. A standard curve of *H. somni* DNA was run on each plate. An initial activation step at 95.0° C. for five minutes was performed, followed by forty-five cycles of denaturing at 95.0° C. for fifteen seconds and annealing/elongation step at 60.0° C. for thirty seconds with a real-time capture of probe fluorescence at the end of each cycle. Data was captured and analyzed using the Bio-Rad CFX software. Samples were run in duplicate and mean threshold cycle ($C_t$) was compared to the standard to determine whether each sample was positive or negative. In the event that a sample had one positive and one negative well, the sample was re-run in triplicate with final determination of positivity determined by which result was represented in >50% of the tested wells.

Histopathology

Lung samples fixed in 10% formalin were evaluated for histopathological examination. A scoring system of 0-4 was used. A score of 0 indicated no microscopic lesions, 1 indicated mild or focal lesions, 2 designated moderate or multi-focal lesions, 3 designated severe or diffuse microscopic lesions, and 4 designated severe, diffuse microscopic lesions.

TABLE 9

Experimental Design Group Treatments

| | | Vaccine | | | Challenge | | |
|---|---|---|---|---|---|---|---|
| Groups | Animals/group | Article | Dose/Route | Admin Schedule | Article | Dose/Route | Admin Schedule |
| Insoluble LgD1-TN08 OMPs | 14 | Sarcosyl Insoluble Fraction | 2.0 mL SQ | Day 0 & Day 21 | Live *H. somni* Isolate Lg2-OK08 | 20.0 mL in RPMI 1640 @ 1.00 × 1010 CFU/dose Followed by 20.0 mL RPMI 1640 Wash | Day 42 |
| Soluble LgD1-TN08 OMPs | 14 | Sarcosyl Soluble Fraction | 2.0 mL SQ | | | | |
| Soluble, Insoluble LgD1-TN08 OMP Combination | 13 | Sarcosyl Soluble and Sarcosyl Insoluble Fractions | 2.0 mL SQ | | | | |
| SDS Extracted LgD1-TN08 OMP | 13 | SDS Extraction | 2.0 mL SQ | | | | |
| Challenge Control | 13 | Sterile PBS and Freund's Incomplete Adjuvant | 2.0 mL SQ | | | | |

Bacterial Recovery

Post-necropsy lung samples were stored at 4° C. until they could be processed. These samples were seared over an open flame, moved to a sterile environment, incised, and the internal surface was swabbed. The swab was used to streak CBA plates (Remel) which were incubated overnight at 37° C. with 10% $CO_2$ to verify the absence of extraneous agents. The swabs were then subjected to DNA extraction and PCR to verify the presence of *H. somni*.

PCR

To verify the presence of *H. somni* from swabs of infected lungs, the swabs were subjected to DNA extraction (Qiagen DNA kit) and tested for presence of *H. somni* DNA by q-PCR using primers specific for the *H. somni* 16S gene as described for Study 1. PCR was carried out in a 96-well format in 25 uL volumes using a CFX-96 Thermocycler Results Rectal temperatures for all treatment groups were again observed to increase by approximately three degrees on the day following challenge. The non-vaccinated control group was observed to maintain the highest average rectal temperature over the course of the challenge phase. All vaccinate groups showed a decrease in mean rectal temperature over the same time frame, however the groups vaccinated with either a combination of sarcosyl extracted fractions, or with an SDS extract were more pronounced and consistent in their reduction of mean rectal temperatures. Rectal temperature observations are summarized in FIG. 7.

Recovery of *H. somni* from fresh lung tissue was increased over that observed in the previous study when frozen samples were utilized. No significant difference was noted among treatment groups, although viable recovery was highest in the un-vaccinated control group. These observations are summarized in Table 10.

TABLE 10

H. somni Detection from Challenged Animals

| Bacterial Detection Technique | LgD1-TN08 by Sarcosyl (insoluble) | LgD1-TN08 by Sarcosyl (soluble) | LgD1-TN08 by Sarcosyl (combo) | LgD1-TN08 by SDS | Challenge Control | Lung Sample Total by Detection Technique |
|---|---|---|---|---|---|---|
| Fresh Lung Culture | 8/13 (61.5%) | 6/13 (46.2%) | 9/14 (64.3%) | 7/14 (50.0%) | 9/14 (64.3%) | 39/68 (57.4%) |
| Fresh Lung Swab PCR | 11/13 (84.6%) | 12/13 (92.3%) | 13/14 (92.9%) | 10/14 (71.4%) | 14/14 (100.0%) | 60/68 (88.2%) |
| Lung Sample Total By Treatment Group | 19/26 (73.1%) | 18/26 (69.2%) | 22/28 (78.6%) | 17/28 (60.7%) | 23/28 (82.1%) | |

Percentages indicate the proportion of each group which provided successful detection of H. somni by q-PCR specific for the 16s rRNA gene.

TABLE 5.3

Mortality by Treatment Group

| Tx | Day 42 | Day 43 | Day 44 | Day 47 | Total Mortality |
|---|---|---|---|---|---|
| LgD1-TN08 Sarcosyl Insoluble | 0/13 (0.00%) | 0/13 (0.00%) | 1/13 (7.69%) | 0/13 (0.00%) | 1/13 (7.69%) |
| LgD1-TN08 Sarcosyl Soluble | 0/13 (0.00%) | 0/13 (0.00%) | 0/13 (0.00%) | 0/13 (0.00%) | 0/13 (0.00%) |
| LgD1-TN08 Sarcosyl Combo | 0/14 (0.00%) | 0/14 (0.00%) | 2/14 (14.3%) | 0/14 (0.00%) | 2/14 (14.3%) |
| LgD1-TN08 by SDS | 0/14 (0.00%) | 0/14 (0.00%) | 0/14 (0.00%) | 1/14 (7.1%) | 1/14 (7.1%) |
| Challenge Control | 0/14 (0.00%) | 1/14 (7.1%) | 3/14 (21.4%) | 0/14 (0.00%) | 4/14 (28.6%) |

Mortality is reported as the number of deaths in each group on each day that such events were observed.
Percentages represent the proportion of the treatment group affected. No animals died on Days 45, 46, or 48.

Common clinical signs observed in the previous studies included respiratory difficulties, coughing, depression, and anorexia. For the current study these four parameters were normalized on scales of 0-3 indicating the severity of the sign on a given day. The highest number of clinical signs and the highest severity were observed in the control group. Due to the ordinal nature of the scoring system, no statistically significant differences were noted among groups.

Four animals in the control group died prior to the end of the challenge period. One animal in the sarcosyl pellet group, two animals in the sarcosyl combination group, and one animal in the SDS group also died during the course of the challenge period. No animals receiving the sarcosyl supernatant vaccine died prior to necropsy. Any difference in comparison to the challenge control group was not statistically significant. Mortality is described in Table 11.

TABLE 11

Mortality by Treatment Group

| Tx | Day 42 | Day 43 | Day 44 | Day 47 | Total Mortality |
|---|---|---|---|---|---|
| LgD1-TN08 Sarcosyl Insoluble | 0/13 (0.00%) | 0/13 (0.00%) | 1/13 (7.69%) | 0/13 (0.00%) | 1/13 (7.69%) |
| LgD1-TN08 Sarcosyl Soluble | 0/13 (0.00%) | 0/13 (0.00%) | 0/13 (0.00%) | 0/13 (0.00%) | 0/13 (0.00%) |
| LgD1-TN08 Sarcosyl Combo | 0/14 (0.00%) | 0/14 (0.00%) | 2/14 (14.3%) | 0/14 (0.00%) | 2/14 (14.3%) |
| LgD1-TN08 by SDS | 0/14 (0.00%) | 0/14 (0.00%) | 0/14 (0.00%) | 1/14 (7.1%) | 1/14 (7.1%) |
| Challenge Control | 0/14 (0.00%) | 1/14 (7.1%) | 3/14 (21.4%) | 0/14 (0.00%) | 4/14 (28.6%) |

Mortality is reported as the number of deaths in each group on each day that such events were observed.
Percentages represent the proportion of the treatment group affected. No animals died on Days 45, 46, or 48.

Figure 8:
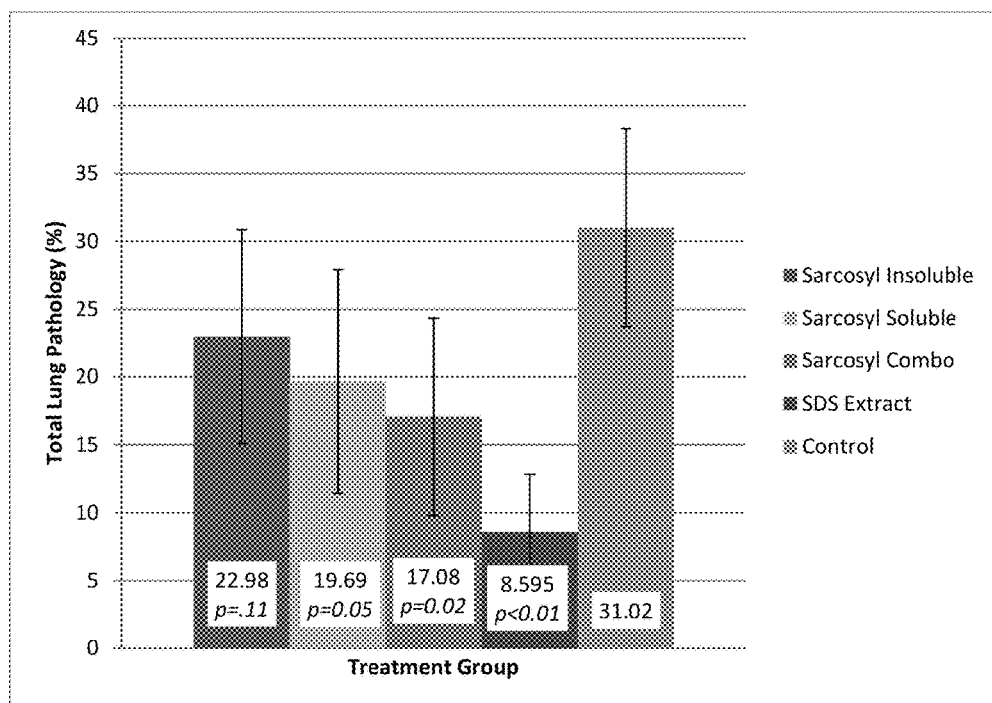
FIG. 8. is a graph illustrating total percent lung pathology. Percentage of lung involvement was determined by the attending site veterinarian's observation and palpation of each lobe. Total percentage was calculated using the method described by Jericho and Langford (1982). Error bars represent confidence intervals with $\alpha=0.1$ The sarcosyl insoluble vaccine prototype was the only treatment to not significantly reduce lung pathology when compared to the non-vaccinated control group (p=0.11). Vaccines containing either sarcosyl soluble material or consisting of SDS extracted material provided a significant reduction in observed pathology.

The primary parameter for comparison of vaccine efficacy for this study remains the percent lung lobe pathology. One animal vaccinated with the sarcosyl insoluble fraction was found to be lacking the right cranial lobe. As this lobe was simply not present due to an anatomically anomaly, and a complete score could not be given, the animal was removed from analysis. Non-vaccinated controls had a mean lung pathology score of 31.02%. Significant reduction in lung pathology was achieved by vaccination with sarcosyl soluble supernatant (19.70%, $p=0.05$), a combination of sarcosyl soluble and sarcosyl insoluble fractions (17.08%, $p=0.02$), or SDS extracted OMP's (8.60%, $p<0.01$). Vaccination with sarcosyl insoluble pellet material showed a slight decrease in, but did not produce a significant reduction in lung pathology (22.98%, $p=0.11$). This data is summarized in FIG. 8.

Samples were again submitted for histopathological examination. Observations of airway plugs, interlobular edema, necrosis, and atelectasis; all consistent with bacterial pneumonia were again observed in animals across all groups, however were determined to be most severe in the challenge control group, and least severe in the SDS extracted OMP vaccinates.

Conclusion

A two-dose vaccination of OMP material containing either sarcosyl soluble material or extracted using SDS provided a statistically significant reduction in total lung pathology when compared to non-vaccinated controls. Animals which received vaccination with sarcosyl insoluble material only, showed a decrease in total lung pathology, but this was not found to be statistically significant.

Detection of *H. somni* by q-PCR and recovery of viable *H. somni* by culturing of lung samples were both more effective in the current study when compared to Example 3.

In the current study lung samples were maintained at 4° C. rather than being frozen prior to lab procedures. No significant differences were noted among groups in detection or viable recovery; however both were highest in the non-vaccinated group.

Clinical signs of disease including rectal temperature, respiratory difficulty, coughing, depression, and anorexia were recorded daily during the challenge phase of the study. Vaccination with SDS extracted antigens resulted in significantly lower rectal temperatures beginning on Day 44 (two days following challenge) when compared to the non-vaccinated control group, and continuing through the termination of the study on Day 49. No other significant differences were noted among groups when comparing presence or severity of the clinical signs observed.

This data set indicates that both the SDS and sarcosyl extraction methods yield proteins which provide an efficacious immune response against a respiratory challenge with *H. somni*. The lack of efficacy for the sarcosyl insoluble fraction indicates that something is preserved in the soluble fraction which is necessary for the efficacy observed in this, as well as previous studies. Whether this is a specific protein, a non-protein component of the LOS or the sarcosyl itself remains to be determined. Western blot analysis will be utilized to determine if specific immunoreactive proteins can be identified that are unique to either of the sarcosyl fractions or the SDS extract.

Example 5

Serological ELISA to Monitor Bovine Anti-*H. somni* Titers

A. Objective

While it is important to compare the final pathology scores as the primary parameter among treatment groups, this gives no indication as to what immune response is actually taking place within the animal during the course of vaccination and challenge. As an MHCII response is anticipated, measurement of IgG activity would be prudent. By developing a serological ELISA capable of detecting changes in antibody response over time it would be possible to determine the importance of the humoral response in relation to the administered vaccines.

B. Materials and Methods

Coating Antigen

*H. somni* Isolate Lg2-OK08 has been used for challenge purposes in the preceding studies. It is therefore important to note the antibody response towards this isolate generated by the vaccines administered prior to challenge. To do so a culture of this isolate was grown in broth as described previously. Harvest was completed by centrifugation at 10,000×G for ten minutes and followed by three washes in PBS (Gibco) in which the pellets were brought back to 3× concentration in PBS and centrifuged at 10,000×G for ten minutes. Following the final PBS wash, the culture was resuspended at 3× concentration in 10 mM HEPES with protease inhibitors.

Serum Samples

Serum was collected weekly from each animal in the previous studies and was stored at −40° C. in ~2.0 mL volumes per sample. Serum pools for each group were generated by combining 100 uL of serum from each animal in the group for each time point.

ELISA

Experiments were completed with assumed positive and negative serum samples (Control animals at Day 0 for negative, and Lg2-OK08 Sarcosyl OMP vaccinates at Day 41 for positive) which determined the appropriate reagent concentrations to be used. The concentrations reported ensure that readings represent data from the linear portion of the dilution curve.

Lg2-OK08 derived 3× coating antigen (prepared as described above) was diluted in Carbonate Coating Buffer (Sigma) to 1:300 and added at 100 uL per well of a 96-well Medium-binding microtiter plate (Greiner) and incubated at 37° C. for two hours. Unbound antigen was washed away by three washes of TBS+Tween 20 (BIVI) using a microtiter plate washer (Dynex). Unoccupied area of the wells was then blocked by addition of 250 uL of Protein Free Blocking Buffer (Thermo) and incubated at 37° C. for one hour followed by another wash step. Serum Pools for each group at each time point (Studies 2 and 3), or serum from individual animals (Study 4) were then diluted to 1:1,600 in Blocking Buffer and added to duplicate wells on the plate in 100 uL volumes and incubated for one hour at 37° C. followed by another was step. A rabbit-anti-bovine horse radish peroxidase conjugate (Jackson Immunolabs) was then diluted 1:10,000 in Blocking Buffer, added at 100 uL per well, incubated at 37° C. for forty-five minutes, and excess washed away. Wells were developed using Sureblue 1-Component Substrate (KPL) by addition of 100 uL per well and incubation at room temperature for 6 minutes at which point 100 uL of 1N HCl was added to stop the reaction. Absorbances were read at 450 nm using a SpectraMax M5 spectrophotometer (Molecular Devices). Each plate contains a negative serum standard and a positive serum standard to allow for comparison among plates as well as no antigen and no serum control wells to ensure no increase in background signal among plates. Absorbance data was transformed to a "signal to noise" ratio by dividing the mean absorbance for each sample by the mean absorbance for the negative serum standard.

C. Results

Example 2

Figure 9:
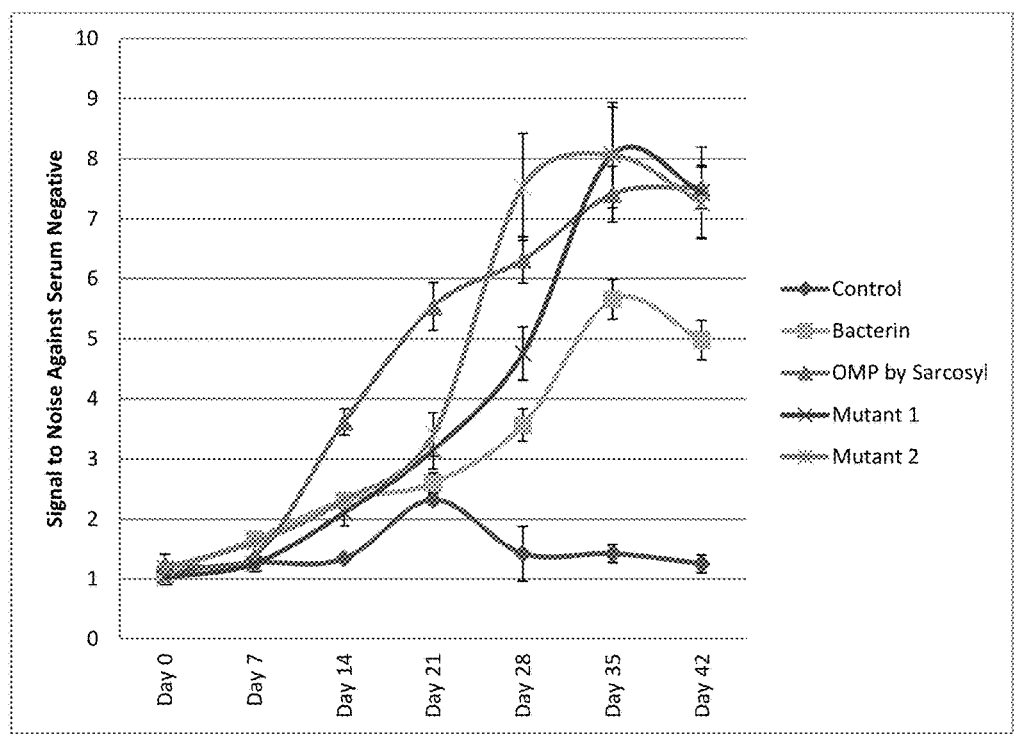
FIG. 9. is a graph illustrating ELISA results for *H. somni* IgG over the Vaccination Phase. S:N Ratio calculated by dividing the mean $A_{450}$ of duplicate samples by the mean $A_{450}$ of the serum negative control on each plate allowing for comparison among assays. Data represents duplicate samples run in three assays, completed on separate days (6 replicates for each sample). Error bars indicate confidence with $\alpha=0.1$.

All vaccine treatments used within this study produced an increase in IgG response over the course of vaccination. The group vaccinated with a commercially available bacterin produced the least prevalent response, while animals vaccinated with the modified live deletion mutants produced the highest level of IgG response. The OMP vaccinated group was the fastest to produce an IgG response. The detected levels of IgG for the modified live groups and the OMP group were nearly identical at the time of challenge on Day 42. non-vaccinated controls produced no detectible increase in antibody production, but a small increase was observed on Day 28 with an undetermined source. This increase was not observed at later dates in the study. This data is summarized in FIG. 9.

Example 3

Figure 10:
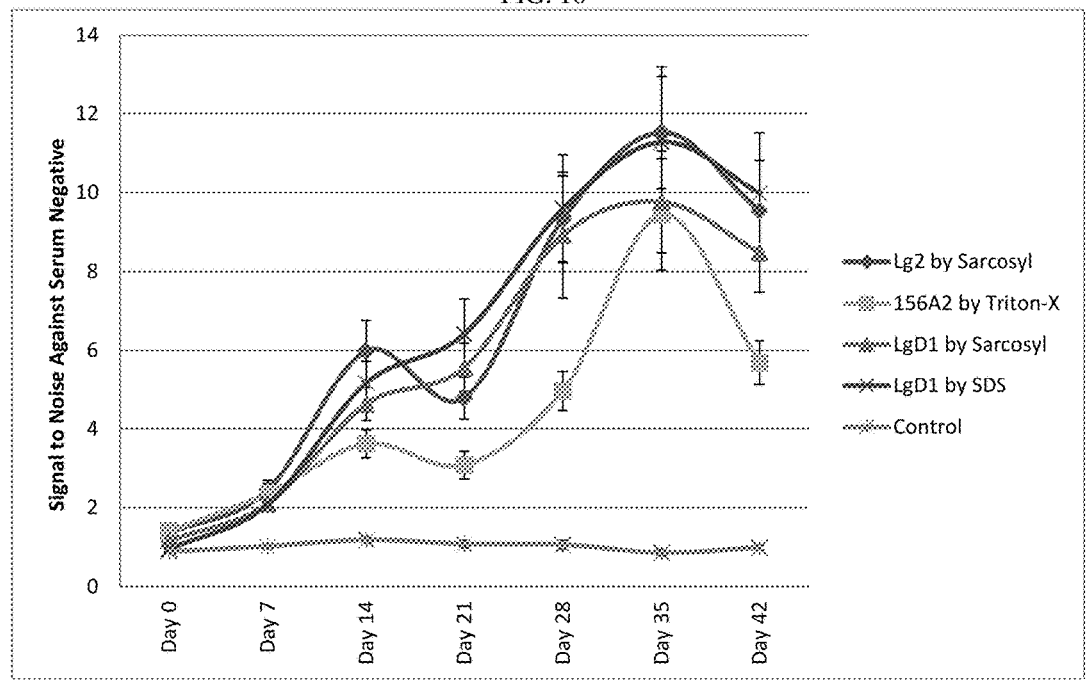
FIG. 10. is a graph illustrating ELISA results for *H. somni* IgG over the Vaccination Phase. S:N Ratio calculated by dividing the mean $A_{450}$ of duplicate samples by the mean $A_{450}$ of the serum negative control on each plate allowing for comparison among assays. Data represents duplicate samples run in three assays, completed on separate days (6 replicates for each sample). Error bars indicate confidence with $\alpha=0.1$.

All vaccines used in this study again produced a detectable increase in IgG over the course of vaccination. These levels peaked at Day 14 and declined at Day 21, and then were sharply increased following revaccination on that day. A peak was again observed at Day 35, with a small drop off before challenge on Day 42. The sarcosyl extracted OMP from the challenge isolate Lg2-OK08 produced the highest IgG response, while the 156A2 Triton X vaccine produced the lowest. Responses from animals vaccinated with preparations from Isolate LgD1-TN08 were similar. Non-vaccinated animals displayed no detectable increase in IgG levels over the course of vaccination. This data is summarized in FIG. 10.

Example 4

Figure 11:
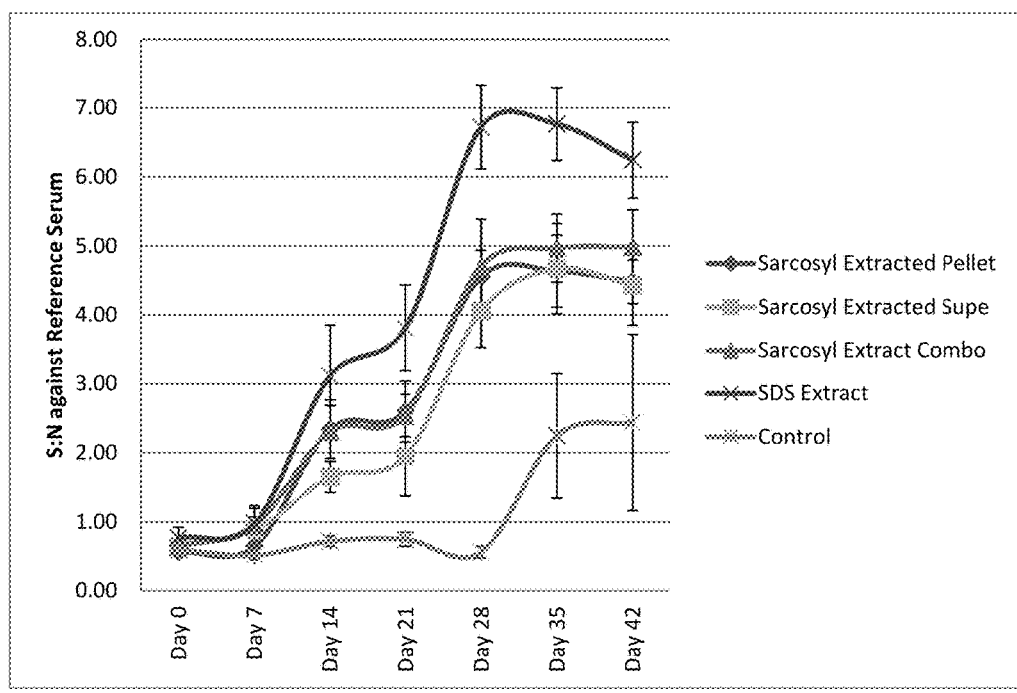
FIG. 11. is a graph illustrating ELISA results for *H. somni* IgG over the Vaccination Phase. S:N Ratio calculated by dividing the mean $A_{450}$ of duplicate samples by the mean $A_{450}$ of the serum negative control on each plate allowing for comparison among assays. For this assay serum samples for each individual animal on each study day were tested allowing for determination of a confidence interval at $\alpha=0.1$ (represented by error bars). S:N for Study 4 was lower than those observed in Study 2 and 3. This could be attributed to generation of frozen stocks for all reagents and control samples between testing for these studies.

Vaccinates in this study produced similar results to the previous studies with less pronounced peaks that was observed in Study 2011034. The SDS extract group produced the highest IgG response, while all sarcosyl treatments produced similar results. The non-vaccinated control group displayed an increase in IgG response beginning on Day 35 and continued through Day 42. Upon further review, this increase is attributable to four individual animals. The error bars, representative of a confidence interval with $\alpha=0.1$ in FIG. 11 indicate the presence of extreme outliers within the data set for these time points. The cause for this IgG response in non-vaccinated animals is not readily explainable based solely on the data.

D. Conclusion

An increase in IgG antibody response can be observed over the course of vaccination in the vaccinated groups for all studies. This response increases to two weeks post vaccination and then begins to level off or drop, but is again increased by the second vaccination which occurs at Day 21. The highest antibody response levels occur between Day 28 and Day 42, with an apparent peak at Day 35.

As challenge occurred on Day 42 in all studies, any drop in antibody level from a previous peak may have affected observed efficacy. The level of antibody response from the 156A2 Triton-X derived antigen at Day 35 in Study 3 is similar to the levels observed in the sarcosyl vaccinated groups at Day 42. If these responses are generated to important protective epitopes within the vaccine preparation, a different evaluation may occur with an earlier challenge. It would be more encouraging to see the antibody response level off, rather than drop, however this may be an artifact of too low a vaccine dose, an inappropriate adjuvant, or the weak immune system of extremely young CD calves.

While the data appears to show a muted antibody response in the final study when compared to the others, it must be noted that the final reagent stocks for the ELISA were prepared following testing for the first two studies. These reagents included the coating antigen and control serums which were aliquoted into single use vials and stored at −70° C. This is intended to improve the stability of the antigens over time, but the initial freeze and thaw may have decreased the binding affinity of the coating antigen. For this reason direct comparison of signal to noise ratios between the studies should be avoided, however testing done within each study was produced by identically treated reagents.

No increase in antibody detection occurs in the control groups, with the exception of four animals at Day 35 and 42 in the final study. The reason for this increase in antibody detection for these animals is not known at this time, but could be the result of mishandled samples, premature exposure of these animals to *H. somni*, or exposure of these animals to another gram-negative bacterium with similar, cross-reactive surface antigens to *H. somni*. It does appear that the assay is capable of measuring the difference in antibody levels over time; however the specificity of the assay will need to be examined. The assay measures a generalized IgG response and it will also be important to examine the specificity of these antibodies.

Example 6

Western Blot Analysis of Immunoreactive Proteins

A. Objective

The ELISA described in this application gives a measure of total IgG response over the course of vaccination, it gives no indication as to the specificity of these antibodies, or the proteins against which these antibodies are generated. Western blots using serum from vaccinated animals to probe the various vaccine preparations were completed to better identify immunologically relevant proteins present within those preparations that showed protection. By comparing this response from groups that showed a decrease in lung pathology to those which showed no decrease, important proteins should be identified.

B. Materials and Methods

SDS-PAGE

Proteins present in the vaccine preparations were separated by molecular weight using electrophoresis. NuPAGE 10% Bis-Tris SDS gels (Invitrogen) with either a single or a twelve well configuration were used. For single well gels, samples containing 12.0 ug of total protein were combined with SDS Loading Buffer (Invitrogen) containing β-mercaptoethanol (Sigma) as a reducing agent and loaded in a 400 uL volume. A 10 uL load of Novex Sharp Pre-stained Ladder (Invitrogen) was used in the ladder well. These gels were run in 3-(N-morpholino) propanesulfonic acid (MOPS) Buffer (Invitrogen) at 200V for fifty minutes using an X-cell Electrophoresis Module (Bio-Rad). These gels were then used for membrane transfer and subsequent western blotting as described below. For twelve well gels, samples containing 2.0 ug of total protein were combined with SDS Loading Buffer (Invitrogen) containing β-mercaptoethanol (Sigma) as a reducing agent and loaded in 20 uL volumes. A 5 uL load of Novex Sharp Pre-stained Ladder (Invitrogen) was used for comparison. These gels were also run in MOPS Buffer (Invitrogen) at 200V for fifty minutes using the X-cell Electrophoresis Module (Bio-Rad). These gels were then used for Coomassie staining as described below.

Coomassie Stain

Following electrophoresis in a twelve well format, gels were submerged in Imperial Blue Gel Stain (Thermo) and stained for one hour with gentle rocking. Stain was then removed, and the gels were allowed to de-stain for twelve hours in RO water. The water was changed twice, once after thirty minutes, and once after an hour. Stained gels were then imaged and analyzed using a Model M Imager (Bio-Sciences).

Membrane Transfer

Following electrophoresis in a single well format, gels were inserted into an X-cell Blot Module (Bio-Rad). Transfer to PVDF Membranes (Invitrogen) was completed in Transfer Buffer (Invitrogen) at 30V for ninety minutes at room temperature. Successful transfer was determined by visual examination of the Novex Pre-stained Ladder. Membranes were then used for western blotting as described below.

Western Blot

Following the transfer procedure, PVDF membranes were incubated in Protein Free Blocking Buffer (PFBB) (Thermo) either for thirty minutes at room temperature with gentle shaking, or overnight at 4° C. Following blocking, membranes were washed three times for two minutes with gentle shaking using Tris-buffered Saline containing Tween (TTBS) prepared by BIVI Central Services. Washed membranes were then transferred to a Mini-Prep Multi-Screen Gasket (Bio-Rad). This gasket offers twenty lanes for probing with separate samples. Serum pools from each study group at either Day 0, Day 21, or Day 35 were diluted in PFBB to 1:500 and loaded with a 600 uL volume per well. Membranes were then incubated at room temperature with gentle shaking for one hour. Samples were then removed from the gasket by vacuum. Membranes were then transferred to plastic dishes for the remainder of the procedure. Rabbit anti-Bovine IgG (Jackson Immunolabs) diluted 1:2500 in PFBB was added to each membrane and incubated at room temperature for one hour with gentle shaking, followed by an additional wash. The final wash with TTBS was followed by two additional washes with Phosphate Buffered Saline (PBS), as suggested by manufacturer's instructions for the substrate. Opti-4CN Substrate (Bio-Rad) was prepared per manufacturer's instructions and added to the washed membranes. Substrate was allowed to develop for five minutes to maximize band formation while minimizing background. RO water was used to stop the reaction. Developed blots were allowed to dry for twelve hours and then imaged and analyzed using a Model M Imager (Bio-Sciences).

Results

A Coomassie stained gel gave a representation of all proteins present within the various OMP prep fractions used in prototype vaccine formulation regardless of their immunoreactive importance. Staining revealed a heavy concentration of proteins between 35 kDa and 40 kDa in size in the sarcosyl insoluble pellet, with less concentrated bands at approximately 80 kDa, 60 kDa, 28 kDa, and 25 kDa. A higher number of bands of varying molecular weights, with lower concentrations can be observed in both the sarcosyl soluble supernatant and SDS extract fractions. The profiles of each fraction are different, however each was shown to offer a reduction in pathology in at least one of the previously described studies. Determining which of these proteins played a role in this protection was facilitated by western blot.

Example 2

In the initial efficacy study, only the OMP vaccine candidate produced significantly lower lung pathology. Antigen from this vaccine was separated by SDS-PAGE and used for western blot analysis using serum pools from the study groups at Day 0, Day 21, and Day 35. The challenge control group in this study showed no antibody response at any of the tested time points. All vaccinate groups produced reactive bands at 80 kDa and 18 kDa. As these were observed in groups that showed no difference in lung pathology when compared to the controls, they do not seem to be immunologically important. Of interest was the detection of proteins in the 35 kDa-40 kDa range that were observed only in the OMP vaccinate group.

Example 3

In the second vaccination study, comparison of extraction methods and isolates was conducted. The Challenge Control Group was again observed to produce no antibody response over the course of vaccination. Likewise, the group vaccinated with an SDS extraction of Isolate 156A2, which produced no reduction in lung pathology, showed negligible increase in antibody response. The other groups vaccinated with a sarcosyl extraction of Isolate Lg2-OK08, sarcosyl extraction of LgD1-TN08, or SDS extractions of LgD1-TN08 showed similar reductions in mean lung scores and again display a high concentration of antibody response to proteins in the 35 kDa-40 kDa range.

Example 4

Figure 7:
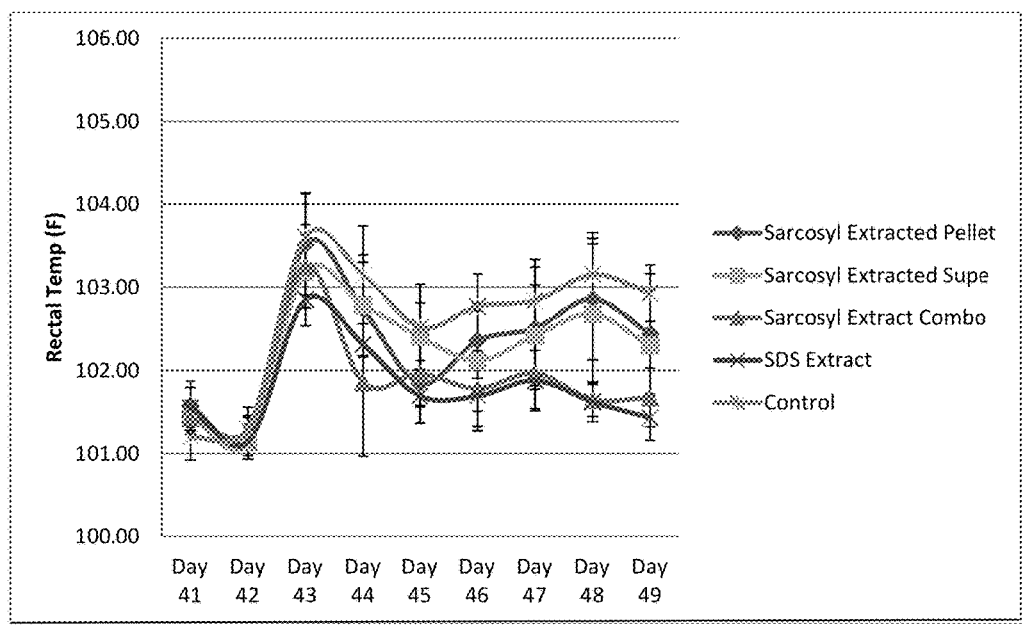
FIG. 7. is a graph illustrating mean rectal temperature by treatment group. Baseline rectal temperatures were obtained by observation both one day prior, and then immediately preceding challenge on Days −41 and 42. Rectal temperatures were recorded daily following challenge and continued until final necropsy occurred on Day 49. Error bars indicate a confidence interval with $\alpha=0.1$ representing the significant decrease in mean rectal temperature of the SDS Extract Vaccine when compared to the challenge control group beginning on Day 44 and continuing through the remainder of the challenge period.

The final host animal efficacy study examined the soluble and insoluble fractions of sarcosyl extractions, a combination of these fractions (as had been used in the previous studies), and re-examined the SDS extraction method. All vaccines for this study were generated from Isolate LgD1-TN08. For this study, each of the vaccine preps was separated via SDS-PAGE and probed with serum pools from the study groups, again using Days 0, 21, and 35. Vaccination with the sarcosyl insoluble pellet produced a mild reduction in lung pathology, which was not found to be statistically significant from the control group. This vaccine is observed to produce a similar banding pattern as was observed in blots from the previous studies, with inconsequential bands at 80 kDa and 18 kDa. It also however produces bands in the 35-40 kDa range which were deemed immunologically important by previous examinations (FIG. 7). It should also be noted that although increased IgG levels were observed via ELISA testing of the serum pool of control animals on Day 35 and Day 42 in Study 4, western blotting does not reflect this result. While the IgG detected in the ELISA bound to H. somni antigens present in a whole cell coating prep, these were not specific for any antigens present in the vaccines.

When the sarcosyl soluble fraction was separated via electrophoresis, and probed with the same serum pools, a majority of the 35-40 kDa reactivity was diminished. Seemingly inconsequential proteins of both higher and lower molecular weight are observed, however like those at 80 kDa and 18 kDa, these are common to all vaccine groups, regardless of observed efficacy. One band was observed in the sarcosyl insoluble fraction and SDS extract vaccinates only, with an approximate molecular weight of 40 kDa. Intensity of these bands was again seen to increase over the course of the vaccination phase of the study.

When the SDS extract is subjected to the same western blot procedure, reactivity in the 35 kDa-40 kDa range was again reduced when compared to that observed with a sarcosyl insoluble fraction. Similar to the sarcosyl soluble fraction, several proteins with higher or lower molecular weights were detected regardless of treatment group. Several bands were unique to the SDS vaccinates between 40 kDa and 80 kDa in size. A protein of approximately 40 kDa in size was observed to react in the sarcosyl soluble fraction as well as the SDS fraction as was observed with the blot of the soluble fraction and may be directly related to the observed efficacy.

C. Conclusion

Through examination of western blots designed to identify immunologically important proteins which generate IgG responses during vaccination, several immunoreactive proteins were identified. Consistent to all groups, regardless of vaccine efficacy, were proteins with estimated molecular weight of 80 kDa and 18 kDa respectively. While antibodies are produced against these proteins, they alone do not appear to be protective. Vaccines which produced a significant reduction in lung pathology all share a production of antibodies reactive to proteins in the 35 kDa to 40 kDa range. When used to probe vaccines containing sarcosyl insoluble material, however the sarcosyl insoluble fraction in which this banding is the most concentrated, did not confer protection by itself. The sarcosyl soluble fraction and the SDS extraction method, which were both observed to be efficacious in reducing lung pathology produce a distinct, although lower intensity band, of approximately 40 kDa in size along with multiple other weak bands observed at various molecular weights that are not seen specifically in the sarcosyl insoluble fraction.

Example 5

SDS Extracted OMPs from Isolate LgD1-TN08 were precipitated by incubation in 10% Trichloroacetic acid at 4° C. for 30 minutes followed by centrifugation at 20,000×G for 5 minutes. Protein pellets were washed in ice cold Acetone twice and then resuspended using a solution of 8M Urea, 2% CHAPS, and 100 mM DTT. Not all proteins from the extract were soluble in this suspension, but a subsequent SDS-PAGE separation and western blot using serum from animals vaccinated with the extract revealed that three immunologically relevant proteins had been recovered. Protein bands with approximate molecular weights of 41, 38, and 23 kDa were excised from a stained PVDF membrane and submitted to the Protein Facility at Iowa State University for Edman N-Terminal sequencing. Sequencing results were then inserted into BLAST analysis to determine homology to previously sequenced proteins.

Sequencing results indicate that the 41 kDa protein shares high N-Terminal homology to the fimbral subunit (fimA) of *H. somni* Isolates 2336 and 129Pt and is likely associated with pilus formation and/or secretion mechanisms. This protein is also homologous to the pilA protein of *H. ducreyi* and *H. influenza*. Efficacious response in animals vaccinated with SDS Extracted OMPs from the LgD1-TN08 isolate has correlated to induction of IgG response to this protein.

The 38 kDa protein was found to have high N-Terminal homology to the porin protein ompA which has been demonstrated to be highly conserved in many members of the Pasteurellaceae family. Again, efficacy of vaccines consisting of SDS Extracted OMPs from the LgD1-TN08 isolate has correlated with induction of IgG response to this protein.

The 23 kDa protein was most closely linked to Hs_0779, a hypothetical protein characterized only by genomics data from *H. somni* isolate 129Pt. The function of this protein has not previously been described. IgG response to this protein has been observed from animals vaccinated with SDS Extracted OMPs from the LgD1-TN08 Isolate, however this response has occurred in all vaccinates regardless of vaccine efficacy.

The BLAST results are provided as follows:
Sample: Hs_LGD1_061812-1
Comments: ~41 kDa immunoreactive OMP observed to correlate to efficacy in proof-of-concept OMP Vaccine studies.

(SEQ ID NO: 3)
Sequence:
E L M I V V A I I G I L A G I A I P Q Y Q L G

BLAST Results
E-value=4e$^{-11}$: fimbral subunit (fimA) of *H. somni* 2336 and 129Pt fimA suspected to be part of Pilus components or secretion mechanism Homologous to pilA displayed by *H. ducreyi* and *H. influenza* and many others
Sample: Hs_LGD1_061812-2
Comments: ~38 kDa immunoreactive OMP observed to correlate to efficacy in proof-of-concept OMP Vaccine studies.

(SEQ ID NO: 4)
Sequence:
A P Q A N T F Y A G A ? L

BLAST Results
E-value=1e$^{-6}$:ompA
Highly conserved in Pasteurellaceae, Porin acting as non-specific channel for small hydrophilic molecules
Sample: Hs_LGD1_061812-3
Comments: ~23 kDa immunoreactive OMP observed in all vaccinate animals regardless of efficacy (SEQ ID NO: 5)
Sequence:
S I N I A P Q I T E I L A I N G L ? Q ?

BLAST Results
E-value=0.19: Hypothetical Protein Hs_0779 of *H. somni* 129Pt
Conserved protein common to many bacteria, not characterized and unknown function
Tblast N 8/11
Calcium Transporter All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the following claims.

REFERENCES

All references cited in the specification are hereby incorporated by reference.

The following references, to the extent that they provide exemplary procedural or other details supplementary to those set forth herein, are specifically incorporated herein by reference.

Aguilar, J. C. and Rodriguez, E. G. (2007). Vaccine adjuvants revisited. *Vaccine*. 25; p 3752-3762.
Asmussen, M. D. and Baugh, C. L. 1981. Thiamine pyrophosphate (cocarboxylase) as a growth factor for *Haemophilus somnus*. *Journal of Clinical Microbiology*. 14(2); p 178-183.

Angen, O., Ahrens, P., and Tegtmeir, C. 1998. Development of a PCR test for identification of *Haemophilus somnus* in pure and mixed cultures. *Veterinary Microbiology.* 63; p 39-48.

Babcock, A. H. 2010. Epidemiology of bovine respiratory disease and mortality in commercial feedlots. Kansas State University.

Babiuk, L. A. and Potter, A. A. (1994). Veterinary vaccines. *Biotech. Adv.* 12; p 489-523.

Bollag, D. M., Rozycki, M. D., and Edelstein, S. J. (1996). *Protein Methods.* Second Ed. Wiley-Liss & Sons, Inc.; New York.

Challacombe, J. F., Duncan, A. J., Brettin, T. S., Bruce, D., Chertkov, O., Detter, J. C., Han, C. S., Misra, M., Richardson, P., Tapia, R., Thayer, N., Xie, G., and Inzana, T. J. 2007. Complete genome sequence of *Haemophilus somnus* (*Histophilus somni*) strain 129Pt and comparison to *Haemophilus ducreyi* 35000HP and *Haemophilus influenzae* Rd. *Journal of Bacteriology.* 189(5); p 1890-1898.

Chimini, G. and Chavrier, P. 2000. Function of Rho family proteins in actin dynamics during phagocytosis and engulfment. *Nat. Cell Biol.* 2; p 191-196.

Costerton, J. W. 1999. Introduction to biofilm. *International Journal of Antimicrobial Agents.* 11; p 217-221.

Cox, A. D., Howard, M. D., Brisson, J. R., Van Der Zwan, M., Thibault, P., Perry, M. B., and Inzana, T. J. 1998. Structural analysis of the phase-variable lipooligosaccharide from *Haemophilus somnus* strain 738. *Eur. J. Biochem.* 253; p 507-516.

Detmer, A. and Glenting, J. Live bacterial vaccines—a review and identification of potential hazards. *Microbial Cell Factories.* 5:23; Bio Med Central <http://www.microbialcellfactories.com/content/5/1/23>

Duff, G. C. and Galyean, M. L. 2011. Recent advances in management of highly stressed, newly received feedlot cattle. *Journal of Animal Science.* 85; p 823-840.

Ekins, A., Bahrami, F., Sijercic, A., Maret, D., and Niven, D. F. 2004. *Haemophilus somnus* possesses two systems for acquisition of transferrin-bound iron. *Journal of Bacteriology.* 186(13); p 4407-4411.

Elswaifi, S. F. 2006. The molecular characterization of phosphorylcholine (ChoP) on *Histophilus somni* lipooligosaccharide: Contribution of ChoP to bacterial virulence and pathogenesis. Virginia Polytechnic Institute and State University.

Fulton, R. W., Cook, B. J., Step, D. L., Confer, A. W., Saliki, J. T., Payton, M. E., Burge, L. J., Welsh, R. D., Blood, K. S., 2002. Evaluation of health status of calves and the impact on feedlot performance: assessment of a retained ownership program for postweaning calves. *Can. J. Vet. Res.* 66, 173-180.

Geertsema, R. S., Worby, C., Kruger, R. P., Tagawa, Y., Russo, R., Herdman, D. S., Lo, K., Kimball, R. A., Dixon, J., and Corbeil, L. B. 2008. Protection of mice against *H. somni* septicemia by vaccination with recombinant immunoglobulin binding protein subunits. *Vaccine.* 26; p 4506-4512.

Geertsema, R. S., Zekarias, B., La Franco Scheuch, L., Worby, C., Russo, R., Gershwin, L. J., Herdman, D. S., Lo, K., and Corbeil, L. B. 2011. IbpA DR2 subunit immunization protects calves against *Histophilus somni* pneumonia. *Vaccine.* 29; 4805-4812.

Griffin, D. 1997. Economic impact associated with respiratory disease in beef cattle. *Vet. Clin. North Am. Anim. Pract.* 13; p 367-377.

Griffin, D. 2010. Bovine pasteurellosis and other bacterial infections of the respiratory tract. *Veterinary Clinics of North American Food Animal Practice.* 26(1); p 57-71

Hobb, R. I., Fields, J. A., Burns, C. M., and Thompson, S. A. 2009. Evaluation of procedures for outer membrane isolation from *Campylobacter jejuni. Microbiology.* 155 (3); p 979-988.

Howard, M. D., Cox, A. D., Weiser, J. N., Schurig, G. G., and Inzana, T. J. 2000. Antigenic diversity of *Haemophilus somnus* lipooligosaccharide: Phase-variable accessibility of the phosphorylcholine epitope. *Journal of Clinical Microbiology.* 38(12); p 4412-4419.

Inzana, T. J., Iritani, B., Gogolewski, R. P., Kania, S. A., and Corbeil, L. B. 1988. Purification and characterization of lipooligosaccharides from four strains of *Haemophilus somnus. Infection and Immunity.* 56(11); p 2830-2837.

Inzana, T. J., Gogolewski, R. P., and Corbeil, L. B. 1992. Phenotypic phase variation in *Haemophilus somnus* lipooligosaccharide during bovine pneumonia and after in vitro passage. *Infection and Immunity.* 60(7); p 2943-2951.

Inzana, T. J., Glindemann, G., Cox, A. D., Wakarchuk, W., and Howard, M. D. 2002. Incorporation of N-Acetylneuraminic Acid into *Haemophilus somnus* lipooligosaccharide (LOS): Enhancement of resistance to serum and reduction of LOS antibody binding. *Infection and Immunity.* 70(9); p 4870-4879.

Jaques, M. and Paradis, S. E. 1998. Adhesin-receptor interactions in Pasteruellaceae. *FEMS Microbiol. Rev.* 22; p 45-59.

Jericho, K. W. F. and Langford, E. V. 1982. Aerosol vaccination of calves with *Pasteurella haemolytica* against experimental respiratory disease. *Can. J. comp. Med.* 46; p 287-292.

Johnson, A. P. and Inzana, T. J. 1986. Loss of ciliary activity in organ cultures of rat trachea treated with lipo-oligosaccharide from *Haemophilus influenzae. J. Med. Microbiol.* 22; p 265-268.

Kania, S. A., Gogolewski, R. P., and Corbeil, L. B. 1990. Characterization of a 78-kilodalton outer membrane protein of *Haemophilus somnus. Infection and Immunity.* 58(1); p 237-244.

Korczak, B., Christensen, H., Emler, S., Frey J., and Kuhnert, P. 2004. Phylogeny of the family Pasteurellaceae based on rpoB sequences. *International Journal of Systemic and Evolutionary Microbiology.* 54; p 1393-1399.

Murphy, K., Travers, P., and Walport, M. (2008). *Janeway's Immunobiology:* 7th Ed. Garland Science; NYC.

Nikaido, H. and Nakae, T. 1979. The outer membrane of gram-negative bacteria. *Advances in Microbial Physiology.* 20; p 163-250.

O'Toole, D., Hunter, A. R., and Corbeil, L. B. 2009. Diagnostic exercise: myocarditis due to *Histophilus somni* in feedlot and backgrounded cattle. *Veterinary Pathology.* 46; p 1015-1017.

Rehm, H. 2006. *Protein Biochemistry and Proteomics.* Elsevier Academic Press; New York.

Ribble, C. S., Jim, G. K., and Janzen, E. D. 1988. Efficacy of immunization of feedlot cattle with a commercial *Haemophilus somnus* bacterin. *Canadian Journal of Veterinary Research.* 52: p 191-198.

Roth, J. A. 2007. Mechanistic basis for adverse vaccine reactions and vaccine failures. *Advances in Veterinary Medicine.* 41: p 681-700.

Roy, C. R. and Mukherjee, S. 2009. Bacterial Fic proteins amp up infection. *Science Signaling.* 2(62), p 14. [DOI: 10.1126/scisignal.262.0pe14].

Sandal, I., Shao, J. Q., Annadata, S., Apicella, M. A., Boye, M., Jensen, T. K., Saunders, G. K., and Inzana, T. J. 2009. *Histophilus somni* biofilm formation in cardiopulmonary tissue of the bovine host following respiratory challenge. *Microbes and Infection.* 11; p 254-263.

Sandal, I. and Inzana T. 2010. A genomic window into the virulence of *Histophilus. Trends in Microbiology.* 18(2): p 90-99.

Spickler, A. R. and Roth, J. A. 2003. Adjuvants in veterinary vaccines: Modes of action and adverse effects. *J Vet Intern Med;* 17, p 273-281.

St. Michael, F., Inzana, T. J., and Cox, A. D. 2006. Structural analysis of the lipooligosaccharide-derived oligosaccharide of *Histophilus somni* (*Haemophilus somnus*) strain 8025. *Carbohydrate Research.* 341; p 281-284.

Tagawa, Y. et. al. (1993). Antigenic analysis of the major outer membrane protein of *Haemophilus somnus* with monoclonal antibodies. *Infection and Immunity.* 61(5); p 2257-2259.

Tagawa, Y., Ishikawa, H., and Yuasa, N. 1993. Purification and partial characterization of the major outer membrane protein of *Haemophilus somni. Infection and Immunity.* 61(1); p 91-96.

Tagawa, Y. Haritani, M., Ishikawa, H., and Yuasa, N. 1993. Characterization of a heat-modifiable outer membrane protein of *Haemophilus somnus. Infection and Immunity.* 61(5); p 1750-1755.

Tagawa, Y., Bastida-Corcuera, F., and Corbeil, L. B. 2000. Immunological characterization of the major outer membrane protein of *Haemophilus somnus. Veterinary Microbiology.* 71; p 245-254.

Tremblay, Y. D., Bahrami, F., and Niven, D. F. 2006. Acquisition of haemoglobin-bound iron by *Histophilus somni. Vet. Microbiol.* 114; p 104-114.

Ward, A. C., Weiser, G. C., Anderson, B. C., Cummings, P. J., Arnold, K. F., and Corbeil, L. B. 2006. *Haemophilus somnus* (*Histophilus somni*) in bighorn sheep. *Canadian Journal of Veterinary Research.* 70; p 34-42.

Worby, C. A., Mattoo, S., Kruger, R. P., Corbeil, L. B., Koller, A., Mendez, J. C., Zekarias, B., Lazar, C., and Dixon, J. E. 2009. The Fic domain: a new paradigm for adenylylation. *Mol. Cell.* 34(1): 93. Doi:10.1016/j.molcel.2009.03.008.

Woolery, A. R., Luong, P., Broberg, C. A., and Orth, K. 2010. AMPylation: something old is new again. *Frontiers in Microbiology.* 1; doi: 10.3389/fmicb.2010.00113.

Xiao, J. Worby, C. A., Mattoo, S., Sankaran, B., and Dixon, J. E. 2010. Structural basis for Fic mediated adenylylation. *Nat. Struct. Mol. Biol.* 17(8); p 1004-1010.

Yarnall, M., Widders, P. R., and Corbiel, L. B. 1988. Isolation and characterization of Fc receptors from *Haemophilus somnus. Scand. J. Immunol.* 28; p 129-137

Zekarias, B., Mattoo, S., Worby, C., Lehmann, J., Rosenbusch, R. F., and Corbeil, L. B. 2010. *Histophilus somni* IbpA DR2/Fic in virulence and immunoprotection at the natural host alveolar epithelial barrier. *Infection and Immunity.* 78(5); p 1850-1858.

Zekarias, B., O'Toole, D., Lehmann, J., and Corbeil, L. B. 2011. *Histophilus somni* IbpA Fic cytotoxin is conserved in disease strains and most carrier strains from cattle; sheep and bison. *Veterinary Microbiology.* 149 (1-2); p 177-185.

---

What is claimed is:

1. An immunogenic composition comprising at least one outer membrane protein (OMP) from *Histophilus somni* selected from the group consisting of PTA 12755, PTA 12756 and combinations thereof and a physiologically-acceptable vehicle, wherein the OMP is generated by incubating *Histophilus somni* bacteria, suspending *Histophilus somni* bacteria in 4-(2-hydroxyethyl)-1-piperazineethanesulfonic acid (HEPES) buffer containing protease inhibitors, lysing the *Histophilus somni* bacteria by cycles of freezing and thawing, and further *Histophilus somni* bacteria lysing by sonication cycles, resuspending in HEPES containing protease inhibitors, and then solubilizing non-protein components and then extracting solely by SDS extraction.

2. The immunogenic composition of claim 1, wherein the physiologically-acceptable vehicle is selected from the group consisting of a pharmaceutically or veterinary acceptable carrier, adjuvant, or combination thereof.

3. A method of provoking an immune response against *Histophilus somni* infection comprising the administration of the immunogenic composition of claim 1 to a subject.

4. A method of reducing the incidence or severity of a clinical sign associated with *Histophilus somni* infection comprising the administration of the immunogenic composition of claim 1 to a subject in need thereof, wherein the reduction of the incidence of or the severity of a clinical sign is at least 10% relative to a subject not receiving the immunogenic composition.

5. The method of claim 4, wherein the clinical sign is selected from the group consisting of labored or rapid respiration, coughing, anorexia, depression or lethargy, nasal and ocular discharge, and mortality.

6. The method of claim 4, wherein the subject is an animal selected from the group consisting of a bovine or ovine.

7. A kit comprising at least one OMP *Histophilus somni* peptide according to claim 1, an immunogenic carrier, a container for packaging the OMP *Histophilus somni* peptide and immunogenic carrier, a set of printed instructions; and a dispenser capable of administering a vaccine to an animal.

8. A kit for preparing the immunogenic composition of claim 1, comprising (i) the OMP *Histophilus somni* peptide and (ii) the physiologically-acceptable vehicle, wherein (i) and (ii) are packaged separately.

9. The kit of claim 8, further comprising a dispenser.

* * * * *

SEQUENCE LISTING

```
<160> NUMBER OF SEQ ID NOS: 5

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gaaggcgatt agtttaagag                                                     20

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ttcgggcacc aagtrttca                                                      19

<210> SEQ ID NO 3
<211> LENGTH: 23
<212> TYPE: PRT
<213> ORGANISM: Unknown
<220> FEATURE:
<223> OTHER INFORMATION: Description of Unknown: Hs_LGD1_061812-1
      peptide

<400> SEQUENCE: 3
```

```
Glu Leu Met Ile Val Val Ala Ile Ile Gly Ile Leu Ala Gly Ile Ala
1               5                   10                  15

Ile Pro Gln Tyr Gln Leu Gly
            20

<210> SEQ ID NO 4
<211> LENGTH: 13
<212> TYPE: PRT
<213> ORGANISM: Unknown
<220> FEATURE:
<223> OTHER INFORMATION: Description of Unknown: Hs_LGD1_061812-2
      peptide
<220> FEATURE:
<221> NAME/KEY: MOD_RES
<222> LOCATION: (12)..(12)
<223> OTHER INFORMATION: Any amino acid

<400> SEQUENCE: 4

Ala Pro Gln Ala Asn Thr Phe Tyr Ala Gly Ala Xaa Leu
1               5                   10

<210> SEQ ID NO 5
<211> LENGTH: 20
<212> TYPE: PRT
<213> ORGANISM: Unknown
<220> FEATURE:
<223> OTHER INFORMATION: Description of Unknown: Hs_LGD1_061812-3
      peptide
<220> FEATURE:
<221> NAME/KEY: MOD_RES
<222> LOCATION: (18)..(18)
<223> OTHER INFORMATION: Any amino acid
<220> FEATURE:
<221> NAME/KEY: MOD_RES
<222> LOCATION: (20)..(20)
<223> OTHER INFORMATION: Any amino acid

<400> SEQUENCE: 5

Ser Ile Asn Ile Ala Pro Gln Ile Thr Glu Ile Leu Ala Ile Asn Gly
1               5                   10                  15

Leu Xaa Gln Xaa
            20
```